(12) United States Patent
Sugaya et al.

(10) Patent No.: US 9,358,234 B2
(45) Date of Patent: *Jun. 7, 2016

(54) MAMMALIAN MULTIPOTENT STEM CELLS AND COMPOSITIONS, METHODS OF PREPARATION AND METHODS OF ADMINISTRATION THEREOF

(75) Inventors: Kiminobu Sugaya, Winter Park, FL (US); Tingyu Qu, Chicago, IL (US); Ankur V. Vaghani, Chicago, IL (US); Christopher Brannen, Vancouver, WA (US); Hojoong M. Kim, Chicago, IL (US); Jose S. Pulido, Brookfield, WI (US); Xiajing Dong, Oak Park, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 292 days.

This patent is subject to a terminal disclaimer.

(21) Appl. No.: 13/488,531

(22) Filed: Jun. 5, 2012

(65) Prior Publication Data

US 2014/0037589 A1    Feb. 6, 2014

Related U.S. Application Data

(63) Continuation of application No. 12/644,425, filed on Dec. 22, 2009, now Pat. No. 8,192,732, which is a continuation of application No. 10/345,126, filed on Jan. 14, 2003, now Pat. No. 7,635,467.

(60) Provisional application No. 60/348,473, filed on Jan. 14, 2002, provisional application No. 60/357,783, filed on Feb. 19, 2002, provisional application No. 60/376,257, filed on Apr. 29, 2002, provisional application No. 60/381,138, filed on May 8, 2002, provisional application No. 60/404,361, filed on Aug. 19, 2002, provisional application No. 60/430,381, filed on Dec. 2, 2002.

(51) Int. Cl.
| | |
|---|---|
| *C12N 5/0775* | (2010.01) |
| *C12N 5/0797* | (2010.01) |
| *A61K 31/505* | (2006.01) |
| *A61K 31/519* | (2006.01) |
| *A61K 31/7088* | (2006.01) |
| *C12N 5/079* | (2010.01) |
| *A61K 35/12* | (2015.01) |

(52) U.S. Cl.
CPC ............. *A61K 31/519* (2013.01); *A61K 31/505* (2013.01); *A61K 31/7088* (2013.01); *C12N 5/0621* (2013.01); *C12N 5/0623* (2013.01); *C12N 5/0662* (2013.01); *A61K 35/12* (2013.01); *C12N 2500/90* (2013.01); *C12N 2500/99* (2013.01); *C12N 2501/06* (2013.01); *C12N 2501/11* (2013.01); *C12N 2501/115* (2013.01); *C12N 2501/15* (2013.01); *C12N 2501/165* (2013.01); *C12N 2501/91* (2013.01); *C12N 2501/998* (2013.01); *C12N 2501/999* (2013.01); *C12N 2502/08* (2013.01); *C12N 2506/1353* (2013.01)

(58) Field of Classification Search
CPC ..... A61K 35/12; A61K 35/30; A61K 31/505; A61K 2035/124; C12N 5/0623; C12N 2506/1353; C12N 5/0607; C12N 5/0663; C12N 5/0618

See application file for complete search history.

(56) References Cited

U.S. PATENT DOCUMENTS

| | | | |
|---|---|---|---|
| 4,959,368 A | 9/1990 | Awaya | |
| 5,104,650 A | 4/1992 | Ralph et al. | |
| 5,411,883 A | 5/1995 | Boss et al. | |
| 5,589,376 A | 12/1996 | Anderson et al. | |
| 5,750,376 A * | 5/1998 | Weiss et al. | ................ 435/69.52 |
| 5,753,506 A | 5/1998 | Johe | |
| 5,766,948 A | 6/1998 | Gage et al. | |
| 5,851,832 A | 12/1998 | Weiss et al. | |
| 5,925,567 A | 7/1999 | Kraus et al. | |
| 5,968,829 A | 10/1999 | Carpenter | |
| 5,976,523 A | 11/1999 | Awaya et al. | |
| 5,980,885 A | 11/1999 | Weiss et al. | |
| 6,013,521 A | 1/2000 | Gage et al. | |
| 6,020,197 A | 2/2000 | Gage et al. | |
| 6,040,180 A | 3/2000 | Johe | |
| 6,090,624 A | 7/2000 | Greenwood et al. | |
| 6,117,675 A | 9/2000 | Van der Kooy et al. | |
| 6,254,865 B1 | 7/2001 | Freed et al. | |
| 6,284,245 B1 | 9/2001 | Edge | |
| 6,306,575 B1 | 10/2001 | Thomas et al. | |
| 6,368,854 B2 | 4/2002 | Weiss et al. | |
| 6,497,872 B1 | 12/2002 | Weiss et al. | |

(Continued)

FOREIGN PATENT DOCUMENTS

| | | |
|---|---|---|
| EP | 0192783 | 9/1986 |
| EP | 0305184 | 3/1989 |

(Continued)

OTHER PUBLICATIONS

Clementi, et al. Adv. Exp. Med. Biol. 296:91-102, 1991.*

(Continued)

*Primary Examiner* — Daniel C Gamett

(74) *Attorney, Agent, or Firm* — Timothy H. Van Dyke; Beusse, Wolter, Sanks & Maire, PLLC

(57) ABSTRACT

This invention provides methods for preparing novel mammalian multipotent stem cells (MSCs), compositions thereof, and methods of preparing and administering the cells.

6 Claims, 35 Drawing Sheets

(56) References Cited

U.S. PATENT DOCUMENTS

| | | | |
|---|---|---|---|
| 6,638,501 B1 | 10/2003 | Bjornson | |
| 6,670,397 B1 | 12/2003 | Baranowitz | |
| 6,808,702 B2 | 10/2004 | Pasricha et al. | |
| 6,824,973 B2 | 11/2004 | Tang et al. | |
| 6,833,269 B2 | 12/2004 | Carpenter | |
| 2001/0038836 A1 | 11/2001 | During et al. | |
| 2002/0091133 A1 | 7/2002 | Taylor | |
| 2002/0142457 A1 | 10/2002 | Umezawa et al. | |
| 2002/0146821 A1 | 10/2002 | Sanchez-Ramos et al. | |
| 2002/0168350 A1 | 11/2002 | Brazelton et al. | |
| 2002/0168765 A1 | 11/2002 | Prockop et al. | |
| 2003/0053992 A1 | 3/2003 | Rader et al. | |
| 2003/0059868 A1 | 3/2003 | Greenwood et al. | |
| 2003/0118566 A1 | 6/2003 | Neuman et al. | |
| 2003/0139410 A1 | 7/2003 | Sugaya et al. | |
| 2003/0148513 A1 | 8/2003 | Sugaya et al. | |
| 2003/0219898 A1 | 11/2003 | Sugaya et al. | |
| 2004/0034049 A1 | 2/2004 | Okawa et al. | |
| 2004/0103448 A1 | 5/2004 | Bjorklund | |
| 2004/0106197 A1 | 6/2004 | Okano et al. | |
| 2005/0142660 A1* | 6/2005 | Lou et al. | 435/368 |
| 2005/0169897 A1 | 8/2005 | Snyder et al. | |
| 2005/0181503 A1 | 8/2005 | Goldman et al. | |

FOREIGN PATENT DOCUMENTS

| | | |
|---|---|---|
| EP | 0612746 | 8/1994 |
| EP | 0 648 495 | 4/1995 |
| JP | 64-040483 | 2/1989 |
| JP | 64-079183 | 3/1989 |
| JP | 1-139572 | 6/1989 |
| JP | 7-90002 | 4/1995 |
| JP | 8-502172 | 3/1996 |
| JP | 8-325268 | 12/1996 |
| JP | 9-507747 | 8/1997 |
| JP | 9-295946 | 11/1997 |
| JP | 9-328435 | 12/1997 |
| JP | 10-504308 | 4/1998 |
| JP | 2001-504123 | 3/2001 |
| JP | 2001-526884 | 12/2001 |
| JP | 2002-50064 | 1/2002 |
| JP | 2002-502858 | 1/2002 |
| JP | 2002-518990 | 7/2002 |
| WO | WO87/04928 | 8/1987 |
| WO | WO89/01938 | 3/1989 |
| WO | WO93/01275 | 1/1993 |
| WO | WO94/09119 | 4/1994 |
| WO | WO94/10292 | 5/1994 |
| WO | WO94/16718 | 8/1994 |
| WO | WO95/13364 | 5/1995 |
| WO | WO96/04789 | 2/1996 |
| WO | PCT/CA9500637 | 5/1996 |
| WO | WO96/15226 | 5/1996 |
| WO | WO98/22127 | 5/1998 |
| WO | WO98/32457 | 7/1998 |
| WO | WO99/11758 | 3/1999 |
| WO | WO99/32606 | 7/1999 |
| WO | WO99/40107 | 8/1999 |
| WO | WO99/43286 | 9/1999 |
| WO | PCT/US99/27613 | 5/2000 |
| WO | WO00/29550 | 5/2000 |
| WO | WO00/69448 | 11/2000 |
| WO | WO01/11011 | 2/2001 |
| WO | WO01/34167 | 5/2001 |
| WO | WO01/53461 | 7/2001 |
| WO | WO01/59072 | 8/2001 |
| WO | WO02/064748 | 8/2002 |
| WO | PCT/US03/01254 | 7/2003 |
| WO | WO03/060085 | 7/2003 |
| WO | WO2005/009359 | 2/2005 |

OTHER PUBLICATIONS

Coleman et al., Developmental Biology (1969), 19(6): 527-548 Abstract, Caplus Accession No. 1969:420164.*
Kidson et al., Experimental Cell Research, vol. 188, Issue 1, May 1990, pp. 36-41, Abstract).*
Lindvall et al., Nature Medicine 10, S42-S50 (2004).*
Lu et al., Journal of Neurotrauma. Aug. 2001, 18(8): 813-819.*
Chopp et al (2000) Neuroreport 11 (13 ):3001-3005.*
Hofstetter et al (2002) PNAS 99(4): 2199-2204.*
Alvarez-Buylla et al., 1997, J. Neurobiology 33: 585-601.
Andrews et al. TNF a potentiates IFN g-induced cell death in oligodendrocyte progenitors. Journal of Neuroscience Research. Dec. 1998, vol. 54, No. 5, pp. 574-583.
Awaya, Akira, et al., Neurotropic Pyrimidine Heterocyclic Compounds. I. The Newly Synthesized Pyrimidine Compounds Promote Neurite Outgrowth of GOTO and Neuro 2a Neuroblastoma Cell Lines, and Potentiate Nerve Growth Factro (NFG)-Induced Neurite Sprouting of PC 12 Cells, >>Bio. Pharm, Bull., 1993, 16(3), pp, 248-253.
Bayarshaihan, D. et al. Rapid identification of novel chondrocyte-specific gene by RNA differential display, Biochem and Biophys. Res. Comm. 1995. vol, 220, pp. 449-452.
Benninger et al., 2000, Brain Pathol. 10: 330-341.
Blakemore et al., 1991, Trends Neurosci. 14 : 323-327.
Blakemore et al., 2000, Cell Transplant. 9: 289-294.
Brannen et al., 2000, Neuroreport 11: 1123-8.
Brewer, Regeneration and proliferation of embryonic and adult rat hippocampal neurons in culture. Experimental Neurology. Sep. 1999, vol. 159, No. 1 pp. 237-247.
Brickman et al., The Journal of Biological Chemistry, 1995, 270:24941-24948.
Burt et al. Treatment of autoimmune disease by intense immunosuppressive conditioning and autologous hematopoietic stem cell transplantation. Blood, 1998, vol. 92, No. 10, pp. 3505-3514.
Carpenter et al., 1999, Experimental Neurology 158: 265-278.
Cattaneo et al., 1996, Mol. Brain Res. 42: 161-66.
Cheng, C. et al. In vivo proliferation, Migration and phenotypic changes of Schwann cells in the presence of myelinated fibers. Neuroscience. Nov. 2002, vol. 115, No. 1, pp. 321-329.
Daadi et al., Generation of tyrosine hydroxylase-producing neurons from precursors of the embryonic and adult forebrain. The Journal of Neuroscience. Jun. 1, 1999, vol. 19, No. 11, pp. 4484-4497.
Doetsch et al., 1999, Cell 97: 703-16.
Eckenstein et al., 1994, Biochem. Pharmacol. 47: 103-110.
Ferrari et al., (1998), Muscle regeneration by bone marrow-derived myogenic progenitors, Science 270: 1528.
Fricker et al., 1999, J. Neurosci, 19 : 5990-6005.
Frölichsthal-Schoeller et al., 1999, NeuroReport 10: 345-351.
Fukuyama et al., <<A synthesized pyrimidine compound, MS-818, promotes waking function recovery from crush injury of the sciatic nerve through its indirect stimulation of Schwann cells >> Restorative Neurology and Neuroscience 17 (2000) 9-16.
Gonzalez et al., 1995, Brain Res. 701: 201-226.
Gould et al., 1999, Science 286 : 548-552.
Gussoni el al., (1999), Dystrophin expression in the mdx mouse restored by stem cell transplantation, nature 401: 390.
Hatton et al., 1992, Gila 5 : 251-258.
International Preliminary Examination Report of Nov. 5, 2003 for PCT/US03/01254.
International Preliminary Examination Report of Dec. 23, 2003 for PCT/US03/01014.
International Preliminary Examination Report of Dec. 31, 2003 for PCT/US03/01258.
Itoh et al., "The Effect of neurotrophic pyrimidine heterocyclic compounds, MS-818 and MS-430, on the regeneration of injured peripheral nerves" Restorative Ndurology and Neuroscience 14:265-273 (1999).
Jiang et al., "The effect of MS-818, a pyrimidine compound, on the regeneration of peripheral nerve fibers of mice after a crush injury" Acta Neuropathol 90:130-134 (1995).
Johansson et al., 1999, Cell 96: 25-34.
Kessler PD, (1999), Myoblast cell grafting into heart muscle: cellular biology and potential applications, Annu. Rev. Physiol. 61:219.

(56) References Cited

OTHER PUBLICATIONS

Kohyama, Jun, et al., "Brain From Bone: Efficient 'Meta-Differentiation' of Marrow Stroma-Derived Mature Osteoblasts to Neurons with Noggin or A Demethylating Agent," Differentiation, 2001, vol. 68, pp. 235-244.
Koyama et al., <<Neurotropic Pyrimidine Heterocyclic Compounds. II. Effects of Novel Neurotropic Pyrimidine Derivatives on Astrocytic Morphological Differentiation >>Biol. Pharm. Bull. 20(2) 138-141 (1997).
Kurimoto et al., 2001, Neurosci Let. 306: 57-60.
Lundberg et al., 1996, Exp. Neurol. 139:39-53.
Mazurova et al. New therapeutic approaches for the treatment of Huntington's Disease. Acta Medica 2001. vol. 44, No. 4, pp. 119-123.
Memberg et al. Proliferation, differentiation and survival of rat sensory neuron precursors in vitro require specific trophic factors. Molecular and Cellular Neuroscience. Aug. 1995, vol. 6, No. 4, pp. 323-335.
Murphy et al. Neural Stem Cells. Journal of Investigative Dermatology Symposium Proceedings. Aug. 1997, vol. 2, No. 1, pp. 8-13.
Nodu, Masayuki, et al., "Increase of Nerve Regeneration Capacity by New Neutrotrophic Pyrimidine Derivative MS-430," Gen. Pharmac., 1998, vol. 31, No. 5, pp. 821-824.
Ohnishi, Akio, et al., "The Effect of MS-430, a Synthetized Pyrimidine Compound, on regeneration of Nerve Fibers of Rats after Crush Injury," J UOEH, 1995, 17(2), pp. 131-139.
Pagan, R. et al., Epithelial-mesenchymal transition of cultured rat neonatal hepatocytes is differentially regulated in response to epidermal growth factor and dimethyl sulfoxide. 1997, Hepatology, vol. 25, No. 3, pp. 598-606.
Pereira et al, (1995), Cultured adherent cells from marrow can serve as long-lasting precursor cells for bone, cartilage, and lung in irradiated mice, PNAS 62: 4857.
Petersen et al, (1999), Bone marrow as a potential source of hepatic oval cells, Science 284: 1168.
Pittenger et al., (1999), Multineage potential of adult human mesenchymal stem cells, Science 284: 143.
Prockop et al., (1997) Marrow stromal cells as stem cells for nonhematopoietic tissues, Science 276:71.
Pundt et al., 1995, Brain Res. 695: 25-36.
Qu et al., 2001, Neuroreport 12 : 1127-32.
Qu et al., (2001), Society for Neuroscience Abstracts, "In vivo differentiation and migration properties of mesenchymal stem cells", vol. 27 (1), p. 969; $31^{st}$ Annual Meeting of the Society for Neuroscience; San Diego, California, USA; Nov. 10-15, 2001.
Qu et al., (2002), Society for Neuroscience Abstracts Viewer and Itinerary Planner, "A seven fold increase in neural stem cell population is induced by pyrimidine derivative MS-818", Abstract No. 825.8 $32^{nd}$ Annual Meeting of the Society for Neuroscience; Orlando, FL USA Nov. 2-7, 2002.
Rosser et al., 2000, Eur . J. Neurosci. 12: 2405-2413.
Rubio et al., 2000, Mol. Cell Neurosci. 16: 1-13.
Sager, Ruth, et al., "Pre-Adipocyte Determination either by Insulin or by 5-Azacytidine," Proc. Natl. Acad. Sci., Cell Biology, 1982. vol. 79, pp. 480-484.
Sanjo et al. A novel neutrophic pyrimidine compound MS-818 enhances neurotrophic effects of basic fibriblast growth factor. Journal of Neuroscience Research, 1998, vol. 54, pp. 504-612.
Sugiyama et al., <<Accleration by MS-818 of Early Muscle Regeneration and Enhanced Muscle Recovery after Surgical Transection >>Muscle & Nerve Feb. 2002 218-229.
Svendsen et al., 1998, J. Neurosci. Methods 85 : 141-152.
Svendsen et al., 1999, Brain Pathol. 9: 499-513.
Torigoe et al., <<A newly synthesized neurotropic pyrimidine compured, MS-818, may activate migratory Schwann cells in peripheral nerve regeneration Brain Research 787®1998) 337-340.
Warfvinge et al., 2001, Exp. Neurol. 169: 1-12.
Watanabe et al., "A Neurotrophic Pyrimidine Compound, MS-818, Enhances EGF-Induced Restoration of Gastric Epithelial Wounds in Vitro" J. Clin. Gastroenterol 1988:27 (Suppl. 1) S105-S109.
Williams et al., 1996, J. Comp. Neurol. 370: 147-158.
Yasuhare et al., <<The Neurotrophic Pyrimidine Heterocyclic Compound MS-818 Promotes the Angiogenesis induced by Basic FGF >>Int. J. Clin. Pharm. Res. XV(5/6) 167-174(1995).
Yoshikawa et al., "The Effect of MS-818, Newly Synthesized Pyrimidine Compound, on Fracture Repair" Kobe J. Med. Sci. 46:265-282 (Dec. 2000).

\* cited by examiner

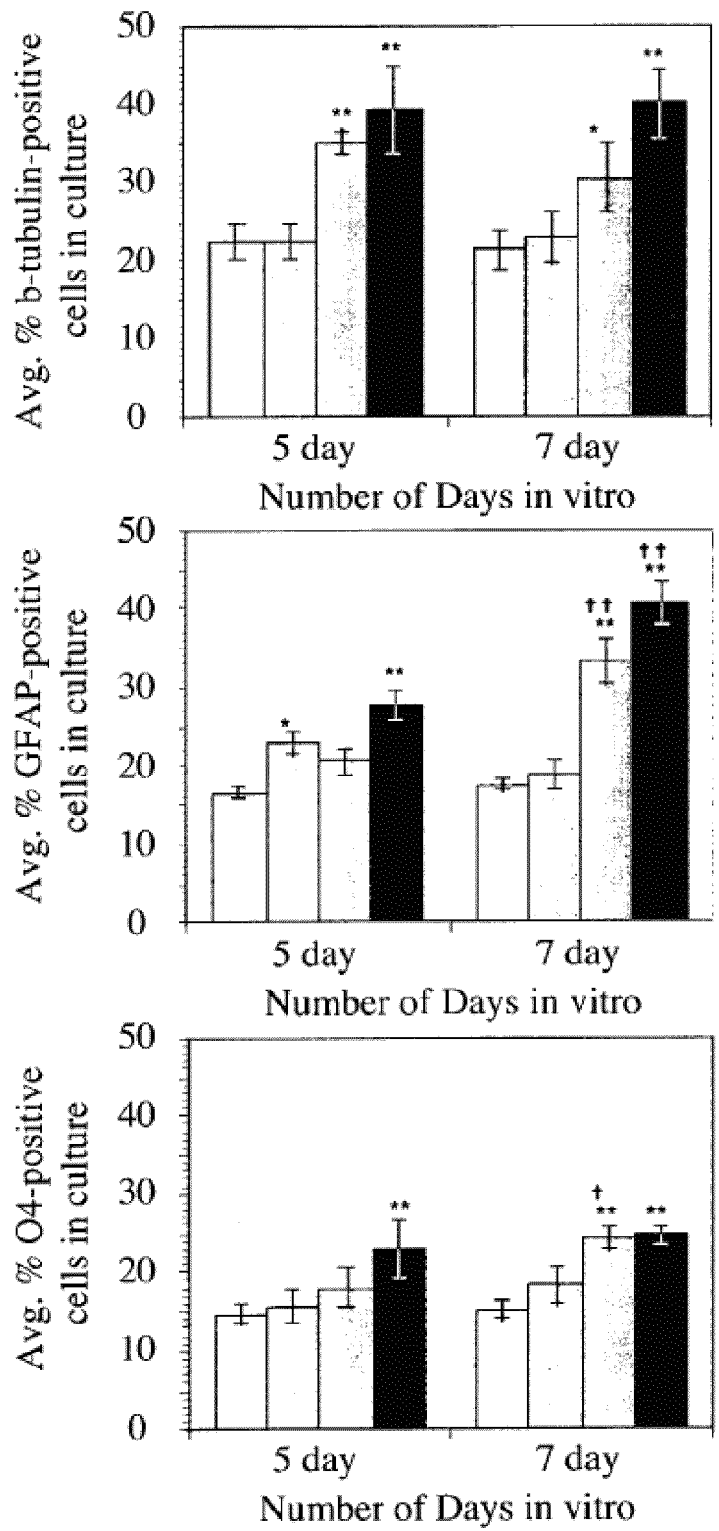
Figure 6 (II)

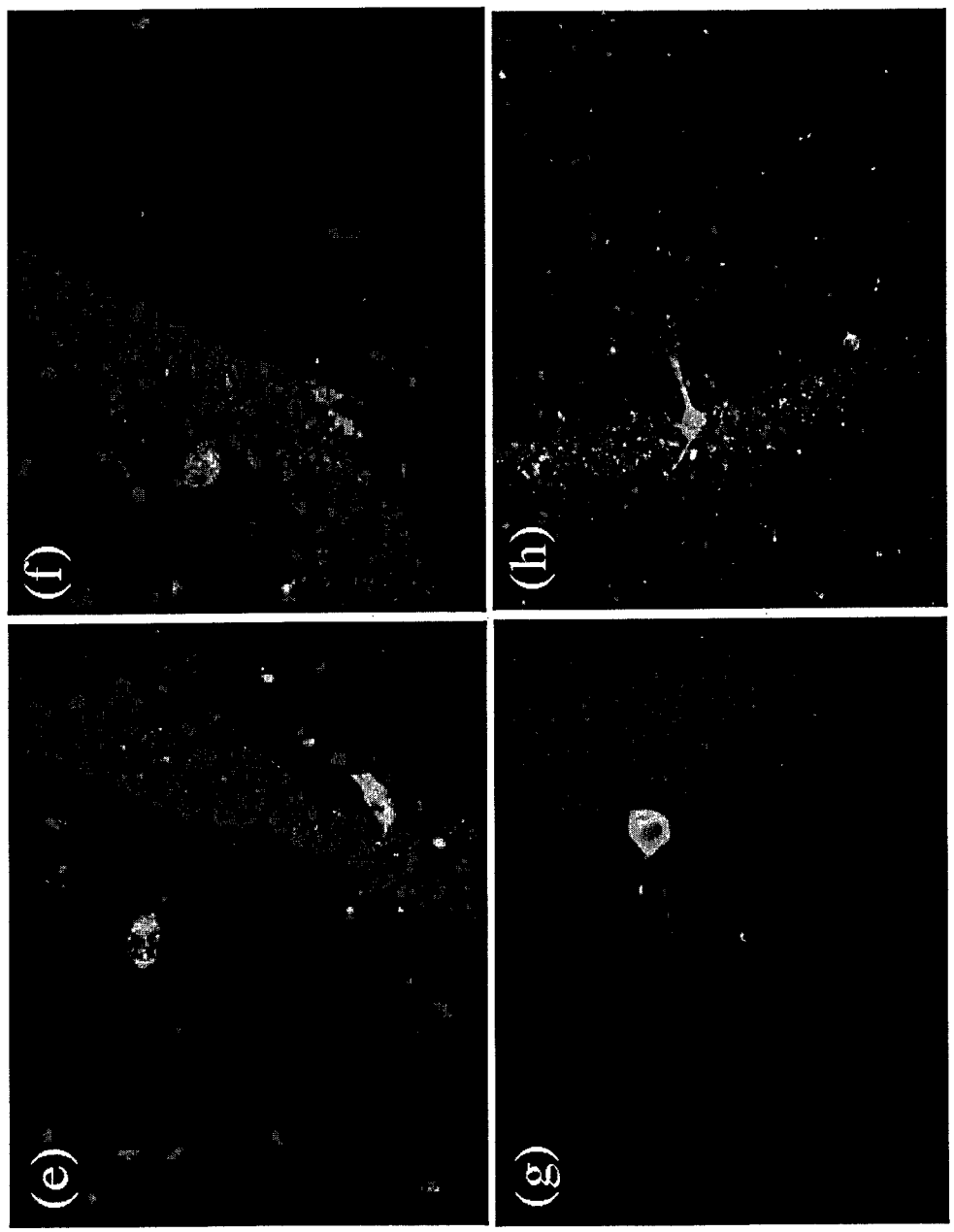
Figure 9 (II)

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ttcccaatga gggtgagatt                                               20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ggaatttccc actctttgtt                                               20
```

MAMMALIAN MULTIPOTENT STEM CELLS AND COMPOSITIONS, METHODS OF PREPARATION AND METHODS OF ADMINISTRATION THEREOF

RELATED APPLICATIONS

This application is a continuation of U.S. Ser. No. 12/644,425 filed Dec. 22, 2009 now U.S. Pat. No. 8,192,732 which is a continuation of U.S. Ser. No. 10/345,126 filed Jan. 14, 2003 now U.S. Pat. No. 7,635,467 and is related to U.S. Provisional Patent Applications, Ser. No. 60/348,473, filed Jan. 14, 2002, and Ser. No. 60/357,783, filed Feb. 19, 2002, and Ser. No. 60/376,257, filed Apr. 29, 2002, and Ser. No. 60/381,138, filed May 8, 2002, and Ser. No. 60/404,361, filed Aug. 19, 2002, and Ser. No. 60/430,381, filed Dec. 2, 2002, the disclosures of each of which are expressly incorporated by reference herein.

BACKGROUND OF THE INVENTION

1. Field of the Invention

This invention relates to novel mammalian multipotent stem cells (MSCs), compositions thereof, and methods of preparing and administering these cells. In one aspect, the invention relates to methods of making more developmentally potent cells from less developmentally potent cells. In another aspect, the invention relates to cells prepared according to the methods of the invention. In another aspect, the invention relates to pharmaceutical compositions comprising the more developmentally potent cells of the invention. In another aspect, the invention relates to cellular preparations for cell or tissue regeneration comprising said more developmentally potent cells of the invention. In another aspect, the invention relates to methods for regenerating cells or tissue comprising the step of administering the more developmentally potent cells of the invention to a tissue in an animal in need thereof. In another aspect, the invention relates to a method for treating a human or animal having a neurological or corporal deficit comprising the step of administering the more developmentally potent cells of the invention or terminally differentiated cells produced according to the invention to an animal, including human, in need thereof. In another aspect, the invention relates to a method of making and using a terminally differentiated cell utilizing the more developmentally potent cells of the invention. In another aspect, the invention relates to a method of changing the phenotype of a cell.

2. Background of the Related Art

Stem cells are often defined as self-renewing and multipotent, with the ability to generate diverse types of differentiated cells. As such, they show promise in the treatment of neurological and corporal deficits, or any loss or diminishment of tissue function due to age, disease, trauma or other factor. However, such treatments have faced significant hurdles that have yet to be substantially overcome.

NSCs and Neurological Deficits

Because one important focus of stem cell replacement therapies has been neurological disorders, neural stem cells, and particularly fetal neural stem cells, have been a major research target. During development of the central nervous system (CNS), multipotent neural stem cells (MNSCs), also known as neural stem cells (NSCs), proliferate, giving rise to transiently dividing progenitor cells that eventually differentiate into the cell types that compose the adult brain, including neurons, astrocytes and oligodendrocytes. NSCs have been isolated from several mammalian species, including mice, rats, pigs and humans. See, e.g., International Application, Publication Nos. WO 93/01275, WO 94/09119, WO 94/10292, WO 94/16718 and Cattaneo et al., 1996, *Mol. Brain. Res.* 42: 161-66. NSCs from the embryonic and adult rodent central nervous system (CNS) have been isolated and further propagated in vitro in a variety of culture systems. See, e.g., Frolichsthal-Schoeller et al., 1999, *NeuroReport* 10: 345-351; Doetsch et al., 1999, *Cell* 97: 703-716. NSCs from the human fetal brain have been cultured using serum-free medium supplemented with epidermal growth factor (EGF) and/or basic fibroblast growth factor (bFGF). See, e.g., Svendsen et al., 1998, *J. Neuroscience Methods* 85: 141-152; Carpenter et al., 1999, *Experimental Neurology* 158: 265-278. NSCs cultured utilizing these serum-free, mitogen-supplemented methods generally form substantially undifferentiated, clustered aggregates. Upon removal of the mitogen(s) and provision of a substrate, the stem cells differentiate into neurons, astrocytes and oligodendrocytes.

While the synaptic connections involved in neural circuits are continuously altered throughout the life of the individual, due to synaptic plasticity and cell death, neurogenesis, the generation of new neurons, was thought to be complete early in the postnatal period. The discovery of MNSCs in the adult brain (see, e.g., Alvarez-Buylla et al., 1997, *J. Neurobiology* 33: 585-601; Gould et al., 1999, *Science* 286: 548-552) has brought significant changes in the theory on neurogenesis as the presence of MNSCs in the adult brain suggests that regeneration of neurons can occur throughout life. Nevertheless, age, physical and biological trauma or neurodegenerative disease-associated loss of brain function, herein referred to as a "neurological deficit," can far outweigh any potential restorative effects due to endogenous neurogenesis. As a result, transplantation of NSCs is a potentially valuable treatment for those suffering from the loss of, or loss of appropriate, brain function due to age, physical and biological trauma or neurodegenerative disease (i.e., a neurological deficit).

Due to the advancing average age of the population, and concomitantly increased incidence of neurological deficit that accompanies advancing age, treatment of neurodegenerative diseases has become a major concern. Such diseases, including Alzheimer's disease, Huntington's chorea and Parkinson's disease, have been linked to neuronal degeneration at specific locations in the brain, leading to the inability of the brain region to synthesize and release neurotransmitters that are vital to neuronal signaling.

Neurodegeneration also encompasses many conditions and diseases, age-related or not, that result in neuronal loss. These conditions include CNS trauma, such as stroke and epilepsy, as well as diseases that result in neuronal loss, including amyotrophic lateral sclerosis and cerebral palsy.

Degeneration in a brain region known as the basal ganglia can lead to diseases with varied and different cognitive and motor symptoms, depending on the exact location of the lesion. The basal ganglia consists of many separate regions, including the striatum (which consists of the caudate and putamen), the globus pallidus, the substantia nigra, substantia innominata, ventral pallidum, nucleus basalis of Meynert, ventral tegmental area and the subthalamic nucleus.

Degeneration in the basal ganglia can lead to motor deficits. For example, Huntington's chorea is associated with degeneration of neurons in the striatum, which leads to involuntary jerking movements. Degeneration of a small region called the subthalamic nucleus is associated with violent flinging movements of the extremities in a condition called ballismus, while degeneration in the putamen and globus pallidus are associated with a condition of slow writhing movements or athetosis. In Parkinson's disease, degeneration is seen in another area of the basal ganglia, the substantia nigra par compacta. This area normally sends dopaminergic dopinergic? connections to the dorsal striatum, which are is? important in regulating movement. Therapy for Parkinson's disease has centered upon restoring dopaminergic activity to this circuit.

Alzheimer's disease patients exhibit a profound cellular degeneration of the forebrain and cerebral cortex. Further, a localized area of the basal ganglia, the nucleus basalis of Meynert, appears to be selectively degenerated. This nucleus normally sends cholinergic projections to the cerebral cortex that are thought to participate in cognitive functions including memory.

The objective of most CNS therapies is to regain the particular chemical function or enzymatic activity lost due to cellular degeneration. Administration of pharmaceutical compositions has been the main treatment for CNS dysfunction. Unfortunately, this type of treatment has many complications, including the limited ability to transport drugs across the blood-brain barrier, and drug-tolerance acquired by patients to whom these drugs are administered for long periods.

Transplantation of multipotent stem cells may avert the need not only for constant drug administration, but also for complicated drug delivery systems necessitated by the blood-brain barrier. In practice, however, significant limitations have been found in this technique as well. First, cells used for transplantation that carry cell surface molecules of a differentiated cell from a donor can induce an immune reaction in the recipient, a problem that is exacerbated by the physical damage caused by injection of cells directly into the affected area of the brain. In addition, the neural stem cells must be at a developmental stage where they are able to form normal neural connections with neighboring cells. For these reasons, initial studies on neurotransplantation centered on the use of fetal cells.

Mammalian fetal brain tissue has proven to have reasonable survival characteristics upon immediate transplantation. Increased survival capability of fetal neurons is thought to be due to the reduced susceptibility of fetal neurons to anoxia compared to adult neurons. An additional factor favoring survival of fetal cells is the lack of cell surface markers on fetal cells, whose presence may lead to rejection of grafted tissue from adults. However, although the brain is considered an immunologically privileged site, some rejection of even fetal tissue can occur. Therefore, the ability to use heterologous fetal tissue is limited by tissue rejection and the need for immunosuppressant drugs.

The use of large quantities of aborted fetal tissue presents other difficulties as well. Fetal CNS tissue is composed of more than one cell type, and thus is not a well-defined tissue source. In addition, there are doubts as to whether an adequate and constant supply of fetal tissue would be available for transplantation. For example, in the treatment of MPTP-induced Parkinsonism, tissue from as many as 6 to 8 fetuses can be required for successful implantation into the brain of a single patient. There is also the added problem of the potential for contamination during fetal tissue preparation. Since these tissue may already be infected with a bacteria or virus, expensive diagnostic testing is required for each fetus used. Even comprehensive diagnostic testing might not uncover all infected tissue. For example, there can be no guarantee that a sample is HIV-free, because antibodies to the virus are generally not present until several weeks after infection.

In addition to fetal tissue, there are other potential sources of tissue for neurotransplantation, including cell lines and genetically engineered cell types, but both sources present problems. Cell lines are immortalized cells that are derived, inter alia, by transformation of normal cells with an oncogene or by the culturing of cells in vitro with altered growth characteristics. Moreover, adverse immune response potential, the use of retroviruses to immortalize cells, the potential for the reversion of these cells to an amitotic state, and the lack of response by these cells to normal growth-inhibiting signals make such cell lines sub-optimal for widespread use. Likewise, xenobiotic transplantation has lacked significant success.

Another approach to neurotransplantation involves the use of genetically engineered cell types or gene therapy. However, there still exists a risk of inducing an immune reaction with these cells. In addition, retrovirus mediated transfer may result in other cellular abnormalities. Also, cell lines produced by retrovirus-mediated gene transfer have been shown to gradually inactivate their transferred genes following transplantation and further may also not achieve normal neuronal connections with the host tissue.

While currently available transplantation approaches represent an improvement over other available treatments for neurological disorders, they suffer from significant drawbacks. The inability in the prior art of the transplant to fully integrate into the host tissue, and the lack of availability of suitable cells in unlimited amounts from a reliable source for grafting are significant limitations of neurotransplantation. Studies utilizing intra-tissue injection of dissociated and partially differentiated NSCs have shown little promise (see, e.g., Benninger et al., 2000, *Brain Pathol.* 10: 330-341; Blakemore et al. 2000, *Cell Transplant* 9: 289-294; Rosser et al., 2000, *Eur. J. Neurosci.* 12: 2405-2413; Rubio et al., 2000, *Mol. Cell. Neurosci.* 16: 1-13). The results have generally been poor because, among many considerations, the dissociation of clusters of NSCs is known to cause immediate senescence of the NSCs and increase the vulnerability of NSCs in culture. See, e.g., Svendsen et al., 1998, *J. Neurosci. Methods* 85: 141-152. Further, regardless of adverse immune responses due to foreign tissue being introduced into the brain, the trauma caused by the physical introduction of cells directly into the damaged area can induce the recruitment of immune cells by the host that can eliminate the transplanted cells. Thus, significant problems with the use of NSCs to ameliorate neurological deficits remain.

As described herein, neurological deficits also include non-brain tissues such as, for example, the eye and spinal cord. In addition, corporal deficits are a target for amelioration utilizing multipotent stem cells. A "corporal deficit" is a disorder caused by a wide variety of diseases and injuries, resulting in trauma, malfunction, degeneration or loss of muscle such as, for example, cardiac muscle due to myocardial infarction. Other examples include malfunction, degeneration or loss of other cells and tissues apart from those discussed in the neurological deficit section above such as, for example, internal organs. For example, liver function can be adversely affected by, among other things, disease (e.g., cirrhosis or hepatitis), trauma or age. The problems described above in using NSCs to remedy neurological deficits of the brain also apply to neurological deficits in other tissues, such as the eye, and corporal deficits.

There exists a need in the art for improved methods for introducing multipotent stem cells to diseased, aged or damaged mammalian brain. In addition, there remains a need for methods of using or administering the multipotent stem cells of the invention, or pharmaceutical preparations thereof, to the affected, damaged or degenerated tissue, wherein the stem cells can differentiate in a manner appropriate for the host tissue and enable the replacement of damaged cells, repair of damages tissue and, optionally, amelioration of functional loss. There also remains a need in the art for a reliable source of unlimited numbers of cells for transplantation, particularly cells that are specifically adapted for and capable of proliferation, migration, and differentiation in mammalian brain or other tissues when introduced thereto. Furthermore, there exists a need in the art for methods for repairing damaged neural and other tissues in as non-invasive a fashion as possible, especially by inducing multipotent stem cells to proliferate and differentiate in vivo into, for example, neurons, astrocytes, and oligodendrocytes in the brain or, for example, rod or cone photoreceptor cells, horizontal cells, bipolar cells, amacrine cells, ganglion cells, Muller cells, and nerve cells, Buchs, chorid and retinal pigment epithelium (RPE) cells in eye tissue.

SUMMARY OF THE INVENTION

This invention provides methods for producing multipotent stem cells, and cells produced by those methods. In particular, the invention provides reagents and methods for efficiently producing stem cells that can be re-introduced into an animal in need thereof to alleviate neurological disorders.

In a first aspect, the invention provides methods for making a more developmentally potent cell from a less developmentally potent cell. In one embodiment, the method comprises the step of contacting a less developmentally potent cell with an effective amount of a substituted deoxynucleotide or deoxynucleoside compound for an effective period, wherein the substituted deoxynucleotide or deoxynucleoside compound-contacted, less developmentally potent cell becomes a more developmentally potent cell capable of differentiating to a less developmentally potent cell of its lineage of origin or a different lineage. In certain embodiments, the inventive methods further comprise the step of co-culturing the less developmentally potent cell contacted with substituted deoxynucleotide or deoxynucleoside compounds with neural-lineage cells or media conditioned with neural-lineage cells, wherein the substituted deoxynucleotide or deoxynucleoside compound-contacted, less developmentally potent cell becomes a more developmentally potent cell capable of differentiating to a less developmentally potent cell of its lineage of origin or a different lineage. In additional embodiments, the method comprises the step of contacting the less developmentally potent cell with a substituted deoxynucleotide or deoxynucleoside compound in an uncoated flask or a flask that has been treated to repel the cells. In yet further embodiments, the less developmentally potent cell is further contacted with a growth factor such as fibroblast growth factor, epidermal growth factor or a combination thereof. Alternatively, the less developmentally potent cells are contacted additionally with heparin.

Exemplary substituted deoxynucleotide or deoxynucleoside compounds as provided by the invention include but are not limited to halogen-substituted (halo-substituted) deoxynucleotides or deoxynucleosides, such as, for example, bromodeoxyuridine, iododeoxyuridine, bromodeoxyguanosine, iododeoxycytosine as well as alkyl-substituted species such as, for example, methyldeoxythymidine. A most preferred species is bromodeoxyuridine (BrdU). In certain embodiments, the less developmentally potent cell is contacted with an effective amount of substituted deoxynucleotide or deoxynucleoside compounds for an effective period. In some embodiments, the less developmentally potent cell is a tissue (or tissue-specific) stem cell, such as a hematopoietic stem cell, a neural stem cell, an epithelial stem cell, an epidermal stem cell, a retinal stem cell, an adipose stem cell and a mesenchymal stem cell. In certain embodiments, the less developmentally potent cell is obtained from any tissue containing stem cells including but not limited to zygote, blastocyst, embryo, fetus, infant juvenile or adult, and optionally, a human species of any of the preceding embodiments, whether naturally occurring or engineered. As provided herein, the methods of the invention provide one or a plurality of more developmentally potent cells that exist singly or form clusters of two or more cells.

In the practice of this aspect of the invention, the phenotype of the less developmentally potent cell is changed when it becomes a more developmentally potent cell. Thus, the invention provides methods for changing a first phenotype of a less developmentally potent cell into a second phenotype of more developmentally potent cell, wherein said second phenotype is determined by the environment surrounding the substituted deoxynucleotide or deoxynucleoside-contacted cell. In preferred embodiments, the less developmentally potent cell is a stem cell, more preferably a hematopoietic stem cell, a neural stem cell, an epithelial stem cell, an epidermal stem cell, a retinal stem cell, an adipose stem cell and a mesenchymal stem cell.

In a second aspect, the invention provides one or a plurality of more developmentally potent cells using the methods of the invention. In certain embodiments, the cells form a cluster of two or more cells. As provided herein, said more developmentally potent cells preferably comprise less than about 50 percent, more preferably less than about 25 percent, even more preferably less than about 10 percent, even more preferably less than about 5 percent, and even more preferably less than about 1 percent redifferentiated cells. "Redifferentiated cells" as used herein, refers to cells that have terminally differentiated during the performance of the methods herein prior to migration, differentiation and incorporation into host tissue.

In yet further aspects of the invention are provided pharmaceutical compositions comprising said more developmentally potent cells prepared according to the methods of the invention and a pharmaceutically-acceptable carrier or excipient. The invention provides such pharmaceutical compositions comprising said more developmentally potent cells that are tissue stem cells for use in cell or tissue regeneration or for correcting a disease or disorder in a tissue or animal in need thereof.

Thus, the invention also provides methods for using the pharmaceutical compositions provided herein to treat an animal in need thereof by administering the more developmentally potent cells thereto. In certain preferred embodiments, the more developmentally potent cells comprise a cluster of two or more of the more developmentally potent cells. Preferably, the animal has a corporal or neurological deficit that can be treated or ameliorated by administration of said more developmentally potent cells, such as a deficit caused by a neurodegenerative disease, a traumatic injury, a neurotoxic injury, ischemia, a developmental disorder, a disorder affecting vision, an injury or disease of the spinal cord, a demyelinating disease, an autoimmune disease, an infection, an inflammatory disease, or corporal disease, disorder, injury, trauma, malfunction, degeneration or loss. In preferred embodiments, the one or plurality of more developmentally potent cells are capable of migrating to an area of tissue damage, differentiating in a tissue-specific manner and functioning in a manner that reduces the neurological or corporal deficit. As provided by the methods of the invention herein, the cells are administered by injecting one or a plurality of more developmentally potent cells with a syringe, inserting the more developmentally potent cells with a catheter or surgically implanting the more developmentally potent cells. In certain embodiments, the more developmentally potent cells are injected with a syringe into a body cavity that is fluidly-connected to the area of neurological or corporal deficit. In certain preferred embodiments, the body cavity is a brain ventricle. In other embodiments, the more developmentally potent cells are inserted with a catheter into a body cavity that is fluidly-connected to the area of neurological or corporal deficit. In certain preferred embodiments, the body cavity is a brain ventricle. In still further additional embodiments, the more developmentally potent cells are surgically implanted into a body cavity that is fluidly-connected to the area of neurological or corporal deficit. In certain preferred embodiments, the body cavity is a brain ventricle. The more developmentally potent cells can also alternatively be inserted using a syringe or catheter or surgically implanted directly at the site of the neurological or corporal deficit or systemically (e.g., intravenously).

Administration of the one or a plurality of more developmentally potent cells into an animal results in said cells differentiating into a terminally-differentiated cell. Thus, the invention provides methods for making a terminally-differentiated cell, comprising the step of administering the more developmentally potent cells of the invention into an animal in need thereof. As provided by the methods of the invention herein, the cells are administered by injecting the more developmentally potent cells with a syringe, inserting the more developmentally potent cells with a catheter or surgically implanting the more developmentally potent cells. In certain embodiments, the more developmentally potent cells are injected with a syringe into a body cavity that is fluidly-connected to the area of neurological or corporal deficit. In certain preferred embodiments, the body cavity is a brain ventricle. In other embodiments, the more developmentally potent cells are inserted with a catheter into a body cavity that is fluidly-connected to the area of neurological or corporal deficit. In certain preferred embodiments, the body cavity is a brain ventricle. In still further additional embodiments, the more developmentally potent cells are surgically implanted into a body cavity that is fluidly-connected to the area of neurological or corporal deficit. In certain preferred embodiments, the body cavity is a brain ventricle. The more developmentally potent cells can also alternatively be inserted using a syringe or catheter or surgically implanted directly at the site of the neurological or corporal deficit or systemically (e.g., intravenously).

In the practice of this aspect of the invention, the phenotype of the more developmentally potent cell is changed when it differentiates into a terminally-differentiated cell. Thus, the invention provides methods for changing a first phenotype of a more developmentally potent cell into a second phenotype of less developmentally potent, more preferably a terminally-differentiated cell. The method further provides a method for changing a developmental potential phenotype of a cell, comprising the steps of contacting a cell of a first developmental potential phenotype with an effective amount of substituted deoxynucleotide or deoxynucleoside for an effective period that causes the cell to change into a second developmental potential phenotype distinct from the first developmental potential phenotype, wherein said second developmental potential phenotype is determined by the environment surrounding the substituted deoxynucleotide or deoxynucleoside contacted cell. In certain embodiments, the cell of a first developmental potential phenotype can be a stem cell. In other embodiments, the cell of a first developmental potential phenotype can be a hematopoietic stem cell, a neural stem cell, an epithelial stem cell, an epidermal stem cell, a retinal stem cell, an adipose stem cell and a mesenchymal stem cell, in preferred embodiments a mesenchymal cell.

Alternatively, the invention provides a method of treating a patient having a neurological deficit or corporal deficit with terminally differentiated cells, that is, with cells that are terminally differentiated prior to administration. Such terminally differentiated cells can be administered at the site of neurological or corporal deficit or systemically, for example, intravenously.

In yet another embodiment, the invention relates to treating a stem cell, excluding those of neural origin, such that it is converted into a more developmentally potent cell, which enables it to differentiate into the various cell types found in eye tissue, inter alia, chorid, Buchs and retinal pigment epithelium cells, rod and cone photoreceptor cells, horizontal cells, bipolar neurons, amacrine, ganglion and optic nerve cells. These non-limiting, exemplary cell types found in eye tissue are collectively referred to as retinal cells. The methods comprising the step of contacting more developmentally potent cells of the invention with an effective amount of one or a combination of growth factor selected from the group consisting of TGF-b3, IGF-1 and CNTF for an effective period such that the growth factor-contacted cells can differentiate into retinal cells.

In another aspect, the invention provides a method of altering the migration and/or differentiation of endogenous or exogenous multipotent stem cells in a mammal by modulating the levels of APP and/or reelin in the mammal. In certain embodiments, the exogenous multipotent stem cells can be the more developmentally potent cells produced according to the methods of the invention. In certain other embodiments, the more developmentally potent cells are administered as part of the pharmaceutical compositions or the cellular preparations of the invention. In other embodiments, the amount of reelin in a mammal is altered by administration of reelin protein, a drug that alters reelin levels, or a vector that expresses reelin to the mammal. In still other embodiments, the amount of APP in a mammal is altered by administration of an anti-APP antibody, a drug that alters APP levels, a vector that expresses APP, or the APP protein to the mammal. In still other embodiments, reelin can be administered before, after or concurrently with the more developmentally potent cells of the invention. Similarly, in other embodiments, anti-sAPP antibody or s-APP (secreted APP) can be administered before, after or concurrently with the more developmentally potent cells of the invention. In related embodiments, the invention provides methods of altering the migration of endogenous or exogenous multipotent stem cells in a mammal by altering the amount or binding affinity of APP or reelin receptor in the mammal. Similarly, the invention provides a method of altering the differentiation of endogenous or exogenous multipotent stem cells in a mammal by altering the amount or binding affinity of APP receptor in the mammal.

In another aspect, the invention provides a method of making a differentiated cell-specific product comprising the steps of differentiating the more developmentally potent cells of the invention, in the presence of an effective amount of factors known to induce differentiation of the desired cell type and isolating the desired differentiated cell-specific product. In another embodiment, the invention provides a method of making an undifferentiated cell-specific product comprising the steps of propagating the more developmentally potent cells of the invention according to the methods of the invention and isolating the desired undifferentiated cell-specific product.

Thus, the invention advantageously provides novel mammalian multipotent stem cells, pharmaceutical compositions thereof, and methods of preparing and administering the cells. The invention also advantageously provides methods of altering the migration and/or differentiation of multipotent stem cells through the alteration of APP and reeling levels. Further, the invention advantageously provides methods of utilizing the methods and cells of the invention to produce biochemical products.

Specific embodiments of the present invention will become evident from the following more detailed description of certain preferred embodiments and the claims.

BRIEF DESCRIPTION OF THE DRAWINGS

FIG. 6 (II) shows the differentiation of MNSCs in the co-culture with oxidatively damaged SH-Sy5 human neuroblastoma: (from left to right) light gray bars=control (0.0 µM $H_2O_2$); medium gray bars=low $H_2O_2$ (0.01 µM); dark gray bars=medium $H_2O_2$ (0.03 µM); black bars=high $H_2O_2$ (0.1 µM).

DETAILED DESCRIPTION OF PREFERRED EMBODIMENTS

Figure 1:
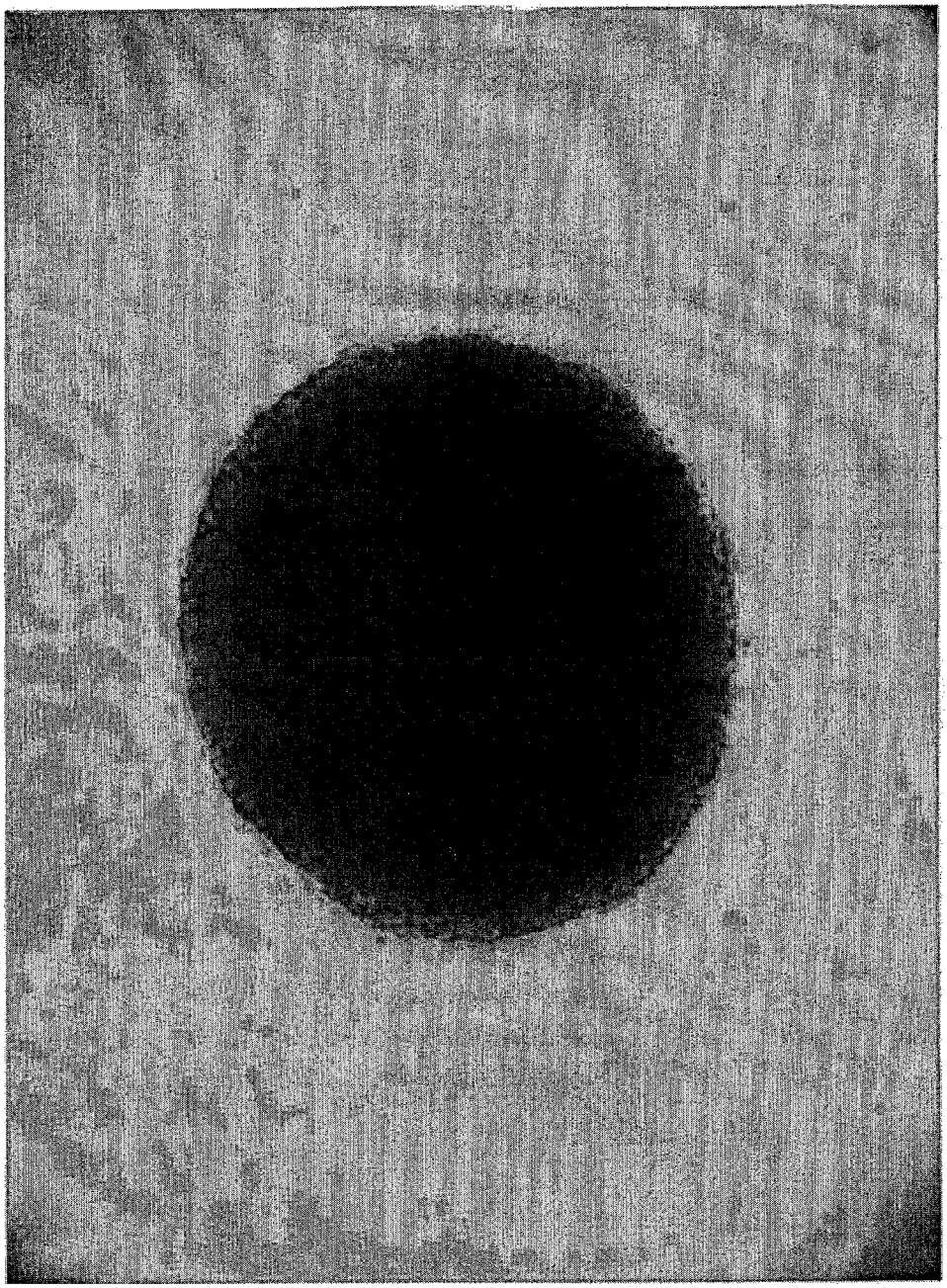
FIG. 1 shows a phase contrast photomicrograph of a floating, aggregated cluster of cells, characteristic of certain embodiments of the cells of the invention.

This invention provides more developmentally potent cells capable of differentiating in a tissue specific manner, particularly more developmentally potent cells that can be administered to an animal in need thereof.

As disclosed in further detail herein, the inventive methods provide for culturing less developmentally potent cells obtained, inter alia, from somatic tissue sources, and producing more developmentally potent cells therefrom. In one aspect, this effect is achieved by culturing the less developmentally potent cells in the presence of a substituted deoxynucleotide or deoxynucleoside compound. Exemplary substituted deoxynucleotide or deoxynucleoside compounds as provided by the invention include but are not limited to halogen-substituted (halo-substituted) deoxynucleotides or deoxynucleosides, such as, for example, bromodeoxyuridine, iododeoxyuridine, bromodeoxyguanosine, iododeoxycytosine as well as alkyl-substituted species such as, for example, methyldeoxythymidine. A most preferred species is bromodeoxyuridine (BrdU). BrdU is a thymidine analog that was originally produced for chemotherapy. It is known to regulate gene expression and cellular differentiation of some cell types. Since BrdU and other substituted deoxynucleotide or deoxynucleoside compounds, are incorporated into the nuclei of proliferating cells and are easy to detect by immunostaining, it has been used for detecting proliferating cells, such as stem cells; however, its biological effects on stem cells has not been appreciated, understood or disclosed in the art.

While adult stem cells continue to possess some multipotency, adult stem cells are limited by their tissue-specific character. As an example, human NSCs spontaneously differentiate into brain cells under basal media conditions, but MeSCs are essentially unable to spontaneously differentiate into neural cells without the addition of certain factors; in the context of the invention, such cells are less developmentally potent than cells that could differentiate into cells of two or more different lineages. These results indicate that each kind of tissue-specific stem cell contains specific information that allows it to become a special type of cell, i.e., they are partially committed to become a particular type of cell in a tissue-specific manner (i.e., less developmentally potent). To overcome this barrier of stem cell lineage and make cells that are more developmentally potent, alterations to the cells and their environment are necessary. The invention relates to methods of making more developmentally potent cells from less developmentally potent cells, as well as methods of treatment and use of the more developmentally potent cells, and the more developmentally potent cells themselves. As an example, the invention relates to the treatment of easily isolated and abundant stem cells like mesenchymal stem cells (i.e., a less developmentally potent cell) such that they are no longer constrained to differentiate into only mesenchymal-lineage cells such as osteocytes and chrondrocytes, among others. Treated according to the invention, the less developmentally potent mesenchymal stem cell becomes a more developmentally potent cell capable of differentiation into, for example, neural-lineage cells. The present invention also enables the use of autologous transplantation, which eliminates possibility of an immune reaction against a transplant of the more developmentally potent cells of the invention. For example, a patient's mesenchymal stem cells could be isolated, treated according to the methods of the invention, and transplanted back into the same patient to differentiate in a tissue-specific manner regardless the transplantation site, be it brain, eye, muscle, etc. Thus, the present invention provides a means to treat neurological and corporal deficits without the problems associated with heterologous transplants from adult or fetal sources.

As used herein, the terms "multipotent neural stem cells (MNSCs)," "neural stem cells (NSCs)" and "neural progenitor cells (NPCs)" refer to undifferentiated, multipotent cells of the CNS. Such terms are commonly used in the scientific literature. MNSCs can differentiate into tissue-specific cell types, for example astrocytes, oligodendrocytes, and neurons when transplanted in the brain. MNSCs of the invention are distinguished from natural MNSCs by their adaptation for proliferation, migration and differentiation in mammalian host tissue when introduced thereto.

As used herein, a "less developmentally potent cell" is a cell that is capable of limited multi-lineage differentiation or capable of single-lineage, tissue-specific differentiation, for example, an untreated mesenchymal stem cell can differentiate into, inter alia, osteocytes and chondrocytes, i.e., cells of mesenchymal lineage, but has only limited ability to differentiate into cells of other lineages (e.g., neural lineage.).

As used herein, a "more developmentally potent cell" is a cell that is readily capable of differentiating into a greater variety of cell types than its corresponding less developmentally potent cell. For example, a mesenchymal stem cell can readily differentiate into osteocytes and chondrocytes but has only limited ability to differentiate into neural or retinal lineage cells (i.e., it is a less developmentally potent cell in this context). Mesenchymal stem cells treated according to the methods of the invention become more developmentally potent because they can readily differentiate into, for example, mesenchymal-lineage and neural-lineage cell types; the plasticity of the cells is increased when treated according to the methods of the invention.

One or more of the more developmentally potent cells of the invention can propagate as separate cells and can also form a cluster of two or more cells. The clusters can comprise the progeny of a single more developmentally potent cell or clusters of primary cells.

As used herein, the terms "effective amount" and "therapeutically effective amount" each refer to the amount of reagent used to support the desired activity. In the case of more developmentally potent cells prepared and delivered according to the invention, an effective amount is an amount necessary to support an observable level of one or more biological activities of MSC as set forth herein. Regarding substituted deoxynucleotide or deoxynucleoside compounds, an effective amount can be between about 10 nanomolar and 100 micromolar, or more preferably between about 2 and 50 micromolar, or even more preferably about 10 micromolar. Regarding the method of making a retinal cell from the cells of the invention, an effective amount of TGF-b3, CNTF and IGF can be between about 1 ng/ml to 1 ug/ml, or more preferably between about 5 ng/ml to 500 ng/ml, or even more preferably between about 10 ng/ml to 100 ng/ml, or even more preferably about 50 ng/ml.

An "effective period" as used herein refers to the time period necessary for the reagents and cells of the invention to accomplish their specified activities. For example, less developmentally potent cells can be contacted with a substituted deoxynucleotide or deoxynucleoside compound for an effective period to make them more developmentally potent. An effective period for contact with a substituted deoxynucleotide or deoxynucleoside compound, as referred to herein, can be between 1 to 10 days, or more preferably between about 1 to 5 days, or even more preferably between about 2 to 3 days. Further, cells of the invention can be contacted before or during differentiation with TGF-b3, CNTF, IGF, or combinations thereof, for an effective period to make them capable of differentiating into retinal cells. An effective period for TGF-b3, CNTF and IGF contact, as referred to herein, can be between 1 to 10 days, or more preferably between about 1 to 7 days, or even more preferably between about 2 to 5 days.

The term "pharmaceutically acceptable carrier" or "physiologically acceptable carrier" as used herein refers to one or more formulation materials suitable for accomplishing or enhancing the successful delivery of the pharmaceutical composition of more developmentally potent cells prepared and delivered according to the invention.

As used herein, "ameliorating the effects caused by age, physical and biological trauma and degenerative disease" and the like refers to the diminution of the detrimental effects of damaged or degenerated tissue due to the use or administration of an effective amount of the more developmentally potent cells of the invention, or pharmaceutical preparations thereof, to the affected, damaged or degenerated tissue, wherein the stem cells can differentiate in a manner appropriate for the host tissue and enable the replacement of damaged cells, repair of damages tissue and reduction of structural or functional loss. For example, the neurological effects of events, diseases or processes that result in the loss of some degree of brain function or proper brain function. Such amelioration is affected through the administration to the animal of an effective amount of the more developmentally potent cells or pharmaceutical compositions thereof of the invention.

The invention also provides pharmaceutical compositions of the more developmentally potent cells of the invention and methods of delivery into the brain and other tissues thereof. The invention also provides methods of abating or remedying the effects of brain or other tissue disease or dysfunction caused by the loss of, or loss of appropriate, brain or other tissue function due to age, physical or biological trauma or neurodegenerative disease.

Cells can be obtained in many ways and from many tissues, for example, from donor tissue by dissociation of individual cells from the connecting extracellular matrix of the tissue or from commercial sources of NSCs (e.g., BioWhittaker, Walkersville, Md., CC-2599). For certain neural stem cell embodiments of the more developmentally potent cells of the invention, tissue from brain is removed using sterile procedures, and the cells are dissociated using any method known in the art including treatment with enzymes such as trypsin, collagenase and the like, or by using physical methods of dissociation such as mincing or treatment with a blunt instrument. Dissociation of neural cells, and other multipotent stem cells, can be carried out in tissue culture medium; in a preferred embodiment, the medium for dissociation of juvenile and adult cells is low calcium artificial cerebral spinal fluid (aCSF) having a formula identical to aCSF (124 mM NaCl, 5 mM KCl, 1.3 mM $MgCl_2$, 2 mM $CaCl_2$, 26 mM $NaHCO_3$, and 10 mM D-glucose) except that $MgCl_2$ is present at a concentration of 3.2 mM and $CaCl_2$ at a concentration of 0.1 mM. Dissociated cells are centrifuged at low speed, between 200 and 2000 rpm, usually between 400 and 800 rpm, the suspension medium is aspirated, and the cells are then resuspended in culture medium. Suspension cultures are preferred if large numbers of undifferentiated stem cell progeny are desired. Cell suspensions are seeded in any receptacle capable of sustaining cells, preferably uncoated flask or a flask that has been treated to repel the cells, culture plates or roller bottles that inhibit contact-dependent stem cell differentiation.

While isolation from brain tissue is feasible, mesenchymal stem cells from bone is a particularly good source of cells for use in generating more developmentally potent cells for use in the invention because isolation techniques are well established in the art (having been used for decades in immune disorder bone marrow transplants), and such techniques can be performed autologously. The patient's own mesenchymal stem cells can be isolated, treated according to the invention and readministered where necessary. In contrast, autologous transplants using a neural cell source is not particularly feasible.

Growth of more developmentally potent cells under the above culture conditions induces or permits these cells to form undifferentiated clusters of two or more cells (shown in FIG. 1). These clusters are optimally grown at a density of approximately 50 per T75 flask in 20 mL of the growth medium consisting of, for example, DMEM/HAMS F12 (at about 3:1; Gibco, BRL, Burlington, ON), supplemented with an antibiotic-antimycotic mixture (1:100, penicillin G, streptomycin sulfate, amphotericin B; Gibco), B27 (1:50, GIBCO), human recombinant FGF-2 and EGF (20 ng/ml each, R&D Systems, Minneapolis, Minn.) and heparin (5 μg/mL, Sigma, St. Louis, Mo.). The cultures are kept in a $CO_2$ incubator (about 5% $CO_2$) at 37° C. To facilitate optimal growth conditions, any clusters of two or more cells are sectioned into quarters approximately every 14 days and fed by replacing 50% of the medium approximately every 4-5 days. These conditions permit rapid and continual growth of NSCs, as well as the more or less developmentally potent cells of the invention, that can be expanded indefinitely while retaining their multipotent character. As with most eukaryotic cells, conditions for culturing should be as close as possible to physiological conditions. The pH of the culture medium should be close to physiological pH, preferably between pH 6-8, more preferably between about pH 7 to 7.8, with pH 7.4 being most preferred. Physiological temperatures range between about 30° C. to 40° C. Cells are preferably cultured at temperatures between about 32° C. to about 38° C., and more preferably between about 35° C. to about 37° C. Neural stem cells (NSCs) prepared and maintained as disclosed herein continue to exhibit multipotent character after more than three years of serum-free propagation. If in vitro differentiation is desired, the cells can be replated in culture dishes in, for example, serum-free basal medium Eagle (BME), which contains Earle's salt and L-glutamine. The cells can be cultured for about 5 days in the absence of FGF-2, EGF or other extrinsic differentiation factors. When induced to differentiate in this way, these cultured NSCs exhibit characteristic morphologies of neurons or astrocytes when immunohistochemically stained with b-III tubulin (a neuronal cell marker) or glial fibrillary acidic protein (GFAP, an astrocyte marker).

As disclosed above, the stem cell culture medium as used in the invention is preferably supplemented with at least one proliferation-inducing growth factor. A growth factor, as defined herein, refers to a protein, peptide or other molecule having a growth, proliferative, or trophic effect on the more or more developmentally potent cells and/or more or more developmentally potent cell progeny of the invention. Growth factors that are used for inducing proliferation include any trophic factor that allows more or more developmentally potent cells to proliferate, including any molecule that binds to a receptor on the surface of the cell to exert a trophic, or growth-inducing effect on the cell. Exemplary proliferation-inducing growth factors include epidermal growth factor (EGF), insulin-like growth factor (IGF), ciliary neurotrophic factor (CNTF), amphiregulin, acidic fibroblast growth factor (aFGF or FGF-1), basic fibroblast growth factor (bFGF or FGF-2), and combinations thereof. Preferred proliferation-inducing growth factors include EGF and FGF or a combination thereof. Growth factors are usually added to the culture medium at concentrations of between about 1 fg/mL to 1 mg/mL. Concentrations between about 1 to 100 ng/mL are usually sufficient. Simple titration experiments routine in the art are used to determine the optimal concentration of a particular growth factor for a particular cell culture.

Cells of the invention that are proliferated in serum-free media should be grown in the presence of a substituted deoxynucleotide or deoxynucleoside compounds such as, for example, halogenated-deoxynucleosides like bromodeoxyuridine (BrdU) or iododeoxyguanosine (IrdG), alkyl-substituted examples such as methyldeoxyguanosine prior to transplantation into a host. The pre-transplant growth medium comprises the components of the long-term propagation media, but also contains an effective amount of substituted deoxynucleotide or deoxynucleosides for use for an effective period. More developmentally potent cells prepared according to the methods of the invention are conditioned or adapted to proliferate, migrate and differentiate properly in the brain when transplanted into host tissue.

Cellular preparations and pharmaceutical compositions of the more developmentally potent cells of the invention are also provided herein. Pharmaceutical compositions optimally comprise a therapeutically effective amount of more developmentally potent cells in admixture with a pharmaceutically or physiologically acceptable formulation agent selected for suitability with the mode of administration. Acceptable formulation materials preferably are nontoxic to the more developmentally potent cells and the recipients at the dosages and concentrations employed.

The cellular preparations and pharmaceutical compositions of the invention may contain formulation materials for modifying, maintaining, or preserving, for example, pH, osmolarity, viscosity, clarity, color, isotonicity, odor, sterility, stability, rate of dissolution or release, adsorption, or penetration of the composition, as well as proliferation, migration and differentiation capacity of the more developmentally potent cells of the invention. Suitable formulation materials include, but are not limited to, amino acids (such as glycine, glutamine, asparagine, arginine, or lysine), antimicrobial compounds, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; trimethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See REMINGTON'S PHARMACEUTICAL SCIENCES (18th Ed., A. R. Gennaro, ed., Mack Publishing Company 1990).

The primary vehicle or carrier in a pharmaceutical composition may be either aqueous or non-aqueous in nature. For example, a suitable vehicle or carrier for injection may be water, physiological saline solution, or artificial cerebrospinal fluid. Optimal pharmaceutical compositions will be determined by a skilled artisan depending upon, for example, the intended route of administration, delivery format, desired dosage and recipient tissue. See, e.g., REMINGTON'S PHARMACEUTICAL SCIENCES, supra. Such compositions may influence the physical state, stability, and effectiveness of the MNSC composition.

The invention provides methods of delivery and transplantation of the more developmentally potent cells of the invention to ameliorate the effects of age, physical and biological trauma and degenerative disease on the brain or central nervous system of an animal, as well as other tissues such as, for example, retinal tissue. It is well recognized in the art that transplantation of tissue into the CNS offers the potential for treatment of neurodegenerative disorders and CNS damage due to injury. Transplantation of new cells into the damaged CNS has the potential to repair damaged circuitries and provide neurotransmitters thereby restoring neurological function. It is also recognized in the art that transplantation into other tissue, such as eye tissue, offers the potential for treatment of degenerative disorders and tissue damage due to injury. As disclosed herein, the invention provides methods for generating more developmentally potent cells adapted for proliferation, migration and differentiation in mammalian tissue when introduced thereto. The use of more developmentally potent cells in the treatment of neurological disorders and CNS damage, as well as the use of more developmentally potent cells in the treatment of other tissue damage or degeneration, can be demonstrated by the use of established animal models known in the art.

More developmentally potent cells of the invention can be administered to an animal with abnormal or degenerative symptoms obtained in any manner, including those obtained as a result of age, physical or biological trauma, or neurodegenerative disease and the like, or animal models created by man using recombinant genetic techniques, such as transgenic and "gene knockout" animals.

Recipients of the more developmentally potent cells of the invention can be immunosuppressed, either through the use of immunosuppressive drugs such as cyclosporin, or through local immunosuppression strategies employing locally applied immunosuppressants, but such immunosuppression need not necessarily be a prerequisite in certain immunoprivileged tissues such as, for example, brain and eye tissues. In certain embodiments, the delivery method of the invention can cause less localized tissue damage to the site of cell damage or malfunction than existing methods of delivery.

More developmentally potent cells of the invention can be prepared from the recipient's own tissue. In such instances, the progeny of the more developmentally potent cells can be generated from dissociated or isolated tissue and proliferated in vitro using the methods described herein. In the case of mesenchymal stem cells (MeSCs), progeny can be generated from MeSCs isolated from, for example, bone marrow. Upon suitable expansion of cell numbers, the stem cells of the invention can be harvested and readied for administration into the recipient's affected tissue.

There are significant differences in the method of delivery to the brain of the more developmentally potent cells compared to the prior art. One exemplary difference is as follows: the more developmentally potent cells of the invention are transplanted intraventricularly. Further, while the transplantation of one or more separate more developmentally potent cells is efficacious, the more developmentally potent cells of the invention are preferably transplanted in the form of clusters of two or more cells via a surgical procedure or injection using a syringe large enough to leave the clusters substantially intact. The results disclosed in the Examples below indicate that ventricular delivery of more developmentally potent cells of the invention in the form of a cluster of two or more cells can result in migration to the area of damage in the brain and proper neuronal differentiation. Another benefit of intraventricular injection is less tissue destruction, resulting in less localized recruitment of immune cells by the host. This is evidenced by the lack of ventricular distortion, tumor formation, and increased host astrocyte staining without any immunosuppression.

The method of delivery of the more developmentally potent cells of the invention to the brain can be essentially duplicated for other immunoprivileged tissue such as, for example, the eye. Delivery of one or more separate or two or more of the more developmentally potent cells in the form of a cluster via injection using a syringe large enough to leave the any cluster of two or more cells that is present substantially intact can result in migration to the area of damage in the eye and proper tissue-specific differentiation.

There are examples in the art of intra-tissue injection (brain) of dissociated and partially differentiated NSCs (see, e.g., Benninger et al., 2000, *Brain Pathol.* 10: 330-341; Blakemore et al., 2000, *Cell Transplant.* 9: 289-294; Rosser et al., 2000, *Eur. J. Neurosci.* 12: 2405-2413; Rubio et al., 2000, *Mol. Cell. Neurosci.* 16: 1-13). Further, the dissociation of NSC neurospheres is known to cause immediate senescence of NSCs and increase the vulnerability of NSCs in culture. See, e.g., Svendsen et al., 1998, *J. Neurosci. Methods* 85: 141-152. Some aspects of the instant invention preferentially employ injection of clusters of two or more cells, but the more developmentally potent cells of the invention appear to migrate and differentiate appropriately when transplanted in non-cluster from as well. As provided by this invention, intraventricular transplantation provides an alternative route to the site-specific injection disclosed in the prior art. Using intraventricular transplantation, grafted cells can gain access to various structures by the flow of CSF, and transplantation of more developmentally potent cells of the invention in cluster form can act to prevent premature differentiation at inappropriate anatomical sites in the brain and central nervous system. Regarding the eye, intraocular administration of clusters of two or more cells, for example into the vitreous fluid, allows the more developmentally potent cells of the invention to migrate to the area of degeneration or injury and differentiate appropriately.

Delivery of more developmentally potent cells of the invention into other, non-immunoprivileged tissues can also be carried out, particularly when the more developmentally potent cells are autologous to the recipient.

Figure 2:
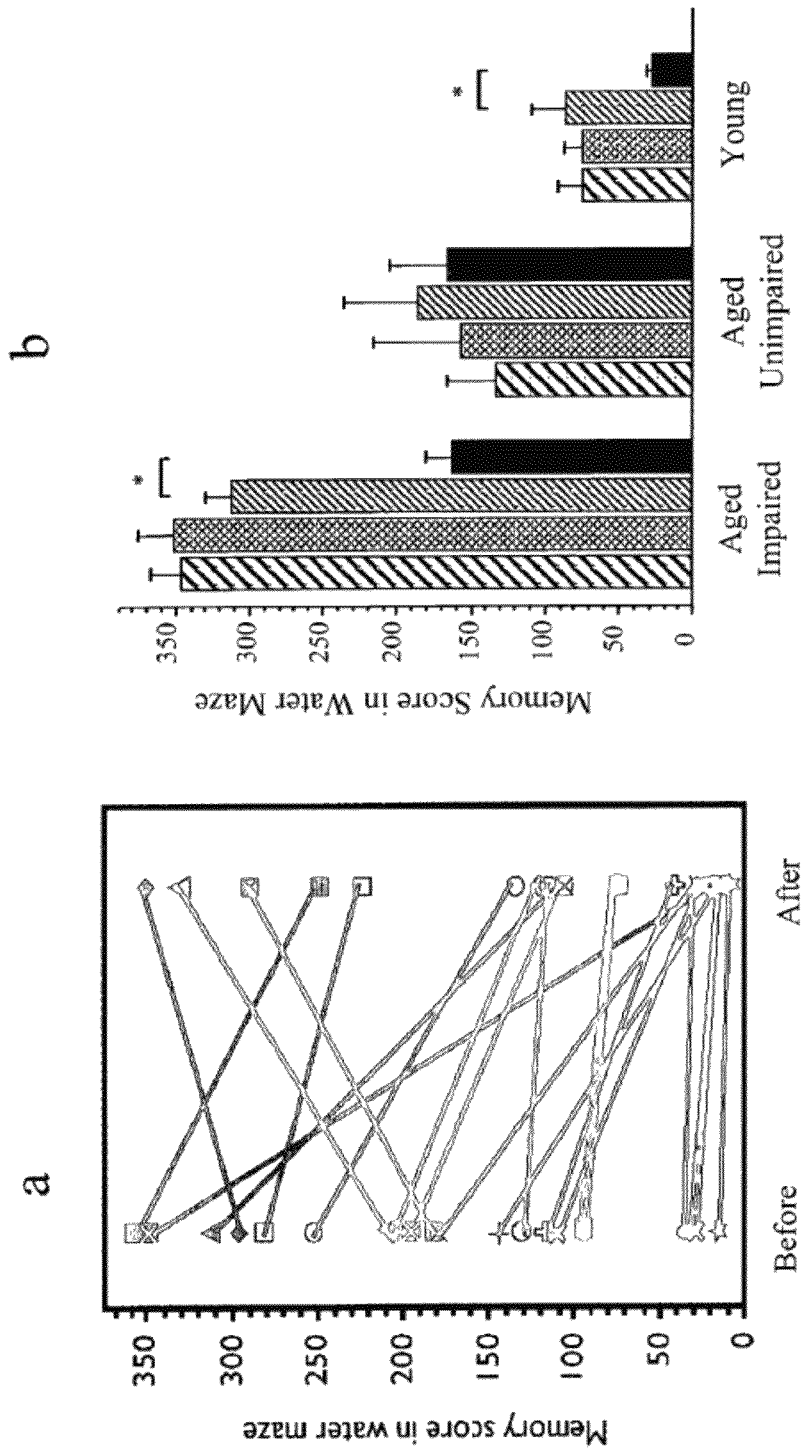
FIG. 2 shows the effect of MNSC transplantation on memory score in the Morris water maze test. (a) Individual memory score before and after transplantation shows improvement in the majority of the animals. Blue: Aged memory impaired animals, Green: Aged memory unimpaired animals, Red: Matured animals. (b) Mean of memory score in each animal group before (narrow striped bar) and after (black bar) MNSCs transplantation shows a significant improvement in aged memory impaired and young animals. The animals that received vehicle injection do not show significant difference in memory score between before (wide striped bar) and after (hatched) the injection.

Functional integration of the graft into the host's neural tissue can be assessed by examining the effectiveness of grafts on restoring various functions, including but not limited to tests for endocrine, motor, cognitive and sensory functions. Useful motor tests include tests that quantitate rotational movement away from the degenerated side of the brain, and tests that quantitate slowness of movement, balance, coordination, akinesia or lack of movement, rigidity and tremors. Cognitive tests include tests of the ability to perform everyday tasks, as well as various memory tests, including maze performance such as the Morris water maze performance. For example, using the cells and methods of the invention, more developmentally potent cells injected into the ventricle of 24-month-old rats after in vitro expansion displayed extensive and positional incorporation into the aged host brain with improvement of cognitive score (FIG. 2), as assessed by the Morris water maze after 4 weeks of the transplantation. Results of the experiments disclosed herein indicate that the aged brain is capable of providing the necessary environment for more developmentally potent cells of the invention to retain their multipotent status and demonstrate the potential for neuroreplacement therapies in age associated neurodegenerative disease.

Figure 3:
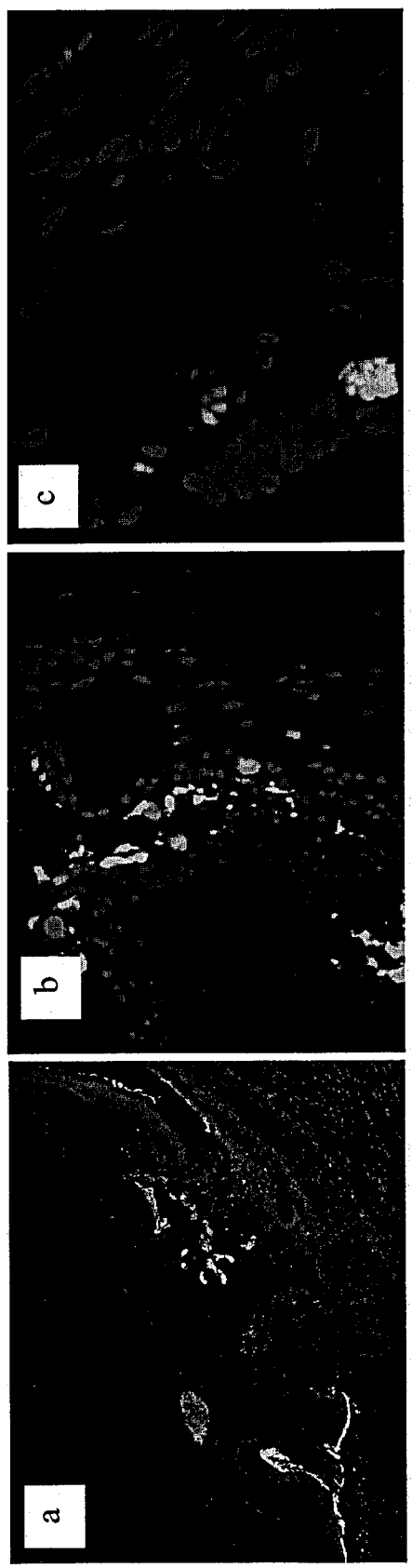
FIG. 3 shows differentiation of MeSCs into retinal cells in vivo. All nuclei were counterstained by DAPI (blue). (a) Typical immunocytochemistry of retinal sections 4 weeks after a lesion and transplantation of MeSC of the invention (×100). The section was double-immunofluorescence stained with BrdU (red) and opsin (green) markers for donor cells and photoreceptor cells, respectively. MeSCs of the invention migrated into damaged area of the retinal tissue. A higher magnification (b, ×400) shows that these migrating MeSCs also show cytosolic expression of opsin. (c) Typical in situ hybridization histochemistry (×100) for human opsin gene expression using human-specific opsin sequence riboprobes (green). Incorporation of human opsin positive cells to the rat retinal tissue is observed.

Functional integration of the graft into the host's other tissue can be assessed by examining the effectiveness of grafts on restoring various functions specific to the injured or degenerated tissue, for example improvement in sight for transplantation of stem cells of the invention to the eye. Regarding the eye, using the cells and methods of the invention, more developmentally potent cells of the invention injected into the vitreous cavity of rat eyes after in vitro expansion displayed extensive and positional incorporation into the host eye tissue (FIG. 3) 4 weeks post-transplantation. Results of the experiments disclosed herein indicate that the eye, as with the brain, is capable of providing the necessary environment for the more developmentally potent cells of the invention to differentiate in a tissue-specific manner, and thus demonstrate the potential for replacement therapies in injury or degeneration-associated tissue damage.

Figure 4:
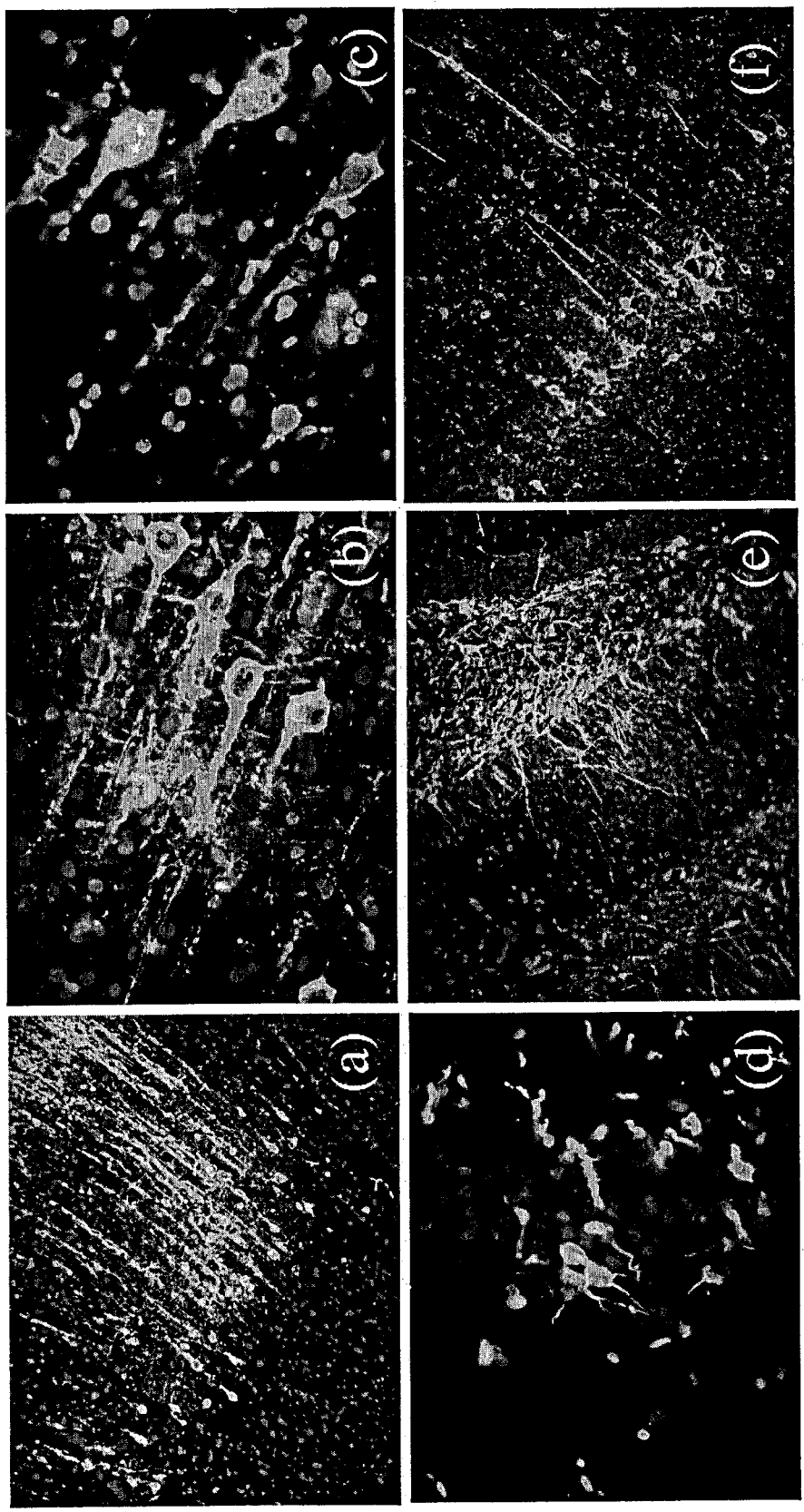
FIG. 4 shows typical fluorescent immunohistochemical photomicrographs of aged rat brain 30 days after MNSCs transplantation. bIII-tubulin and GFAP immunoreactivity were used as markers for neuron and glia, respectively. (a) MNSCs of the invention migrated into the cortex and differentiated into neurons as indicated by the bIII-tubulin positive cells (green), which have morphologies typical of pyramidal cells in layer IV and V of the parietal cortex. Apical dendrites were pointed towards to the edge of the cortex. Since the MNSCs were pre-treated with BrdU, the transplanted cells have BrdU positive nuclei (red). Contrarily, the host cell's nuclei are counter stained with DAPI (blue). Many cells having BrdU positive nuclei are observed with bIII-tubulin immunoreactivity in layer II and without bIII-tubulin immunoreactivity in layer III. (b, c) Higher magnification of the parietal cortex in cortex layer IV: All the bIII-tubulin immunoreactive (green) positive cells show BrdU (red) positive nuclei while many other host cell's nuclei are stained with only DAPI (blue). MNSCs tend to have larger nuclei than host cells. (d) MNSCs migrated into the hippocampus and differentiated into bIII-tubulin positive cells (green), in CA1 pyramidal cell layer. These bIII-tubulin positive cells have BrdU positive nuclei (red), indicating that these cells originated from transplanted cells. In contrast, host cell nuclei counter stained with DAPI (blue) are not bIII-tubulin positive. (e) In the dentate gyrus many fibers were bIII-tubulin positive in addition to the bIII-tubulin positive cells (green) and GFAP positive cells (red). (f) bIII-tubulin positive cells (green) and GFAP positive cells (red) were found in layer IV and layer III, respectively. such a layer of astrocytes were not observed in normal rats without MNSC transplantation.

Without being restricted to any particular theory for the mechanism of action of the cells and methods of the invention, there are at least two explanations for the beneficial effects of more developmentally potent cell transplantation to cognitive function of the host brain as well as the beneficial effects of more developmentally potent cell transplantation in other tissues. One is replacement or augmentation. Neuronal circuits can be replaced or augmented by the more developmentally potent cell-derived neurons. In other tissues, cells and cell structures can also be replaced or augmented by more developmentally potent cell-derived cells appropriate for that tissue. An alternative explanation is the trophic action of factors released from the transplanted more developmentally potent cells. Morphological analysis of rat brains transplanted with the more developmentally potent cells as disclosed herein showed extensive incorporation of the more developmentally potent cells and massive growth of neuronal fibers in the host brain area related to spatial memory task (FIGS. 4 and 5); however, the more developmentally potent cells may still migrate toward the damaged neurons and rescue them by the production of neurotrophic factors. Synergy between these two explanations may also exist.

As assessed by the Morris water maze test, improvement in spatial memory of more developmentally potent cell-transplanted animals was accompanied by incorporation of the more developmentally potent cells into the brain areas known to be related to spatial memory. The post-transplant morphology of rat brain tissue indicates that functional association of the transplanted cells to the host brain occurs. Immunohistochemical analysis revealed that the bIII-tubulin-positive donor-derived cells found in the cerebral cortex are characterized by having dendrites pointing to the edge of the cortex whereas in the hippocampus, donor-derived neurons exhibited morphologies with multiple processes and branches. These differential morphologies of the transplanted more developmentally potent cells in different brain regions indicate that site-specific differentiation of the more developmentally potent cells occurs according to various factors present in each brain region.

Strong astrocyte staining was also found in the frontal cortex layer 3 and CA2 region of hippocampus in transplanted rat brains, areas where astrocytes are not normally present in the animal. The migration of the more developmentally potent cells to the CA2 is of particular interest because CA2 pyramidal neurons highly express bFGF, and the expression of bFGF is up-regulated by entorhinal cortex lesions (see, e.g., Eckenstein et al., 1994, *Biochem. Pharmacol.* 47: 103-110; Gonzalez et al., 1995, *Brain Res.* 701: 201-226; Williams et al., 1996, *J. Comp. Neurol.* 370: 147-158). CA2 pyramidal neurons in the host brain can express bFGF as a response to a reduction of synaptic transmission, an event that can occur during aging. Subsequently, this expressed bFGF can act as a signal for the transplanted more developmentally potent cells to respond, migrate or proliferate under the influence of bFGF produced in the host brain after the transplantation.

The regions rich in astrocyte staining in transplanted rat brains are the same regions where extensively stained neuronal fibers were identified (FIGS. 4a, 4d and 4e). During development, glial cells have many complex functions, such as neuronal and axonal guidance and production of trophic factors (see, e.g., Pundt et al., 1995, *Brain Res.* 695: 25-36). This overlapping distribution of glial and neuronal fibers strongly suggests that this interaction plays a pivotal role in survival, migration, and differentiation of transplanted more developmentally potent cells.

Immunohistochemistry of transplanted rat brains reveals a symmetrical distribution of neurons and astrocytes at both sides of the host brain, indicating that the progeny of these more developmentally potent cells can migrate. Although astrocytes have been shown to migrate over long distances following transplantation (see, e.g., Blakemore et al., 1991, *Trends Neurosci.* 14: 323-327; Hatton et al., 1992, *Glia* 5: 251-258; Lundberg et al., 1996, *Exp. Neurol.* 139: 39-53), there is experimental evidence showing that neurons do not migrate as widely as glial cells (see, e.g., Fricker et al., 1999, *J. Neurosci.* 19: 5990-6005). As disclosed herein, neuronal precursors derived from the more developmentally potent cells of the invention possess similar migratory capacity to astrocyte precursors.

Bioreactor

The use of biocatalyst for the production of useful products has been a part of man's history for thousands of years. Until this century the production of useful products from biocatalysts was performed in batch-type reactors (fermenters). Numerous newer, more efficient methods utilizing bioreactors are used to regulate important growth parameters such as, for example, pH, oxygen, sterility, nutrition. The basic economics behind biological production are two-fold: producing a product with greater value than the raw material it was derived from and producing a product that cannot be economically made in any other way, in both cases for the purpose of satisfying market demand.

For bulk biochemical production, such as beer, the principle costs are in the initial raw materials and initial capital costs for the production facility since millions of gallons of beer must be produced to obtain a reasonable return on the investment. It should also be noted that yields of these products are some of the highest of any biologically derived products.

At the other extreme is high-value biochemical production, such as monoclonal antibody, whose largest expense is in the downstream processing of the product. This can occur because the difficulty of obtaining certain biological starting materials as well as other reasons such as federal regulations stipulating the purity of the final product if it is to be used in vivo. In this situation, however, the very small amount of product produced and the difficulty in performing the production requires that the final product be sold at many orders of magnitude higher than the bulk biochemical for the same basic quantity. In certain circumstances, the cost of obtaining critical materials for biochemical production can be so prohibitive that such production is not economically feasible. Further, some materials are simply not available at any cost, so methods enabling the conversion of more easily obtained (or obtainable at all) materials into that critical material can be extremely valuable.

The methods of the invention make possible the conversion of easily obtainable less developmentally potent cells, for example MeSCs, to more developmentally potent cells, cells that can be subsequently differentiated in vitro to the desired, and possibly difficult to obtain, cell type for use as a bioreactor for the production of proteins or products specific to the differentiated cell. Differentiation can be induced through exposure of the cells of the invention to growth factors and supplements known in the art to be important in differentiation of the desired cell type. As described elsewhere herein, more developmentally potent cells of the invention of MeSC origin were induced to differentiate in vitro to cells of retinal origin through exposure to TGF-b3, CNTF, or IGF-1. Further, using the growth conditions described herein, the more and less developmentally potent cells themselves can be propagated long terms and used as bioreactors for production of proteins or products specific to those cells. The ability to easily isolate and propagate a potentially unlimited population of more developmentally potent cells that have the capacity to terminally differentiate into a desired cell type enables the biochemical production of heretofore unavailable or prohibitively expensive cellular products.

The methods of the invention also make personalized drug screening much more feasible, both technically and monetarily. Easily obtained less developmentally potent cells such as MeSCs, can be treated according to the methods of the invention and induced to a cell type appropriate for the testing of a particular drug. For example, neurally differentiated cells have been used as an experimental system for drugs that act on the brain. While NSCs can be commercially obtained, they are not specific to any particular person and are thus useless for personalized drug efficacy testing. Using the methods of the invention, a person's less developmentally potent cells, for example MeSCs isolated using minimally invasive methods well established in the art, can be converted into more developmentally potent cells that can be differentiated into, for example, cells of neural origin and utilized for testing. Such methods can be used to determine the effect of drugs on, for example, expression levels of particular genes induced by particular drugs for a particular patient. Such information can be critical in determining appropriate or inappropriate reactions, at a biochemical level, to a drug, which can be critical information for any drug with the potential for undesired, and often dangerous or fatal, effects.

As the more developmentally potent cells of the invention can mimic neural stem cells in many regards, relevant information pertaining to neural stem cells is presented, followed by information pertaining to mesenchymal and retinal stem cells. One of skill in the art will readily recognize the methods of the invention are not limited to these three types of stem cells and instead extend to cover all cell types not yet terminally differentiated.

Neural-Related

Due to the generally low proliferation rate of mammalian NSCs, there is a correlation between advancing age and impaired brain function even in the absence of specific neurodegenerative disease or physical or biological brain trauma. The invention provides methods for counteracting impaired brain function due to advancing age through the addition of more developmentally potent cells capable of proliferation, migration and differentiation in mammalian brain when introduced thereto.

Physical trauma and biological trauma are additional causes of impaired or improper brain function. The term "physical trauma" denotes brain cell damage due to external sources such as blunt head trauma, severe concussion and the like. Such physical trauma can be localized or general depending on the source and severity of the trauma. The term "biological trauma" denotes any acute brain injury that has its origin in a biological process, for example, stroke, aneurysm, epilepsy, brain tumor, hypoxia and the like.

Another source of impaired or improper brain function is neurodegenerative disease. In recent years neurodegenerative disease has become an important concern due to an expanding elderly population that is at greatest risk for these disorders. Neurodegenerative diseases include, but are not limited Alzheimer's disease, amyotrophic lateral sclerosis (ALS), Parkinson's disease, Pick's disease, Huntington's disease, progressive supranuclear palsy, corticobasal degeneration, Parkinson-ALS-dementia complex, Gerstmann-Straussler-Scheinker syndrome, Hallervorden-Spatz disease, Kufs' disease, Wilson's disease, multiple sclerosis (MS), late-onset metachromatic leukodystrophy and adrenoleukodystrophy. The effects of these diseases can be counteracted by administration of the more developmentally potent cells of the invention.

There are a variety of organic brain diseases that impair motor or cognitive function. Degeneration in the basal ganglia can lead to diseases with cognitive and motor symptoms, depending on the exact location of the degeneration. Motor deficits are a common result of degeneration in the basal ganglia. Huntington's Chorea is associated with the degeneration of neurons in the striatum, which leads to involuntary jerking movements in the host. Degeneration of a small region called the subthalamic nucleus is associated with violent flinging movements of the extremities in a condition called ballismus, while degeneration in the putamen and globus pallidus is associated with a condition of slow writhing movements or athetosis. In Parkinson's disease, degeneration is seen in another area of the basal ganglia, the substantia nigra par compacta. This area normally sends dopaminergic connections to the dorsal striatum, which are important in regulating movement. Therapy for Parkinson's disease has centered upon restoring dopaminergic activity to this circuit, which can be accomplished by transplantation of more developmentally potent cells to this region of the brain according to the instant invention.

In Alzheimer's disease, another neurodegenerative disease, there is substantial cellular degeneration of the forebrain and cerebral cortex. Further, a localized area of the basal ganglia, the nucleus basalis of Meynert, appears to be selectively degenerated. This nucleus normally sends cholinergic projections to the cerebral cortex, which are thought to participate in cognitive functions including memory.

Mesenchymal Related

Although adult stem cells continue to possess some multipotency, cell types produced from adult stem cells are limited by their tissue-specific character. For example, human NSCs spontaneously differentiate into brain cells under basal media conditions, but MeSCs are essentially unable to readily and spontaneously differentiate into neural cells without the addition of certain factors; in the context of the invention, such cells are less developmentally potent than cells that could differentiate into cells of two or more different lineages. These results indicate that each kind of tissue-specific stem cell contains specific information that allows it to become a special type of cell, i.e., they are partially committed to become a particular type of cell in a tissue-specific manner (i.e., less developmentally potent). To overcome this barrier of stem cell lineage and make cells that are more developmentally potent, alterations to the cells and their environment are necessary. However, the exact regulation mechanisms of tissue-specific stem cell fate decisions remain unclear. This knowledge base gap poses an important problem, because although MeSCs are rather easy to isolate from bone marrow and to proliferate in culture, they are essentially unable to readily differentiate into NSCs or other non-mesenchymal-lineage cells. Although the potential therapeutic use of MeSCs in the central nervous system has been discussed, technologies to induce neural lineage in MeSCs had not been fully established prior to the instant invention.

MeSCs of the invention can serve as an alternative to NSCs for potential therapeutic use utilizing the methods of the invention, which exploit the capacity of substituted deoxynucleotide or deoxynucleoside species, such as BrdU, to prime the MeSCs, i.e., remove them from their restricted mesenchymal differentiation path to the neural stem cell-like (or other lineage) differentiation path. MeSCs were successfully differentiated into neurons and glia in vitro and in vivo using the substituted deoxynucleotide or deoxynucleoside pretreatment of the invention. Thus, MeSCs of the invention can serve as an alternative to NSCs for potential therapeutic use in neuroreplacement utilizing the methods of the invention.

These cells are important in the neuroreplacement therapy field because their production permits autologous transplantation. Stem cells can be isolated from the patient, expanded in vitro, genetically modified if desired or necessary and transplanted back to the same patient. Since neural stem cells can be differentiated into most peripheral tissue cells, the invention is not only useful to neuroreplacement but to other kinds of tissue regeneration or replacement as well. In addition, since the cells originate from the patient, there are no ethical barriers or immunorejection issues with which to contend.

Retinal Related

Retinal degenerative diseases, including macular degeneration, are major causes of blindness. Despite investigations into gene therapy, growth/survival factor injections and vitamin treatments, no effective vision-restoring treatments are currently available. Visual impairment caused by the degeneration of photoreceptors or neural cells has been considered incurable because of a long-held "truism" that neurons do not regenerate during adulthood. However, this statement has been challenged and there is new evidence that these cells do indeed have the potential to be renewed after maturation, thus opening a door for the development of novel therapies to treat visual impairment by retinal regeneration using stem cell transplantation.

The capacity for retinal regeneration in cold-blooded vertebrates has long been recognized. Fish and amphibians continue to make new retinal neurons through a population of retinal stem cells residing at the peripheral margin of the retina, the so-called "ciliary marginal zone." Recent studies have provided evidence that birds and adult mammals also possess a zone of cells at the retinal margin analogous to the ciliary marginal zone of cold-blooded vertebrates. These retinal stem cells are reported not only to generate photoreceptor and other retinal cells in vitro, but also to differentiate into retinal cells following transplantation into the retinal area. Although these results indicate the possibility of retinal regeneration therapy, an alternative source of stem cells is required for clinical applications because the number of retinal stem cells is limited.

Neural stem cells have been isolated from embryonic and adult mammalian brains and have been propagated in vitro in a variety of culture systems. Using a serum-free unsupplemented media condition, NSCs spontaneously differentiated into bIII-tubulin-, glial fibrillary acidic protein (GFAP)-, and O4-immunopositive cells, markers for neurons, astrocytes, and oligodendrocytes, respectively. As described in the Examples below, NSCs treated according to methods of the invention migrate and differentiate into neurons and glia after transplantation into the brains of 24-month-old rats and significantly improved the cognitive functions of these animals. This result suggested that more developmentally potent cells produced according to the invention could provide transplantable material to produce a retinal stem cell alternative.

There is a variety of factors involved in the development of retinal tissue that regulate the proliferation and differentiation of retinal cells. Transforming growth factor beta-3 (TGF-b3) is thought to regulate cell proliferation during development and also influence the commitment or the differentiation, or both, of neural progenitor cells to retinal fates. Treatment of embryonic day-18 rat retinal cultures with TGF beta-like protein, activin A, causes the progenitor cells in these cultures to exit the cell cycle and differentiate into rod photoreceptors, indicating that the TGF-family is an important regulator of photoreceptor differentiation in the developing retina. Treatment of the more developmentally potent cells prepared according to the invention with an effective amount of growth factor selected from the group consisting of TGF-b3, IGF-1 and CNTF, for an effective period, can induce their adoption of a retinal differentiation path. That is, more developmemtally potent cells of the invention, regardless their origin, can be made to adopt a retinal differentiation path. Cells not treated according to the methods of the invention do not so differentiate with simple exposure to these growth factors. Using the methods of the invention, less developmentally potent cells can be transformed into more developmentally potent cells and subsequently used as alternatives to retinal stem cells to repair ocular tissue damage or promote tissue regeneration As described above, "retinal differentiation," as used herein, refers to the various cell types found in eye tissue, inter alia, chorid, Buchs and retinal pigment epithelium cells, rod and cone photoreceptor cells, horizontal cells, bipolar neurons, amacrine, ganglion and optic nerve cells. These non-limiting, exemplary cell types found in eye tissue are collectively referred to as retinal cells.

The inventive methods use substituted deoxynucleotide or deoxynucleoside compounds to change the cell fate decisions of less developmentally potent cells to more developmentally potent cells. In the case of retinal transplants, these more developmentally potent cells are treated with an effective amount of growth factor selected from the group consisting of TGF-b3, IGF-1 and CNTF, for an effective period to encourage their commitment change to the retinal cell lineage.

There are a variety of neurological and corporal deficits that can be addressed using the more developmentally potent cells of the invention.

"Neurological Deficits" Amenable to Treatment Because the invention relates in part to the discovery that multipotent precursor cells can be stimulated to divide and migrate through the brain, such MSCs can be used to treat neurological deficits caused by a wide variety of diseases, disorders, and injuries. These insults include, but are not limited to, the following.

Degenerative Diseases

Degenerative diseases that can be treated according to the methods of the invention include Alzheimer's disease (AD), Parkinson's disease (PD), Huntington's disease (HD), Pick's disease, progressive supranuclear palsy (PSP), striatonigral degeneration, cortico-basal degeneration, childhood disintegrative disorder, olivopontocerebellar atrophy (OPCA; including a heritable form), Leigh's disease, infantile necrotizing encephalomyelopathy, Hunter's disease, mucopolysaccharidosis, various leukodystrophies (such as Krabbe's disease, Pelizaeus-Merzbacher disease, and the like), amaurotic (familial) idiocy, Kufs disease, Spielmayer-Vogt disease, Tay Sachs disease, Batten disease, Jansky-Bielschowsky disease, Reye's disease, cerebral ataxia, chronic alcoholism, beriberi, Hallervorden-Spatz syndrome, and cerebellar degeneration.

Traumatic and Neurotoxic Injuries to the Central Nervous System

Traumatic and neurotoxic injuries that can be treated according to the methods of the invention include gunshot wounds, injuries caused by blunt force, injuries caused by penetration injuries (e.g., stab wounds), injuries caused in the course of a surgical procedure (e.g., to remove a tumor or abscess from the CNS or to treat epilepsy), poisoning (e.g., with MPTP or carbon monoxide), shaken-baby syndrome, adverse reactions to medication (including idiosyncratic reactions), drug overdose (e.g., from amphetamines), and post-traumatic encephalopathy.

Ischemia

Any disruption of blood flow or oxygen delivery to the nervous system can injure or kill cells, including neurons and glial cells, therein. These injuries can be treated according to the methods of the present invention and include injuries caused by a stroke (including a global stroke (as may result from cardiac arrest, arrhythmia, or myocardial infarction) or a focal stroke (as may result from a thrombus, embolus, hemorrhage, or other arterial blockage)), anoxia, hypoxia, partial drowning, myoclonus, severe smoke inhalation, dystonias (including heritable dystonias), and acquired hydrocephalus.

Developmental Disorders

Developmental disorders that can be treated according to the methods of the invention include schizophrenia, certain forms of severe mental retardation, cerebral palsy (whether caused by infection, anoxia, premature birth, blood type incompatibility: etc. and whether manifest as blindness, deafness, retardation, motor skill deficit, etc.), congenital hydrocephalus, metabolic disorders affecting the CNS, severe autism, Down Syndrome, LHRH/hypothalamic disorder, and spina bifida.

Disorders Affecting Vision

Disorders affecting vision, particularly those caused by the loss or failure of retinal cells, can be treated according to the methods and cells of the invention. These disorders include, for example, diabetic retinopathy, serious retinal detachment, retinal damage associated with glaucoma, traumatic injury to the retina, retinal vascular occlusion, macular degeneration (wet or dry), post-surgical healing, tumor, heritable retinal dystrophies, optic nerve atrophy, and other retinal degenerative diseases. Cells targeted for repair utilizing cells and methods of the invention include, for example, choroids, Buchs, retinal pigment epithelial (RPE), rods, cones, horizontal cells, bipolar neurons, amacrine, ganglion, and optic nerve.

Injuries and Diseases of the Spinal Cord

Injuries to or diseases affecting the spinal cord can also be treated according to the methods of the invention. Such injuries or diseases include post-polio syndrome, amyotrophic lateral sclerosis, nonspecified spinal degeneration, traumatic injury (such as those caused by automobile or sporting accidents), including any injury that crushes, partially severs, completely severs, or otherwise adversely affects the function of cells in the spinal cord), injuries caused by surgery to the spinal cord (e.g., to remove a tumor), anterior horn cell disease, and paralytic diseases.

Demyelinating or Autoimmune Disorders

Neurological deficits caused by demyelination or an autoimmune response can be treated according to the methods of the invention. Such deficits can be caused by multiple sclerosis, or lupus.

Infectious or Inflammatory Diseases

Neurological deficits caused by an infection or inflammatory disease can be treated according to the methods of the invention. Infections or inflammatory diseases that can cause treatable deficits include Creutzfeldt-Jacob disease and other slow virus infectious diseases, AIDS encephalopathy, post-encephalitic Parkinsonism, viral encephalitis, bacterial meningitis and meningitis caused by other organisms, phlebitis and thrombophlebitis of intracranial venous sinuses, syphilitic Parkinsonism, and tuberculosis of the CNS.

In addition to the deficits, diseases and disorders set forth explicitly above, those of ordinary skill in the art are well able to recognize neurological deficits, regardless of their cause, and to apply the methods of the present invention to treat patients who have such deficits. In addition to the conditions listed above, that are amenable to treatment with the methods described herein, neurological deficits can be caused by Lesch-Nyhan syndrome, myasthenia gravis, various dementias, numerous parasitic diseases, and epilepsy. Further, alleviation of age-related memory loss is an object of the invention. The methods of the invention can be readily applied to alleviate neurological deficits caused by these and other diseases, disorders, or injuries.

"Corporal Deficits" Amenable to Treatment

The invention also relates to the amelioration of corporal deficits utilizing multipotent precursor cells stimulated to divide, migrate through damaged tissue and differentiate in a tissue-specific manner. Cells according to the invention can be used to treat corporal deficits caused by a wide variety of diseases, disorders, and injuries, the result of which is trauma, malfunction, degeneration or loss of muscle such as, for example, cardiac muscle due to myocardial infarction. Other examples include malfunction, degeneration or loss of other cells and tissues apart from those discussed in the neurological deficit section above such as, for example, internal organs. For example, liver function can be adversely affected by, among other things, disease (e.g., cirrhosis or hepatitis), trauma or age. Other exemplary internal organs amenable to treatment utilizing the embodiments of the invention include heart, pancreas, kidney, stomach, and lung. Corporal deficits also comprise malfunction, degeneration or loss of skeletal assets such as, for example, vertebrae.

Reelin and Amyloid Precursor Protein (APP)

Reelin

Neurogenesis in animals lacking the more developmentally potent cells of the present invention is dependent on endogenous NSCs. Islands of NSCs have been detected in embryonic and adult mammalian brains, and due to their pluripotent differentiation potential, they can differentiate into astrocytes, neurons, or oligodendrocytes. Recent studies have observed NSCs in the anterior subventricular zone (SVZ) and dentate gyrus of the adult brain, indicating that neurogenesis may occur throughout life. Although pluripotency of endogenous, adult NSCs is regionally and temporally restricted, these cells retain their ability to migrate and differentiate in response to environmental cues. As described in Example 1 below, human NSCs that were injected into the lateral ventricle of 24-month-old rats showed a symmetrical migration in the host brain followed by differentiation into neurons and glial cells. This result indicates that the aged brain maintains regulatory mechanisms to guide the migration of NSCs, and exogenous more developmentally potent cells of the invention, that may be indispensable for proper adult brain neuroplasticity.

Recent studies (Corbin et al., 2001, *Nat Neurosci* 4 *Supp.* 1: 1177-827; Marin et al., 2001, *Nat Rev Neurosci* 2: 780-901) have revealed two distinct neuronal migration patterns: radial and tangential. Each pattern consists of two different neuronal populations that participate in corticogenesis. One neuronal population proliferates from the embryonic SVZ and migrates along the radial glia to reach the subcortical plate, detaches from radial glia scaffolding, and then penetrates the subcortical plate guided by reelin gradient secreted by gamma amino butyric acid (GABA)-ergic Cajal-Retzius cells (D'Arcangelo et al., 1995, *Nature* 374: 719-23). A second neuronal population consists of tangentially migrating neuroblasts that proliferate in the SVZ in the mantle of ganglionic telencephalic eminences and give rise to GABA-producing interneurons (Anderson et al., 2001, *Development* 128: 353-63). In the adult brain, host glial cells respond to the transplantation of NSCs (Leavitt et al., 1999, *Exp. Neurol* 157: 43-57) and lesions (Yang et al., 1997, *Exp Neurol* 146: 199-205) by becoming transient radial glia-type cells, which may serve to guide migration in adult neurogenesis. In contrast, subsets of cells expressed in the ventral piriform cortex and olfactory bulb migrate long distances without a radial glia connection (Durbec et al., 2001, *Mol Cell Neurosci* 17: 561-76), suggesting that specific regulatory mechanisms guide NSC migration in the adult brain and that some of these mechanisms are very likely analogous to those operative during development.

Reelin is a large extracellular matrix (ECM) protein of approximately 400 kDa, which binds to the a3 subunit of integrin receptors expressed on neuronal cell surfaces, very low density lipoprotein receptor (VLDLR) and Apolipoprotein E receptor 2 (ApoER2), triggering the adaptor function of the disabled-1 (Dab-1) cytosolic protein. The clustering of integrin receptor subunits following reelin binding activates a tyrosine kinase (focal adhesion kinase) to phosphorylate Dab-1. This phosphorylated Dab-1 binds and transports soluble tyrosine kinases and transcription factors to functional cellular compartments. In the null reeler mouse, migrating neurons fail to penetrate the subcortical plate, likely due to a deficiency of serine protease activity associated with reelin. While much attention has been focused on role of reelin in neuronal migration during corticogenesis, we now know that reelin is expressed in several neuronal populations in the adult brain (Pesold, C., et al., Proc Natl Acad Sci USA 95, 3221-6 (1998); Pesold, C., et al., Proc Natl Acad Sci USA 96, 3217-22 (1999)). This protein is thought to be operative in other important functions, for example, the reelin haploinsufficient heterozygous reeler mouse exhibits decreased dendritic spine expression density in pyramidal neurons of the cortex and hippocampus and reelin and alpha-3-integrin (a3-integrin) receptor subunit immunoreactivities colocalize to dendritic spine postsynaptic densitie, which supports a role for reelin in adult brain neuroplasticity (spine formation and synaptogenesis) that requires protein synthesis. Such studies draw a reasonable connection to the observation that depressed reelin levels have been observed in victims of schizophrenia and autism. Deficiencies in neuroplasticity and stem cell migration could be seen to reduce or prevent the endogenous stem cell population or exogenous, more developmentally potent cells of the invention from migrating to the regions of need in the brain.

Our studies indicate that reelin plays an important role in regulation of NSC biology. The addition of recombinant reelin to NSCs in culture increased mobility of cells in the cluster of cells that typified their growth. When NSCs were transplanted in the brain of reeler homozygous mice, mice that do not express reelin, migration was nearly halted; in contrast, NSCs migrated and displayed a beautifully symmetrical distribution in wild-type mice brain after transplantation. We found that only cells expressing reelin migrated into the cortex of reeler homozygous mice. These results suggest that reelin is an indispensable factor for the migration of NSCs or more developmentally potent cells of the invention, and the epigenetically downregulated reelin expression in schizophrenia and autism patients causes a deficit in migration and neuroplasticity potentially associated with those phenotypes. Reelin is preferentially expressed in GABAergic neurons in the adult cortex, so some of the loss of GABAergic interneurons in the neocortex of schizophrenia may be explained by this mechanism as well.

Mammals with suppressed reelin expression may not experience proper migration of endogenous or exogenous multipotent cells in the brain. Thus, reelin levels could be raised through genetic engineering approaches, i.e., the introduction of cells expressing reelin or appropriate vectors for endogenous cells transfection, to stimulate migration at the possible expense of some additional glial differentiation. The reelin protein can be administered to a mammal in need. For example, reelin can be introduced at the site of a stroke to encourage the migration of multipotent cells into the area of damage to start repair. Drugs that increase reelin expression or reelin levels in general may also be administered in an amount sufficient to raise reelin levels enough to enable proper migration. Similarly, the biological activity of the reelin present in an animal depends also on reelin receptor. Altering reelin receptor abundance or affinity for reelin can enhance the activity or suppress the activity of any reelin preset in the animal. The present invention contemplates the use genetic techniques to supplement or alter the natural supply of reelin receptors through genetic techniques well known in the art to influence cell migration. Similarly, the invention provides a method of altering the differentiation of endogenous or exogenous multipotent stem cells in a mammal by altering the amount or binding affinity of APP receptor in the mammal. Such methods may help those afflicted with schizophrenia and autism.

Thus the alteration of reelin levels may be used to influence the migration of endogenous NSCs as well as exogenous multipotent cells such as the more developmentally potent cells of the invention.

APP

While many factors are released following apoptotic cell death, several studies point to an important correlation between apoptosis and the amyloid precursor protein (APP). Damaged neurons and neurons committed to apoptosis demonstrate signals strongly immunopositive for APP. Moreover, amyloidgenic fragments produced from APP are released into the extracellular space from neuronal cells under serum-deprived conditions. The expression of APP is also reported to increase during retinoic acid-induced neuronal differentiation. The mRNA expression of beta-amyloid (b-amyloid) precursor-like proteins (APLP-1 and APLP-2) is also up-regulated during retinoic acid induced differentiation of human SH-SY5Y neuroblastoma cells. The increase in APP expression levels during neuronal differentiation in various cell culture systems suggests an important cellular function for APP during the differentiation process. From these observations, it appears that under serum-free differentiation conditions, APP fragments released from apoptotic cells serve as regulation and differentiation factors for neighboring stem cells.

APP is also known to be up-regulated during development and after brain damage, both of which are events that involve migration and differentiation of NSCs. Secreted APP (sAPP) has also been reported to produce protein kinase C and synaptogenesis in cultured neurons, in addition to significantly enhancing proliferation and growth of neural stem cells. Moreover, it has been shown that sAPP is able to activate MAPK (ERK) in PC12 cells via the Ras pathway. Since MAPK activation can induce proliferation or differentiation, sAPP may activate this pathway in proximal stem cells and induce cell differentiation. These facts, together with several of the examples below, indicate that one of APP's physiological functions may be the regulation of stem cell biology in the brain to allow for the successful formation and replacement of proper structures and neuronal circuits. sAPP released from damaged or dying cells may preferentially induce glial differentiation of a population of NSCs and this may act to reconstruct neuronal circuits by the guidance of NSCs to areas of damage. The stem cell-derived glial cells can then produce factors that can support surrounding damaged cells and promote neuronal migration and differentiation of other NSCs in this area. Our in vitro observations that the initial apoptotic cell death-induced glial differentiation was followed by neuronal differentiation (Brannen, C. L., et al., Neuroreport, 11, 1123-8 (2000)) supports this view. Thus, under normal physiologic conditions, APP can be necessary to recover from brain damage. In the case of familial AD, the increased levels of APP fragments produced in the brains of these patients may modify the biological equilibrium of NSCs in such a way that a pathological shift towards premature differentiation of NSCs will occur, thereby depleting or exhausting the NSC population. Since the effective natural replacement of degenerating neurons in the adult brain during aging or disease process may be important in maintaining normal brain function, the NSC population exhaustion would hinder such replacement.

In preliminary studies, we found evidence that APP fragments are secreted from apoptotic HNSCs and induce differentiation of other NSCs in vitro. We also observed that exogenously added secreted-type APP (sAPP) induces the differentiation of NSCs, while antibody recognizing the N-terminal of APP prevents the differentiation of NSCs. These findings indicate that APP signaling is one of the regulatory systems involved in the differentiation of NSCs. We also found that NSCs transplanted into the APP knockout mouse brain could not migrate properly and failed to repair brain lesions, whereas NSCs transplanted into wild-type mouse successfully migrated into the proper position and differentiated in a tissue-appropriate manner. This result is not only the first finding of a phenotypical change in APP-knockout mice, but also indicates a physiological role for APP in the regeneration of adult brain cells. Furthermore, we found that the addition of a higher concentration of sAPP or the over-expression of APP by transgenes to NSC cultures caused glial rather than neural differentiation of these cells. These findings indicate that the pathological alteration of APP metabolism in AD induces glial differentiation of neural stem cells and could leads to the exhaustion of the stem cell population, which may be important for ongoing neurogenesis in the adult brain.

To prevent or remedy any exhaustion of endogenous stem cell populations in the brain, more developmentally potent cells of the invention can be administered according to the methods of the invention to the mammal with increased APP production. Such action may act to overwhelm the excess APP such that increased glial differentiation of the multipotent cells is nevertheless accompanies with significant proper migration and differentiation to replace degenerating neurons. Alternatively, anti-APP antibody can be used to lower excessive APP levels. Anti-APP antibody can be administered to the mammal with overabundant APP such that the APP levels are reduced in an amount sufficient to prevent glial differentiation of the endogenous or exogenous multipotent stem cell population. Genetic engineering methods can be used to introduce a vector that expresses anti-APP antibody in the mammal with elevated APP levels. Such a method prevents the need for repeated administration of the antibody protein itself. Furthermore, drugs that lower APP expression or APP levels in general can be administered.

Mammals with suppressed APP expression may not experience proper migration of endogenous or exogenous multipotent cells in the brain. Thus, APP levels could be raised through genetic engineering approaches, the introduction of cells expressing APP or appropriate vectors for endogenous cells transfection, in some instances expressing at relatively low levels, to stimulate migration at the possible expense of some additional glial differentiation. The APP protein can be administered to a mammal in need. For example, APP can be introduced at the site of a stroke to encourage the migration of multipotent cells into the area of damage to start repair. Glial differentiation is an important part of the healing process in the brain. Drugs that increase APP expression or APP levels in general may also be administered in an amount sufficient to raise APP levels enough to enable proper migration.

As with reelin, the biological activity of the APP present in an animal depends also on APP receptor. Altering APP receptor abundance or affinity for APP can enhance the activity or suppress the activity of any APP preset in the animal. The present invention contemplates the use genetic techniques to supplement or alter the natural supply of APP receptors through genetic techniques well known in the art to influence cell migration and/or prolifaration.

Thus the alteration of APP levels may be used to influence the migration and differentiation of endogenous NSCs as well as exogenous multipotent cells such as the more developmentally potent cells of the invention.

An advantage of the cells of the invention is that they can be genetically engineered according to routine procedures known in the art (See, e.g., SAMBROOK, ET AL., MOLECULAR CLONING: A LABORATORY MANUAL. $3^{RD}$ EDITION, COLD SPRING HARBOR LABORATORY, 2001). As mentioned above, in preferred embodiments, constructs encoding reelin can be provided to the cells. In other preferred embodiments, constructs that inhibit expression of APP (such as ribozymes, antisense molecules, or other means of inhibiting APP expression) can be provided. In further embodiments, drug resistance genes and markers, or detectable markers such as GFP can be provided. Preferably, the marker and other genes are operably and genetically linked to gene expression regulatory elements (including but not limited to promoters and enhancers) that are operable in the terminally differentiated cell derived from MSCs of the invention or in the undifferentiated MSCs of the invention or both.

The following examples are presented in order to more fully illustrate the preferred embodiments of the invention. They should in no way be construed, however, as limiting the scope of the invention, as defined by the appended claims.

EXAMPLES

Example 1

Improvement of Cognitive Function in Aged Rat by the Transplantation of NSCs of the Invention Human NSCs do not require any exogenous factors for differentiation and survived more than three weeks in basal media without the addition of any factor to support their survival (Qu et al., 2001, *Neuroreport* 12: 1127-32). Thus, it appears that human NSCs produce factors to differentiate and support themselves, which suggested that these cells could be transplanted into aged animals after treatment according to the methods of the invention.

Human NSCs, expanded without differentiation under the influence of mitogenic factors in supplemented serum-free media and pre-treated by the incorporation of bromodeoxyuridine (BrdU) into the nuclear DNA, were injected into the lateral ventricle of mature (6-month-old) and aged (24-month-old) rats. Human NSCs prepared according to the methods of the invention survived 30 days after xenotransplantation into aged rat brain, while retaining both multipotency and migratory capacity, and also improved cognitive function in 24-month-old rats. Cognitive function of the animals was assessed by the Morris water maze both before and four weeks after the transplantation of human NSCs of the invention. Before human NSC transplantation, some aged animals (aged memory unimpaired animals) cognitively functioned in the range of mature animals, while others (aged memory impaired animals) functioned entirely out of the cognitive range of the mature animals. After transplantation of the BrdU-treated human NSCs, most aged animals had cognitive function in the range of the mature animals. Strikingly, one of the aged memory-impaired animals showed dramatic improvement in its behavior, functioning even better than the mature animals (FIG. 2a). Statistical analysis showed that cognitive function was significantly improved in both mature and aged memory-impaired animals but not in aged memory-unimpaired animals after BrdU-treated human NSC transplantation (FIG. 2b), which may be due to the physical limitations of the aged animals. The performance of three of the aged animals deteriorated in the water maze after transplantation of treated human NSCs. It is possible that the physical strength of these animals deteriorated during the experimental period.

These behavioral results indicate the beneficial effects of the transplantation of BrdU-treated human NSCs into the host brain. After the second water maze task, postmortem brains were further analyzed by immunohistochemistry for human bIII-tubulin and human GFAP, markers for neurons and astrocytes respectively. There was no sign of ventricular distortion, no evidence of tumor formation, and no strong host anti-graft immunoreactivity was observed as revealed by weak host astrocyte staining. Intensely and extensively stained with bIII-tubulin, neurons with BrdU-positive nuclei were found in bilateral singular and parietal cortexes (FIG. 4a-c) and hippocampus (FIG. 4d,e). The bIII-tubulin-positive neurons found in the cerebral cortex were typified by a dendrite pointing to the edge of the cortex. In the hippocampus, donor-derived neurons exhibited multiple morphologies, varying in cellular size and shape, and one or more processes and branching.

Generally, GFAP-positive astrocytes were localized near the area where neuronal cells were found. On further analysis (overlapping images of their distributions), donor-derived astrocytes were found to co-localize with neuronal fibers in the cortex (FIG. 4f). These astrocytes were larger than the host glia, with cell bodies 8-10 microns in diameter and thick processes. Some of these astrocytes had a unilateral morphology (asymmetric), and the immunostaining formed a thin ring around the nucleus, while the majority of the processes were formed on the other side. Most cells appeared a symmetrical with processes forming from all sides. The absence of this type of cell in normal animal without the transplantation of treated human NSCs was confirmed using immunohistochemistry for rat astrocytes. host astrocytes had small cell bodies with multiple delicate processes, and were distributed throughout the brain mainly in white matter and around the edges of the brain.

These results demonstrated that transplanted cells of the invention migrated in rat brain and differentiated into appropriate cell types. The concomitant improvement in cognitive function indicated that transplanted more developmentally potent cells of the invention were functionally integrated into the recipient brains.

The following methods were used in this and several of the following examples:

The Morris Water Maze:

The Morris water maze consists of a large circular tank (diameter, 183 cm; wall height, 58 cm), filled with water (27° C.) and opacified by the addition of powdered milk (0.9 kg). Beneath the water surface (1 cm) near the center of one of the four quadrants of the maze a clear escape platform (height, 34.5 cm) is positioned. The rats receive three training trials per day for seven consecutive days, using a 60 sec inter-trial interval. A training trial consists of placing the animal in the water for 90 seconds or until the swimming rat successfully locates the platform. If the rat fails to find the platform within the 90 seconds, the animal is gently guided to the platform. For spatial learning assessment, the platform's location remains constant in one quadrant of the maze, but the starting position for each trial is varied. Every sixth trial is a probe trial, during which the platform is retracted to the bottom of the pool for 30 sec and then raised and made available for escape. The training trials assess the acquisition and day-to-day retention of the spatial task while the probe tests are used to assess search strategy. At the completion of a spatial learning assessment, one session with six trials of cue training is performed Rats are trained to escape to a visible black platform that is raised 2 cm above the surface of the water. The location of the platform is varied from trial to trial to assess sensorimotor and motivational functioning independent of spatial learning ability. Each rat is given 30 seconds to reach the platform and is allowed to remain there briefly before the 30 second inter-trial interval. Accuracy of performance is assessed using a learning index score computed from the probe trials. The learning index is a derived measure from average proximity (cumulative search error divided by the length of the probe trial) on the second, third, and fourth interpolated probe trials. Scores from these trials are weighted and summed to provide an overall measure of spatial learning ability. Lower scores on the index indicate a more accurate search near the target location; higher scores indicate a more random search and poor learning.

Cell Migration and Differentiation:

In order to investigate differentiation and/or migration of cells of the invention in the brain, more developmentally potent cells were transplanted into rodent brain. The animals were anesthetized with 50 mg/kg pentobarbital (i.p.) and mounted in a stereotaxic apparatus (David Kopf). Approximately $1 \times 10^4$ to $1 \times 10^5$ cells in 5 μl phosphate-buffered saline were injected into the ventricle using a microsyringe attached to the stereotaxic apparatus. After removing the hair from the surgical site using electric razor, an iodine swab was be applied to the area and a 0.5 cm surgical incision was made caudal to rostral in the skin at the surface of the cranium. The ventricle was stereotaxically localized using the following exemplary coordinates: AP=−0.58 mm from bregma, ML=+1 mm, and 2.4 mm below dura (for mouse): AP=−1.4 mm from bregma, ML=+3.3 mm, and 4.5 mm below dura (for rat). A 0.4-mm hole was made in the cranium by careful drilling. The cells of the invention were injected into the ventricle using a microsyringe. The injection was delivered over a period of five minutes and the needle was left in place for an additional two minutes following the injection. After the injection, the surgically incised skin was closed by Michel suture clip (2.5× 1.75 mm). Ten days post-surgery, proper healing of the incision site was observed, and the Michel sutures were removed.

The existence and location of the cells of the invention after administration in rat brain was analyzed as follows. At 30 days post-transplantation, the rats were sacrificed by an overdose of sodium pentobarbital (70 mg/kg, i.p.) and perfused with phosphate buffered saline (PBS) followed by 4% paraformaldehyde. Brains were removed and incubated overnight in 4% paraformaldehyde fixative containing 20% sucrose. The brains were sliced into 20 micron coronal sections using a cryomicrotome. The sections were washed briefly in PBS and pretreated with 1M HCl for 30 minutes at room temperature and neutralized with sodium borate (0.1 M, pH 8.0) for 30 minutes in order to increase the accessibility of an anti-BrdU antibody to BrdU incorporated in the cell nuclei. After rinsing with PBS, sections were transferred to a solution containing 0.25% Triton X-100 in PBS (PBST) for 30 minutes. The sections were then blocked by incubation in PBST containing 3% donkey normal serum for 1 hour, followed by incubating the sections overnight at 48° C. with sheep anti-BrdU (1:1000; Jackson IR Laboratories, Inc. West Grove, Pa.) or mouse anti-BrdU (1:200; DSHB, Iowa City, Iowa) diluted in PBST. After rinsing the sections in PBS, donkey anti-mouse or donkey anti-sheep conjugated to rhodamine IgG (Jackson IR Laboratories, Inc.) was added at a 1:200 dilution in PBST and the sections further incubated for 2 hours at room temperature in the dark.

The transplanted cells of the invention, with BrdU immunopositive nuclei, were stained for human bIII-tubulin and human glial filament protein (GFAP). The sections were then washed with PBS and incubated with mouse IgG2b monoclonal anti-human bIII-tubulin, clone SDL3D10 (1:500, Sigma), goat antihuman GFAP, N-terminal human affinity purified (1:200, Research Diagnostics Inc., Flander, N.J.) or mouse IgG1 monoclonal anti-GFAP, clone G-A-5 (1:500, Sigma), respectively, overnight at 48° C. in the dark. After brief washing with PBS to remove excess primary antibody, the location of primary antibody binding was then determined using FITC-conjugated (Jackson IR Laboratories, Inc.) secondary antibody (donkey anti-mouse (1:200) or donkey anti-goat IgG (H+L; 1:200), respectively) by incubating the sections for 2 hours at room temperature in the dark.

The sections were then washed with PBS thoroughly before mounting to glass slides. The mounted sections were covered with Vectashield using 4',6-diamidine-2-phenylindole●2HCl (DAPI, Vector Laboratories, Inc., Burlingame, Calif.) for fluorescent microscopic observation. Microscopic images were taken by using an Axiocam digital camera mounted on the Axioscope 2 with Axiovision software (Zeiss).

Figure 5:
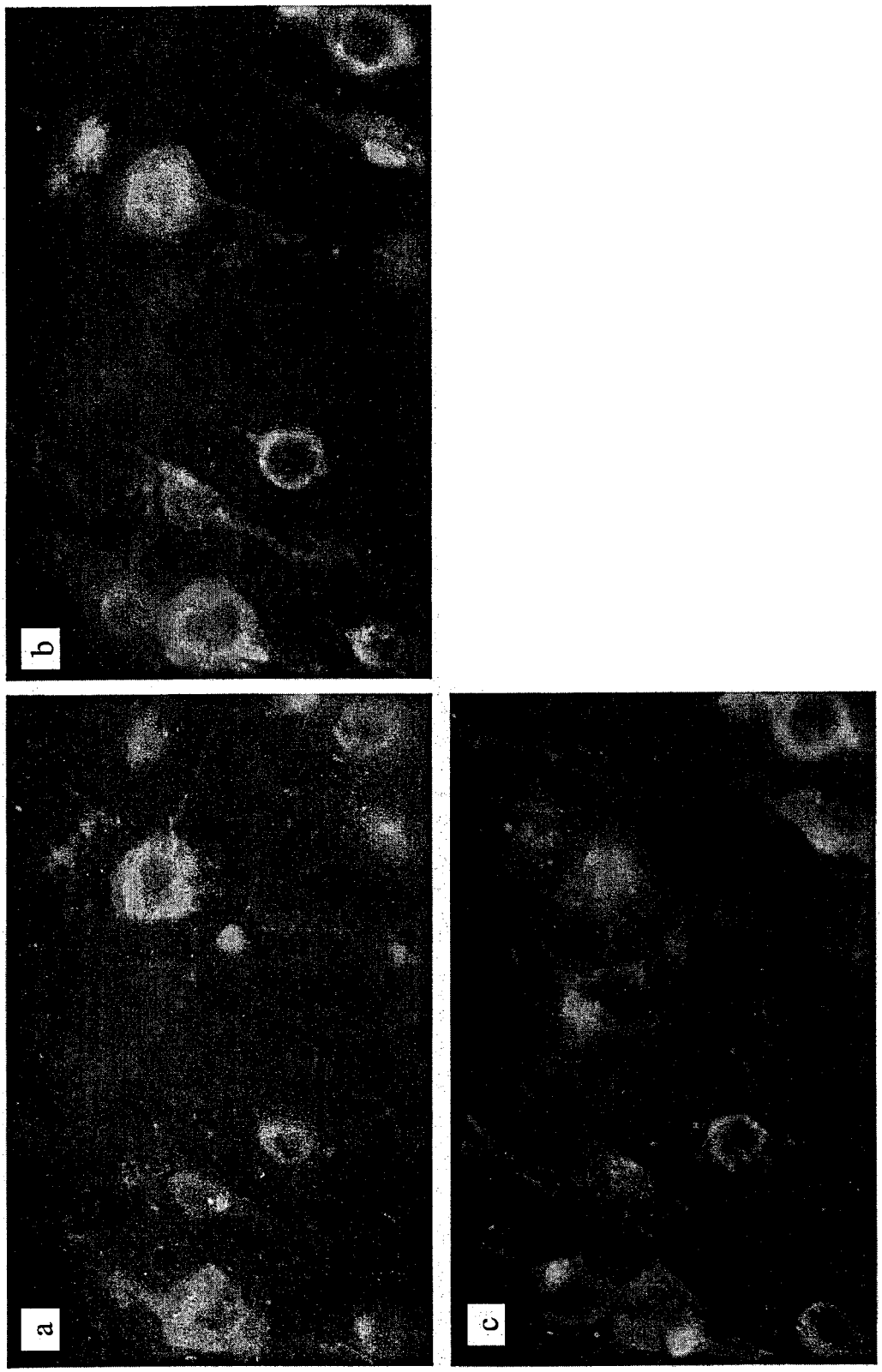
FIG. 5 shows co-localization of bIII-tubulin (a neuronal marker) and BrdU immunoreactivity in the same cells. (a-c) Three different planes of the same microscopic view. The bIII-tubulin positive cells (green) show BrdU positive nuclei (red) indicating that these cells are derived from transplanted NSCs.

The transplanted MNSCs, with BrdU immunopositive nuclei, were stained for human bIII-tubulin and human GFAP. Double immunolabeling with bIII-tubulin and BrdU in three different planes from the same microscopic view clearly showed the co-localization of these two signals in the same cells (FIG. 5). According to the manufacturer's description, the anti-bIII-tubulin antibody may also recognize the host (rat) bIII-tubulin. Despite this, the specific co-localization of the bIII-tubulin and BrdU at different planes indicate that the majority of bIII-tubulin immunopositive cells were indeed transplanted cells of the invention. This may be because bIII-tubulin is mainly expressed in immature neurons, the majority of which are transplanted cells as disclosed herein. The presence of these cell specific antigens indicates that the transplanted cells of the invention successfully differentiated into neurons and astrocytes, respectively.

NSC Culture:

NSCs were purchased (BioWhittaker, Walkersville, Md.), and alternatively isolated from human tissue, and cultured in a nonsupplemented, serum-free basal medium comprising HAMS-F12 (Gibco, BRL, Burlington, ON); antibiotic-antimycotic mixture (1:100, Gibco); B27 (1:50, Gibco); human recombinant FGF-2 and EGF (20 ng/ml each, R and D Systems, Minneapolis, Minn.) and heparin (5 ug/ml, Sigma, St. Louis, Mo.). The cells were incubated at about 37° C. in a 5% $CO_2$ humidified incubation chamber (Fisher, Pittsburgh, Pa.). To facilitate optimal growth conditions, clusters of one or more NSCs were sectioned into quarters every 2 weeks and fed by replacing 50% of the medium every 4-5 days. To inhibit differentiation, the cells can be propagated on uncoated flask or a flask that has been treated to repel the cells. To induce differentiation, these cells can be replated in the culture dishes (about $1 \times 10^5$ per dish) in the serum-free basal medium Eagle (BME), which comprises Earle's salt and L-glutamine, and cultured for about 5 days in the absence of FGF-2 and EGF and without the addition of other extrinsic differentiation factors. NSCs cultured in this serum-free medium can spontaneously undergo differentiation into neuronal cell types.

Example 2

Neural Differentiation of MeSCs In Vitro

Figure 6:
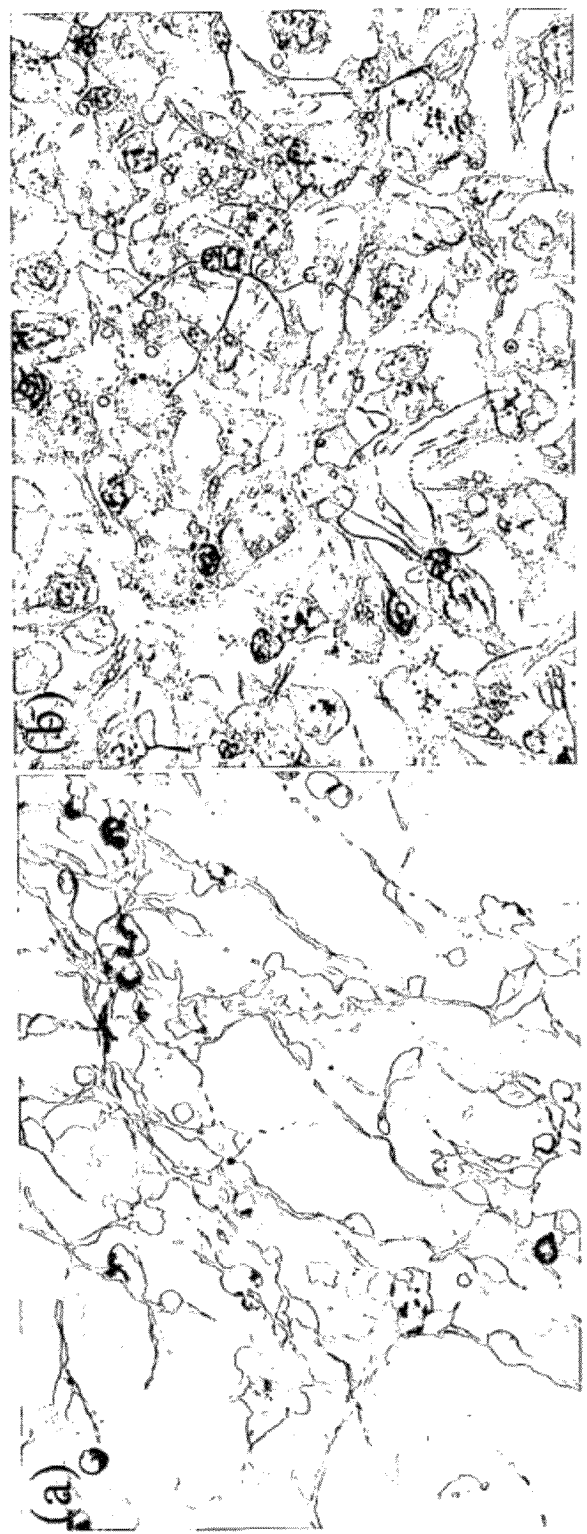
FIG. 6 (I) shows the immunohistochemistry of differentiated human MNSCs using antibodies against bIII-tubulin (a) and glial fibrillary acidic protein (GFAP) (b).

Neural stem cells have been isolated from embryonic and adult mammalian and human (Doetsch et al., 1999, Cell 97: 703-16; Johansson et al., 1999, Cell 96: 25-34) central nervous system (CNS) and propagated in vitro in a variety of culture systems (Svendsen et al., 1999, Brain Pathol. 9: 499-513). The inability to grow neural progenitors in culture in the absence of complex and undefined biological fluids (for example, serum) has long been a major obstacle in understanding the physiology of these cells. Long-term culture systems to proliferate MeSCs and NSCs were established (Brannon et al., 2000, Neuroreport 11: 1123-8). The ability of multipotent human NSCs to expand in vitro produces well-characterized material for biological research. As grown in ling term culture, NSCs are differentiated into bIII-tubulin- and glial fibrillary acidic protein (GAFP)-immunopositive cells (Brannon et al., 2000, Neuroreport 11: 1123-8). After three years of in vitro expansion, such human NSCs remain capable of producing neurons and glia on differentiation (FIG. 6(I)) under non-serum basal media conditions, indicating the multipotency of these cells, thus demonstrating that this culture system is optimal to maintain NSCs and to investigate their biology. NSCs were also differentiated in co-culture with an oxidatively damaged human neuronal cell line (Sy5). The overnight culture of Sy5 cells were grown in the media described elsewhere herein, treated with 0.0, 0.01, 0.03 or 0.1 μM $H_2O_2$ in NSC media for 15 minutes, thoroughly washed with DMEM-F12 media, then co-cultured with NSCs. The results (FIG. 6(II)) indicate that the can be differentiated into neurons and astrocytes by responding to damaged neuronal cells even after lengthy in vitro expansion.

Figure 7:
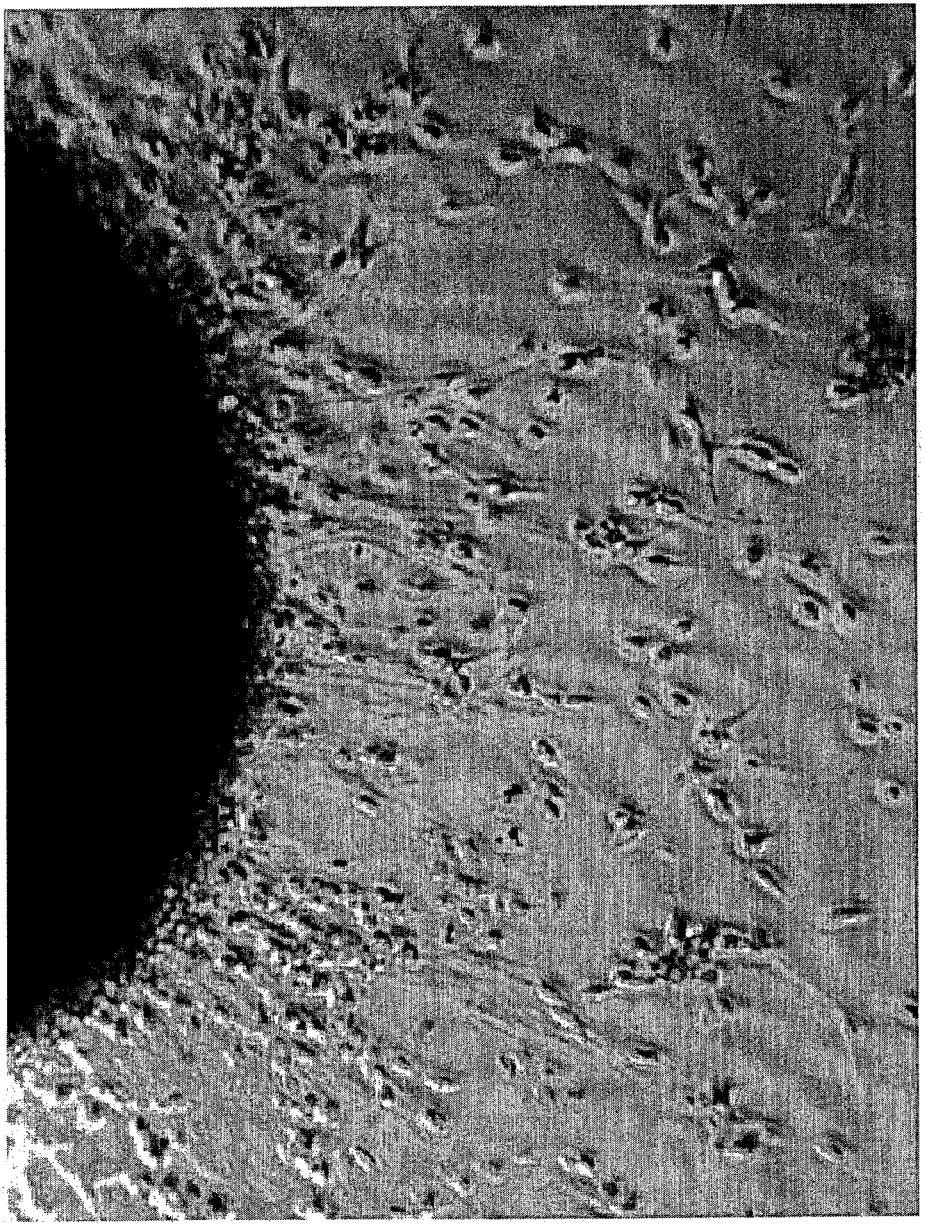
FIG. 7 shows spontaneous differentiation of MNSCs in serum-free basal media. Mixed populations of differentiating cells are coronally migrating outward from a cluster of cells located on the top of the picture.

The fate of stem cells is greatly influenced by contextual cues. Stem cells can respond and differentiate into specific cell types according to the environmental cues to which they are exposed. Further, when cells that are incapable of differentiating in response to environmental cues (such as MeSCs which do not respond to neural environmental cues) are treated with substituted deoxynucleotide or deoxynucleosides according to the methods of the invention, they are rendered capable of so differentiating. They become more developmentally potent in character. Herein is demonstrated that neural tissue produces environmental factor(s) that can initiate neural lineage in MeSCs pretreated with BrdU. MeSCs were co-cultured with differentiated NSCs after BrdU treatment (10 μM BrdU for 5 days before co-culture) of the MeSCs. MeSCs did not differentiate into neurons or glia (bIII-tubulin and GFAP negative) after use of serum or basal differentiation conditions (data not shown). NSCs were differentiated in 12-wells tissue culture plates under the basal media condition; i.e., serum-free basal medium containing Earle's salt and L-glutamine (Invitrogen) for five days prior to co-culture. NSCs spontaneously differentiated into mixed cell populations, including neural precursors that formed a cluster of two or more cells in the middle, and coronary migrating immature and/or mature neurons and astrocytes (FIG. 7). MeSCs treated with BrdU were then transferred onto a tissue culture 0.4 μm membrane insert (Falcon) and placed on top of the differentiated NSCs in basal media conditions.

Figure 8:
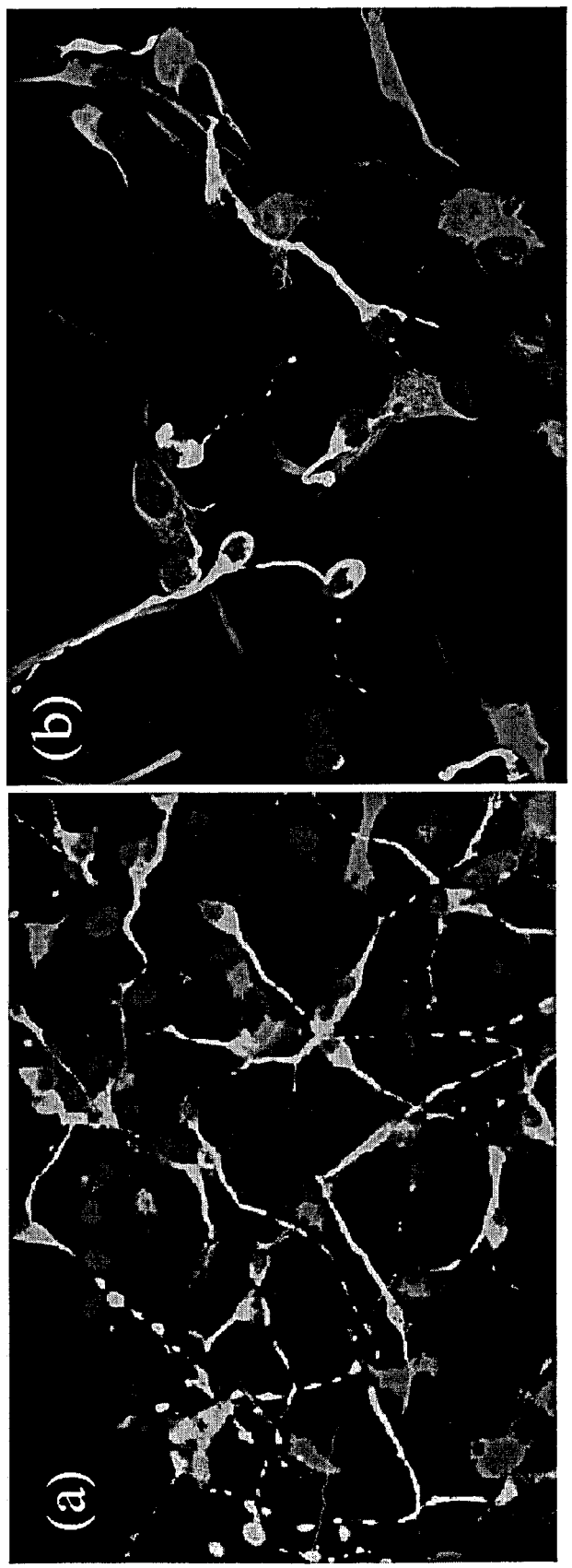
FIG. 8 shows fluorescent immunocytochemistry of differentiated human MNSCs (a) and MeSCs (b) of the invention. bIII-tubulin (green) and GFAP (red) immunoreactivity indicate neuronal and glial differentiation, respectively. Nuclei counter-staining with DAPI is shown in blue.

Immunocytochemical examination seven days post-coculture revealed that BrdU-treated MeSCs differentiated into bIII-tubulin immunopositive small bipolar and unipolar cells (approximately 40% of total cells), and GFAP-immunopositive large flattened multipolar cells (approximately 60% of total cells) (FIG. 8). Although the process of bIII-tubulin immunopositive cells derived from MeSCs was shorter than those found in differentiated NSCs, the general morphology of the cells in both NSCs and MeSCs-differentiated cultures were similar (FIG. 8). This result indicated that BrdU pretreated MeSCs are capable of becoming neurons and astrocytes when co-cultured with differentiated NSCs. On the other hand, MeSCs without BrdU treatment did not express either bIII-tubulin or GFAP immunoreactivity and remained in a fibroblast-like morphological state even after co-culture, demonstrating clear evidence that substituted deoxynucleotide or deoxynucleoside treatment is necessary to initiate neural lineage change in MeSCs.

Since no exogenous differentiation factors such as, for example, retinoic acid and BDNF (brain derived neurotrophic factor) were added to cultures, and no cell-to-cell contact existed in this co-culture system, it appears that membrane permeable endogenous factor(s) were released from differentiating NSCs and altered the cell fate decisions of BrdU-treated MeSCs in a manner not possible with non-treated MeSCs. That is, BrdU-treated MeSCs acted as more developmentally potent cells, in this case like NSCs, which are capable of responding to neural environmental cues.

MeSCs Culture:

Though they can be isolated utilizing numerous methods well known in the are, for the present examples, human MeSCs were purchased (BioWhittaker, Walkersville, Md.) and selected by negative selection for CD11b, CD33, CD34, and CD133 antigens. The MeSCs were cultured in, for example, 20 ml of serum-supplemented growth medium consisting of Dulbecco's Modified Eagle Medium (Gibco, BRL, Burlington, ON); antibiotic-antimycotic mixture (Gibco); and FBS MesenCult Medium (Stem Cell Technologies, Vancouver, BC). The cells were incubated at 37° C. in a 5% $CO_2$ humidified incubation chamber (Fisher, Pittsburgh, Pa.). The cells were fed by replacing half the culture media twice per week. After 60 passages, the cells were still negative for the above-listed antigens. Before in vitro and in vivo differentiation, human MeSCs were treated with different doses (10 nM-100 μM) of 5-bromo-2-deoxyuridine (BrdU, Sigma) for various durations (24-240 hr). To investigate whether DNA methylation is involved in the BrdU effect, cells were treated with BrdU in the presence of 5-azacytidine (0.3-1 mM). The preceding growth conditions are applicable to cell types other than MeSCs, such as, for example, NSCs and other stem cells.

Co-Cultures of Human MeSCs and NSCs:

Human NSCs (about $1 \times 10^4$ to $1 \times 10^5$) were differentiated in serum-free basal medium Eagle (BME, Gibco), which contains Earle's salt and L-glutamine for five days in a 12-well culture plate before co-culture in the absence of FGF-2 and EGF and without the addition of other extrinsic differentiation factors. Under these condition, NSCs spontaneously differentiated into neurons and glia. For the co-culture experiments, BrdU-treated human MeSCs (about $1 \times 10^4$ to $1 \times 10^5$) were transferred into cell culture inserts with a pore size of 0.4 μm (Falcon, Franklin Lakes, N.J.) and suspended in the basal medium over these differentiating NSCs. The ratio of MeSCs to NSCs was approximately 1:1. For immunocytochemical analysis of MeSCs, the culture insert was removed from the well after seven days of co-culture and the MeSCs were fixed with methanol for 30 min at −20° C.

Immunocytochemistry:

After fixation, MeSCs were briefly washed three times in PBS, then blocked with 3% donkey normal serum in PBS containing 0.05% Triton X-100 (PBST) for 1 hour and incubated with mouse IgG2b monoclonal anti-human bIII-tubulin, clone SDL3D10 (1:500, Sigma) and goat anti-human-glial filament protein (GFAP) N-terminal human affinity purified (1:200, Research Diagnostics Inc., Flander, N.J.) overnight at 4° C. The corresponding secondary antibodies were donkey anti-mouse conjugated to rhodamine and anti-goat IgG (H+ L) conjugated to FITC (Jackson IR Laboratories, Inc.), respectively. Following a brief PBS washing, secondary antibodies were added at a 1:200 dilution in PBST for a 2 hr incubation at room temperature (RT) in the dark. The cells were then washed with PBS and covered with Vectashield with DAPI (Vector Laboratories, Inc., Burlingame, Calif.) for fluorescent microscopic observation.

Image and Data Analysis:

Digitally-captured images from fluorescent microscopy of cultured cells can be analyzed by NIH Image software (NIH) with Cell Scoring, Particle Analysis, and Cell Analysis macros. The number of cells showing particular antibody markers in the areas of interest can be counted. In addition, total cell number can be counted by DAPI nuclei counterstaining and each cell population will be expressed as a percentage of the total cell number. The results from each treatment condition can be analyzed by ANOVA and followed by post-hoc (Fisher's Protected LCD) analysis.

Example 3

Neural Differentiation of MeSCs of the Invention in Mouse Brain

To test migration and differentiation patterns of BrdU-treated, more developmentally potent MeSCs in vivo, such MeSCs expanded without differentiation as described above and labeled by the incorporation of bromodeoxyuridine (BrdU) into nuclear DNA were injected into the lateral ventricle of mature mice (C57/black).

Figure 9:
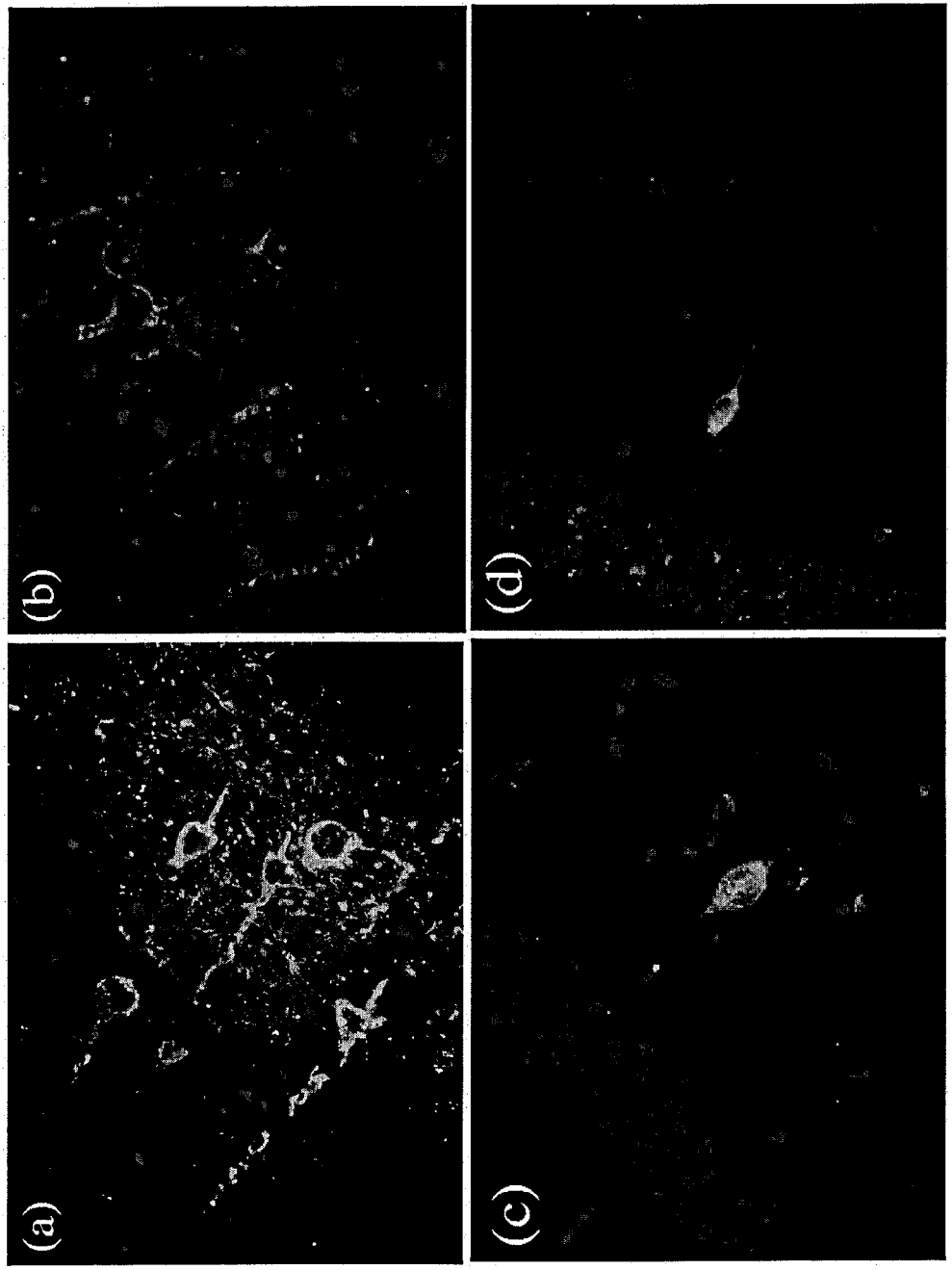
FIG. 9 shows typical fluorescent immunohistochemical photomicrographs in rat brain 4-6 weeks after transplantation of more developmentally potent MeSCs of the invention. bIII-tubulin immunoreactivity was used as a neuronal marker. Since MeSCs were treated with BrdU before transplantation, transplanted cells have BrdU positive nuclei (red). MeSCs migrated into the cortex and differentiated into neurons as indicated by the bIII-tubulin positive cells (green), which have morphologies typical of pyramidal cells (a, b). All the human specific bIII-tubulin (green) positive cells show BrdU (red) positive nuclei while many other host cell nuclei are stained with only DAPI (blue). Apical dendrites were wavy compared with the neurons differentiated from MNSCs but pointed towards to the edge of the cortex. MeSCs tend to have larger nuclei than host cells. MeSCs migrated into the hippocampus and differentiated into bIII-tubulin positive cells (green), in CA1 pyramidal cell layer (c-h). These bIII-tubulin positive cells have BrdU positive nuclei (red), indicating that these cells originated from transplanted cells. In contrast, host cell nuclei counter stained with DAPI (blue) are not bIII-tubulin positive. At four weeks post transplantation (c,d), the bIII-tubulin positive cells show bipolar neuronal morphology and may still be migrating to the pyramidal cell line. At 5 weeks post transplantation, some of the cells have already reached the pyramidal cell line and have started to change morphologies. At six weeks post transplantation (g,h), the cells start to show pyramidal cell like morphologies

Four to six weeks after transplantation, mouse brains were analyzed by immunohistochemistry for human specific bIII-tubulin and GFAP, markers for neurons and astrocytes respectively. Migration and differentiation patterns of the transplanted MeSCs were quite similar to our previous results with NSCs transplanted into the rats. The transplanted MeSCs with BrdU-immunopositive nuclei differentiated into neurons and astrocytes in the host brain as evidenced by fluorescence microscopy after double staining for bIII-tubulin and GFAP. MeSC-derived cells are found bilaterally in regions of cerebral cortex and hippocampus. The transplanted MeSCs migrated over a long distance from the injection site to their positional termination. Further analysis with double immunostaining for bIII-tubulin and GFAP revealed that MeSC-derived neurons and astrocytes were localized in layer V and III, respectively, in the cortex (FIG. 9a,b). These neurons were characterized by dendrites pointing to the edge of the cortex, and these neuronal dendrites appeared to be associated with the astrocytes in the layer III of the cortex. Around the pyramidal cell layer of the hippocampus (FIG. 9c-h), neurons were immunopositive for bIII-tubulin and exhibited morphologies with multiple processes and branches. Strong astrocyte staining for GFAP was observed in the CA2 subfield of hippocampus. MeSCs-derived cells, with BrdU-labeled nuclei, also were localized to areas undergoing active postnatal neurogenesis, including the Islands of Calleja in the ventral forebrain and the subependyma of the olfactory bulb.

Without the BrdU-treatment, MeSCs transplanted in an animal's brain do not exhibit immunoreactivity for the human bIII-tubulin and human neurofilament, indicating that BrdU-treatment is necessary for differentiation of MeSCs even though environmental cues also contribute to the induction of neuronal differentiation of the MeSCs.

These results from in vitro and in vivo tests indicate that MeSCs overcome their mesenchymal commitment by substituted deoxynucleotide or deoxynucleoside treatment and differentiate into neural lineage cells that are phenotypically unrelated to their embryonic origin.

Example 4

Migration and Differentiation of MeSC of the Invention after Transplant into Rat Vitreous Cavity For transplanting the MeSCs into the vitreous cavity of rats, cells were cultured with the long-term maintenance media as described above, containing TGF-b3 (1 ng/ml to 10 micrograms/ml; here 100 ng/ml) and about 2 µM 5-bromo-2'-deoxyuridine (BrdU) for 3 days in a 6-well tissue culture without differentiation before injection.

An injury was intentionally made by a needle while these cells were injected to facilitate the migration of MeSCs. After an injury, 200 of cell suspension, containing about $1.5 \times 10^5$ to $2 \times 10^5$ cells, was slowly injected into the intravitreous space of the right eye. The left eye was left intact as a control without injection. At 30 days post-transplantation, the rats were sacrificed and their eyeballs were removed whole. Then these eyeballs were paraffin embedded and sliced into 5 µm sections. The sections were stained with double-immunofluorescent-cytochemistry using rat anti BrdU (1:600, Accurate Chemical & Scientific Corp.) and mouse anti-rhodopsin (1:200, Chemicon), and mounted on slides, then coverslipped using VECTASIELD mounting medium (Vector) with DAPI.

Figure 10:
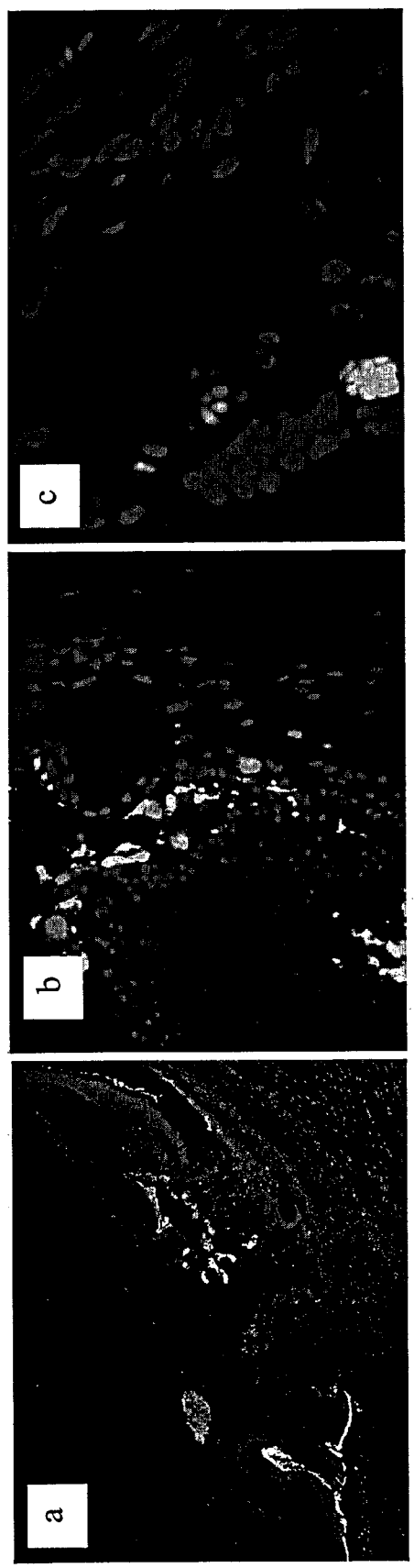
FIG. 10 shows differentiation of MeSCs into retinal cells in vivo. All nuclei were counterstained by DAPI (blue). (a) Typical immunocytochemistry of retinal sections 4 weeks after a lesion and transplantation of MeSC of the invention (×100). The section was double-immunofluorescence stained with BrdU (red) and opsin (green) markers for donor cells and photoreceptor cells, respectively. MeSCs of the invention migrated into damaged area of the retinal tissue. A higher magnification (b, ×400) shows that these migrating MeSCs also show cytosolic expression of opsin. (c) Typical in situ hybridization histochemistry (×100) for human opsin gene expression using human-specific opsin sequence riboprobes (green). Incorporation of human opsin positive cells to the rat retinal tissue is observed

FIG. 10 show the immunocytochemistry and in situ hybridization histochemistry (ISHH) of the retinal sections 4 weeks after transplantation of MeSCs pretreated with BrdU and TGF-b3. Extensive migration of these cells into the lesioned area of the retina was found (FIG. 10a), similar to other researchers, who found migration and incorporation of neural stem cells into the retina after intraocular injections (Nishida et al., 2000, *Invest Ophthalmol Vis Sci* 41: 4268-74; Kurimoto et al., 2001, *Neurosci Lett*. 306: 57-60; Warfvinge et al., 2001, *Exp. Neurol*. 169: 1-12). However, for the first time is demonstrated herein that MeSCs incorporated into the photoreceptor layer are in fact able to express opsin immunoreactivity (FIG. 10b), in contrast to previous studies that did not report such findings (Ibid). Since anti-opsin antibody that recognized both human and rat opsin protein was used, it was not determined whether opsin is expressed by the donor (human stem cells) or by the host (rat cells). To overcome this technical problem, ISHH was conducted as described below against the human rhodopsin gene-encoding region. The cloned human rhodopsin gene sequence does not recognize any other species of opsin genes listed by Genbank: in particular, this sequence does not show a significant similarity to any DNA sequence found in rat genes (data not shown). Using the human opsin gene sequence as a DIG-labeled RNA probe, human opsin expression was detected in the retina following human stem cells transplantation (FIG. 10c). These results indicated that MeSCs pretreated with BrdU and TGF-b3 not only were incorporated into the rat retina, but they also differentiated into photoreceptor cells. MeSCs that were not pre-treated with BrdU according to the methods of the invention were not able to migrate and differentiate in a tissue-appropriate manner.

Construction of Exemplary Human-Specific Opsin Riboprobe Vectors:

A 360 bp fragment of a human-specific rhodopsin gene sequence (from 6241 bp to 6601 bp of U49742) was selected. The selected human rhodopsin gene sequence does not have a significant level of homology with other rhodopsin genes from other species. In particular, this sequence does not show a significant similarity to any DNA sequence found in the rat genome (data not shown). The selected human-specific rhodopsin gene sequence was amplified from human genome DNA by PCR using a forward primer (5'-TTCCCAAT-GAGGGTGAGATT-3'; SEQ ID NO: 1) and a reverse primer (5'-GGAATTTCCCACTCTTTGTT-3'; SEQ ID NO: 2). PCR amplification was conducted in 50 µl volumes containing control human genomic DNA (100 ng, Invitrogen), 1× amplification buffer (Invitrogen), 40 nM of each primer, dNTP Mix (250 µM, Invitrogen) and Taq DNA Polymerase (2.5 U, Invitrogen), under conditions of: 95° C. (30 seconds), 52° C. (30 seconds), and 72° C. (60 seconds) for 30 cycles. The PCR-amplified fragment was ligated into a TOPO TA cloning in vitro transcription vector (Invitrogen) after gel purification on 2% agar gel. The plasmid was transformed into *E. coli*-competent cells (Strategene) and the clone was confirmed by sequencing the insert.

In Situ Hybridization Histochemistry for Human Opsin mRNA in Paraffin Embedded Sections:

Digoxigenin-labeled human opsin-specific riboprobes are made by in vitro transcription. Reactions (20 µl) were performed in a reaction mixture containing 4 µl of 5× transcription buffer (USB Corporation), 2 µl of 10× digoxigenin RNA-labeling mix (0.2 µg/ml, Roche), 1 µl of template DNA (PCR reaction described above, 100 ng/µl), 2 µl of T7 RNA polymerase (5 U/µl, USB), and 11 µl of molecular biology grade water. After mixing with a pipette, the reaction mixture was incubated at room temperature for 2 hours. The probe was purified by ethanol precipitation and dissolved in 1000 molecular biology-grade water. 10 µl of this probe solution was used to make the hybridization mixture. Rat eye sections were deparaffinized with xylene (Fisher) for 5 minutes at room temperature, and rehydrated using a serial concentration of ethanol (Fisher) and distilled water at room temperature. The sections were then washed with 0.1 M phosphate-buffered saline (PBS), pH 7.4, for 15 min at room temperature followed by incubation with 10 ng/ml of proteinase K (Sigma) for 30 minutes at 37° C. The sections were washed twice in glycine solution (0.75 g glycine/100 ml of 0.1 M PB, pH 7.4) for 5 minutes at room temperature and treated with 13% triethanolamine solution (pH 8.0) containing 2.5% acetic anhydride for 10 minutes at room temperature. The sections were then prehybridized with hybridization buffer after 2 washes with 2xSSC (saline-sodium citrate buffer, Sigma, pH 7.0) for 15 minutes each at room temperature (RT). Hybridization buffer consists of 50% formamide, 1xDenhardt's solution, 10% dextran sulfate (Invitrogen), 4xSSC, 0.25 mg/ml yeast tRNA, and 0.3 mg/ml herring sperm DNA. Hybridization was done in the hybridization buffer containing 10 µl of digoxygenin riboprobe as described above for 18 hours at 60° C. After hybridization, the sections were washed twice with 4xSSC buffer, followed by a stringency wash with 50% formamide and 2xSSC for 30 minutes at 60° C. The sections were washed twice with RNase buffer (10 mM Tris, pH 8.0, 0.5 M NaCl, 1 mM EDTA) for 10 minutes at room temperature and then incubated with RNase solution (50 ug/ml of RNase (Promega) in RNase buffer) for 30 minutes at 37° C. The sections were washed with serial concentration of SSC buffer (2x, 0.5x, 0.1x) twice for 20 minutes at 60° C., except that the last wash was done at RT. After rinsing with PBS, the probe was visualized by immunodetection of digoxygenin with a primary antibody, sheep anti-digoxigenin (1:500, Roche), and secondary antibody with fluorescein (FITC)-conjugated AffiniPure donkey anti-sheep IgG (1:200, Jackson Laboratories).

Image and Data Analysis:

Digitally-captured images from the fluorescent microscopy of cultured cells can be analyzed utilizing NIH Image software (NIH) with Cell Scoring, Particle Analysis, and Cell Analysis macros as described above.

Example 5

DNA Methylation and BrdU

Figure 11:
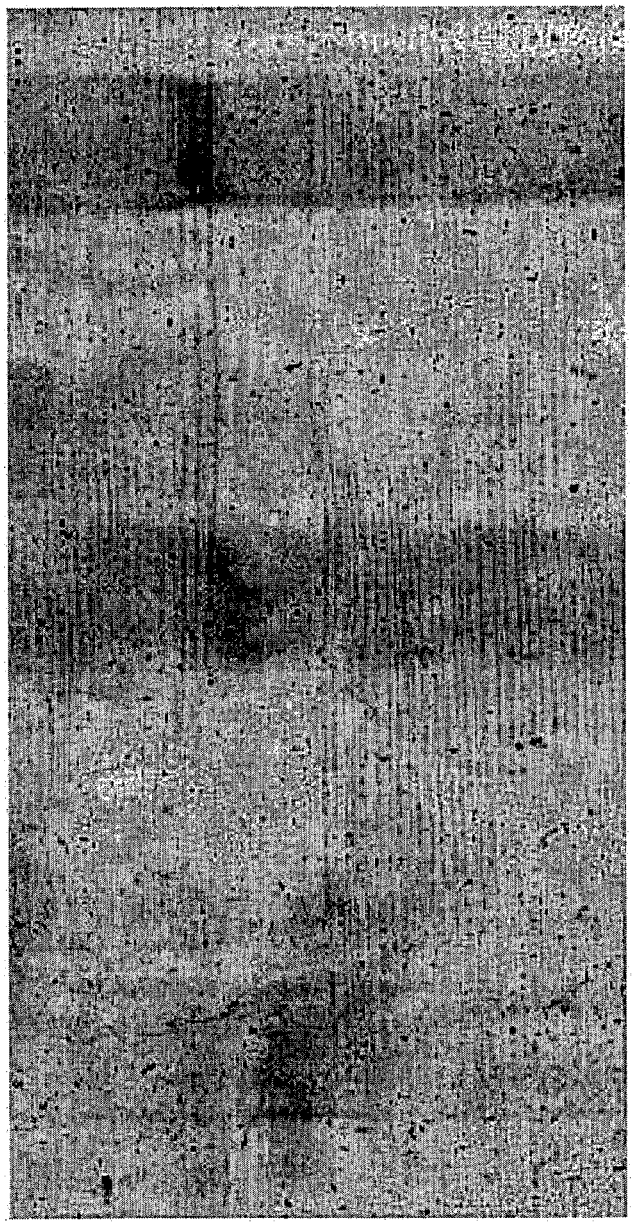
FIG. 11 shows effect of BrdU on restriction enzyme digestion of genomic DNA extracted from human MeSCs. BrdU prevents methylation-sensitive restriction enzyme digestion of DNA in a dose-dependent manner, indicating that BrdU treatment of MeSCs increased DNA methylation sites in the genomic DNA.

Some DNA restriction digestion enzymes are sensitive to cytosine methylation, and they are unable to cut DNA when the cutting site includes methylated cytosine. One such enzyme (HpaII) was used to investigate whether BrdU treatment altered the enzyme-cutting pattern by modification of DNA methylation. Genomic DNA from human MeSCs treated with 0 µM, 1 µM and 10 µM BrdU for 72 hr was digested and analyzed by polyacrylamide gel electrophoresis on 0.6% polyacrylamide gel. In a dose-dependent fashion the size of the DNA fragments produced by digestion increased, indicating that BrdU prevented enzyme digestion (FIG. 11). This result may be explained by the alteration of DNA methylation status in MeSC by the BrdU treatment. Other substituted deoxynucleotide or deoxynucleoside compounds are suitable replacements for BrdU.

Example 6

Transplantation of More Developmentally Potent Cells of the Invention to Nucleus Basalis Magnocellularis (NBM) Lesion Rat Model Stem cell transplantation strategies are advocated in Alzheimer's disease (AD) neuroregeneration therapy. Basal cholinergic neurons, which are selectively degenerated in AD, extend long projections into the cortex and hippocampus. An open question for neuroreplacement treatment for AD is whether these degenerating cholinergic cells can be replaced by the transplantation of stem cells. To answer this question, more developmentally potent cells of the invention were transplanted into nucleus basalis magnocellularis (NBM) lesion model rats. The lesions were induced either by an injection of ibotenic acid or by anti-NGF receptor antibody conjugated with saporin (Advanced Targeting System, San Diego, Calif.). Cells prepared according to the invention were simultaneously injected into the contralateral side of the lateral ventricle (Qu, 2001) of the NBM-lesioned animal. Four weeks after the surgery, the brain was examined by immunohistochemistry. Many GFAP-positive cells were detected in the lesioned area, but they were not BrdU-positive, indicating astrocytes activation in this area. BrdU-positive cells with ChAT or bIII-tubulin immunoreactivity were found in the lesion site, indicating that more developmentally potent cells of the invention migrated from the contralateral ventricle to the lesion site and had differentiated into cholinergic and other neuronal cells. These neuronally differentiating cells were neurons that appeared rather morphologically premature. Our results indicate a positive study of neuroreplacement treatment for cholinergic neurons in AD.

Transplantation of Cells of the Invention:

Male SD rats were deeply anesthetized with sodium pentobarbital (50 mg/kg, i.p.). Using bregma as a reference point, about $1 \times 10^5$ cells of the invention were collected and slowly injected into the right lateral ventricle (AP 1.4; ML 3.3; and DV 4.5 mm) of the rat brain using a stereotaxic apparatus (Devid Kopff).

Cholinergic Lesions Induced by 192-IgG-Saporin Conjugate:

Male Sprague-Dawley rats, 4-months-old, were anesthetized with 50 mg/kg pentobarbital and mounted in a stereotaxic apparatus (David Kopf). Unilateral NBM injections of the 1 µg/2 µl 192-IgG-saporin conjugate toxin (in a vehicle of sterile filtered 200 mM phosphate buffer (pH 7.4)) were performed using a microsyringe. The NBM was stereotaxically localized using the following coordinates: AP=−2.3 mm from bregma, ML=±3.7 mm, 7.5 mm below dura. The toxin was delivered over 5 minutes and the needle was left in place for another 5 minutes following injection.

Immunohistochemistry:

Rats were sacrificed by an overdose of anesthesia (sodium pentobarbital, 70 mg/kg, i.p.) and perfused with phosphate buffered saline (PBS) followed by 4% paraformaldehyde. Brains were removed and placed into the 4% paraformaldehyde fixative containing 20% sucrose for overnight. The brains were sliced into 20 µm, coronal sections using cryomicrotome. The sections were washed briefly in PBS and pretreated with 1M HCL for 30 minutes at room temperature (RT) and neutralized with sodium borate (0.1M, pH 8.0) for 30 minutes, in order to increase the accessibility of the anti-BrdU antibody to the BrdU incorporated in the cell nuclei. After rinsing with PBS, sections were transferred to a solution containing 0.25% Triton X-100 in PBS (PBST) for 30 minutes. Then the sections are blocked in PBST containing 3% donkey normal serum for 1 hr and incubated in mouse anti-BrdU (1:200; DSHB, Iowa City, Iowa) or sheep anti-BrdU (1:1000; Jackson IR Laboratories, Inc. West Grove, Pa.) diluted in PBST overnight at 4° C. Sections were then washed with PBS and incubated with mouse IgG2b monoclonal anti-human bIII-tubulin, clone SDL3D10 (1:500, Sigma), rat IgG monoclonal anti-ChAT (1:500, Boehringer-Mannheim) and goat anti-human-glial filament protein, N-terminal human affinity purified (1:200, Research Diagnostics Inc., Flander, N.J.), respectively, for overnight at 4° C. in the dark. After rinsing in PBS, donkey anti-mouse, donkey anti-rat, donkey anti-goat or donkey anti-sheep IgG conjugated with rhodamine or FITC (Jackson IR Laboratories, Inc.) were added at 1:200 dilution in PBST for 2 hours at RT in the dark. Sections were then washed with PBS thoroughly before mounting on glass glides. The sections were coverslipped with mounting media containing DAPI for nucleus counter staining.

Figure 12:
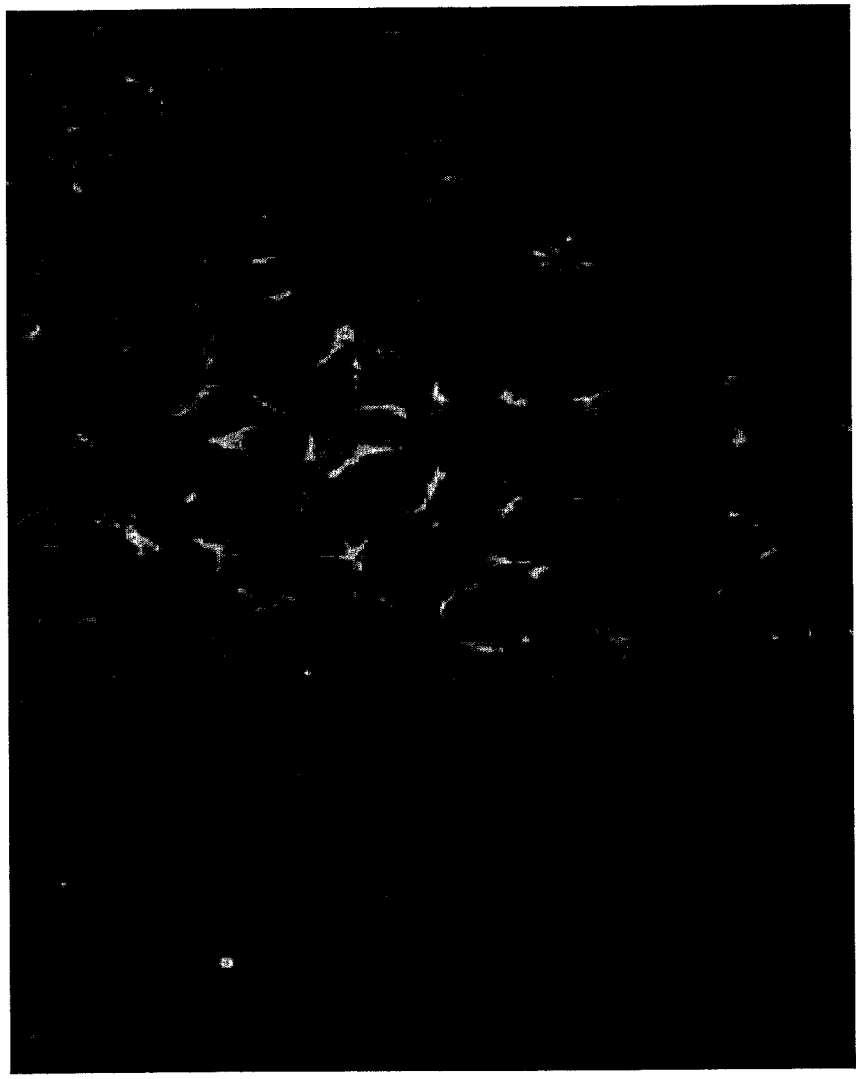
FIG. 12 shows increased GFAP immunoreactivity in the nucleus basalis magnocellularis (NBM) 4 weeks after saporin lesion. Green: GFAP; Blue: DAPI.
Figure 13:
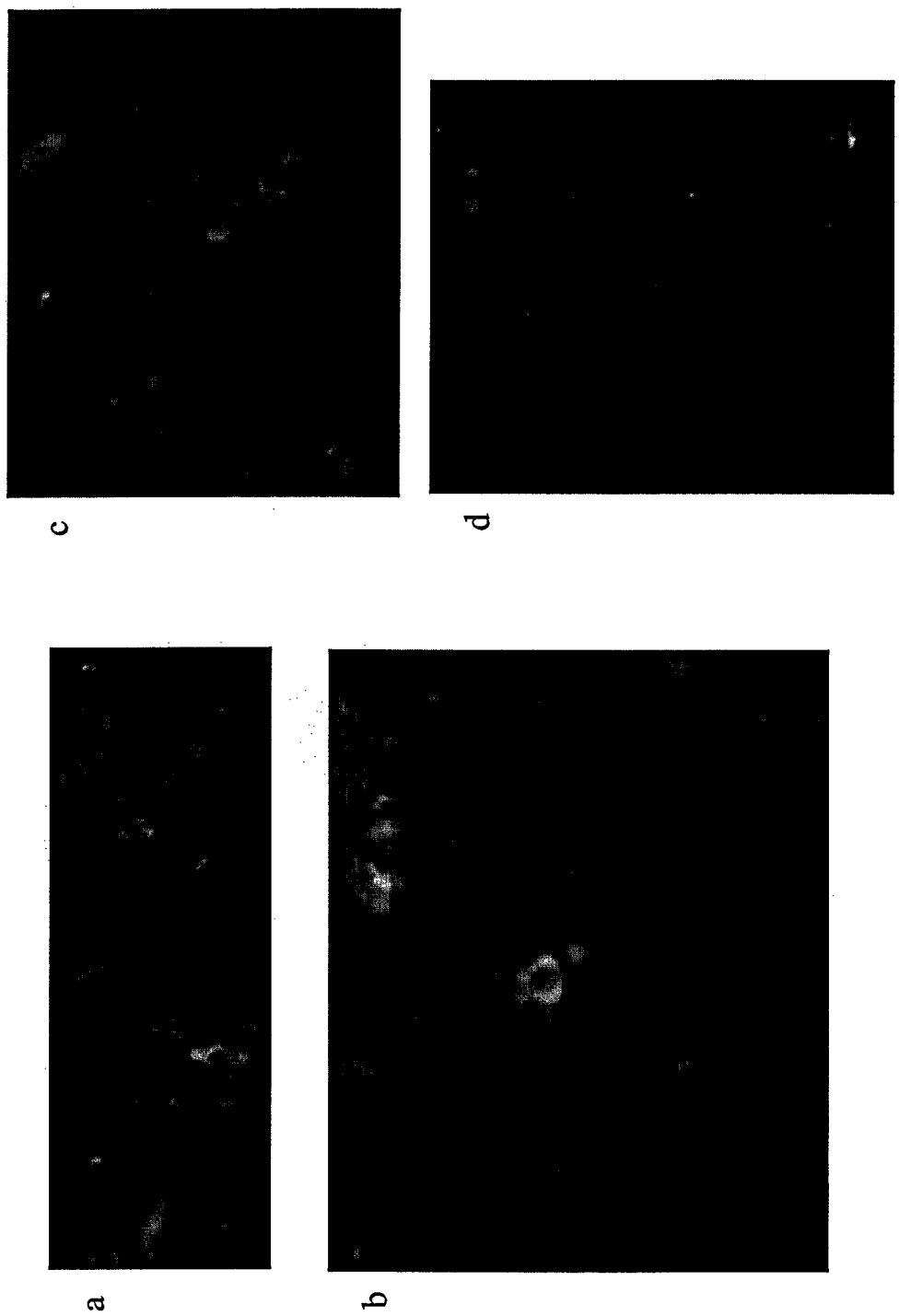
FIG. 13 shows choline acetyltransferase (ChAT) immunoreactivity in BrdU positive cells in the lesion site indicating replacement of lesioned cells by the transplanted cells of the invention (a-c; Green: ChAT; Red: BrdU; Blue: DAPI) and ChAT immunoreactivity in human nuclei positive cells in the lesion site (d; Green: ChAT; Red: human nuclei; Blue: DAPI).
Figure 14:
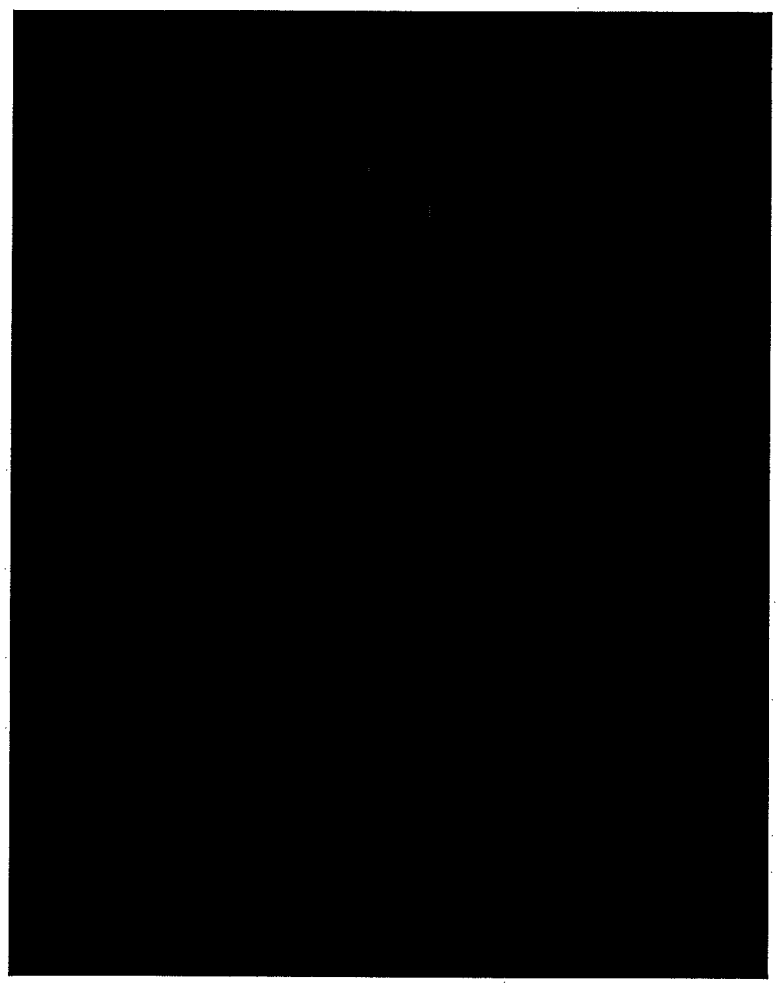
FIG. 14 shows human nuclei immunoreactivity-positive cells that were observed in the lesion area. Red: human nuclei; Blue: DAPI.
Figure 15:
FIG. 15 shows GFAP and human nuclei immunoreactivity in the lesion site. Green: GFAP; Red: human nuclei; Blue: DAPI.

Increased GFAP immunoreactivity in the NBM was observed 4 weeks after saporin lesion. (FIG. 12. Green: GFAP; Blue: DAPI). Choline acetyltransferase (ChAT) immunoreactivity was also observed in BrdU positive cells in the lesion site (FIG. 13a-c. Green: ChAT; Red: BrdU; Blue: DAPI), indicating replacement of lesioned cells by the transplanted cells of the invention. Further, ChAT immunoreactivity was observed n human nuclei positive cells in the lesion site. (FIG. 13d. Green: ChAT; Red: human nuclei; Blue: DAPI). Human nuclei immunoreactivity-positive cells were observed in the lesion area (FIG. 14. Red: human nuclei; Blue: DAPI) and GFAP and human nuclei immunoreactivity were observed in the lesion site. (FIG. 15. Green: GFAP; Red: human nuclei; Blue: DAPI). A large number of transplanted cells migrated to the lesion site and differentiated into rather mature neurons and glia 4 weeks after transplantation. The lesion appears to attract the cells of the invention, indicating a possible release of the migration factor(s) from the lesion site.

Example 7

Expression of Reelin, Alpha 3-Integrin, and DAB-1 in Stem Cells

To investigate the function of reelin in cell culture, human MNSCs were differentiated under serum-free conditions. Previously, human MNSCs were observed not only survive at least three weeks in serum-free conditions, but to fully differentiate into b3-tubulin, GFAP, and O4 immunopositive cells.

Reelin may serve to regulate migration based on the finding that exposure to recombinant reelin causes the differentiating human MNSCs cultures to immediately retract their processes back to the cell cluster. The cell cluster is composed of undifferentiated cultured cells with migrating and differentiating cells forming the leading outer processes.

Figure 16:
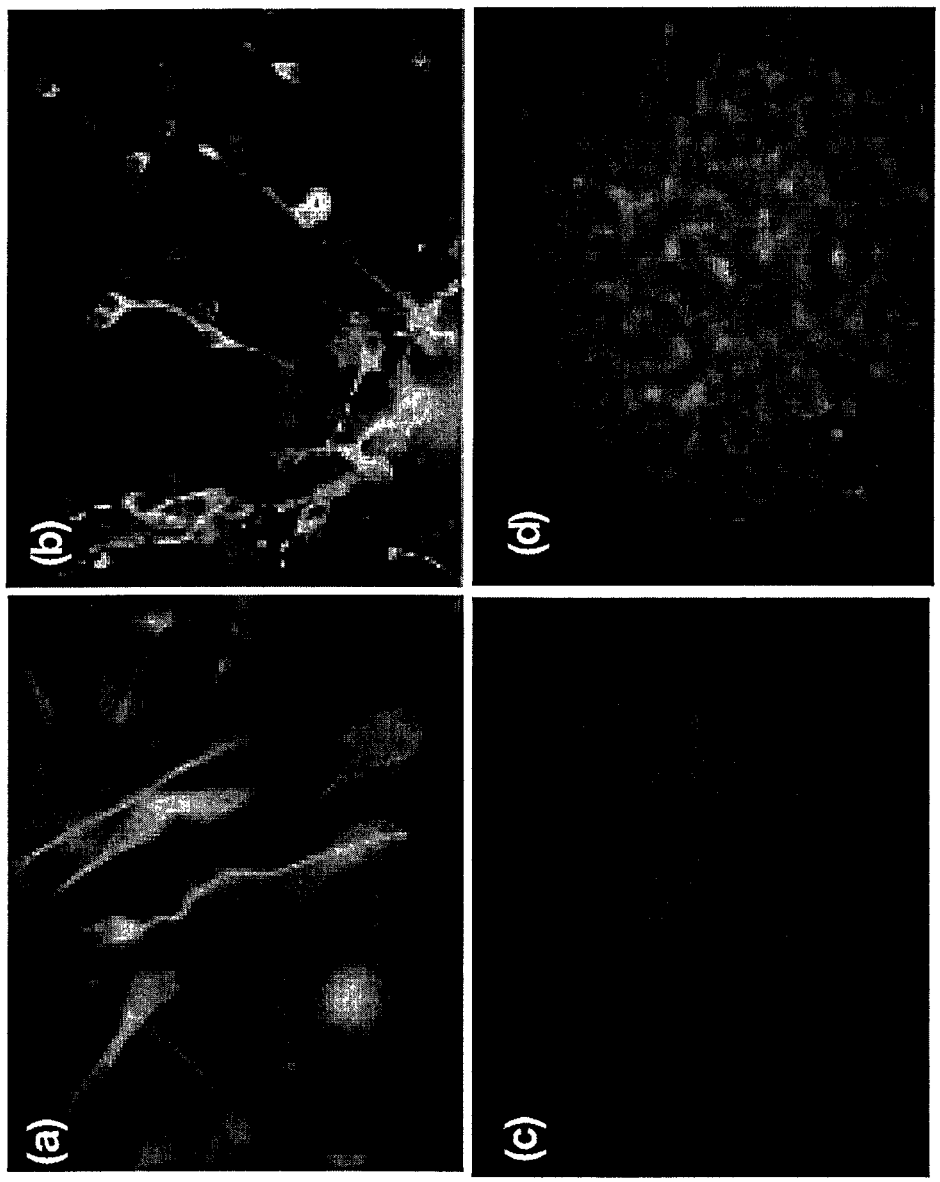
FIG. 16 shows expression of reelin, a3-integrin and Dab-1 in the human MNSCs. (a) reelin immunoreactivity was mainly detected in the neuronal like cells (green), while GFAP positive cells (red) also possess reelin immunoreactivity. (b) a3-integrin (green) expresses specifically in the neuron-like cell, while Dab-1 (red) express in most of the cells. (c) Dab-1 immunoreactivity (red) is highly localized in the nuclei. (d) In side of the cluster of MNSCs, we also detected reelin immunoreactivity (green).
Figure 17:
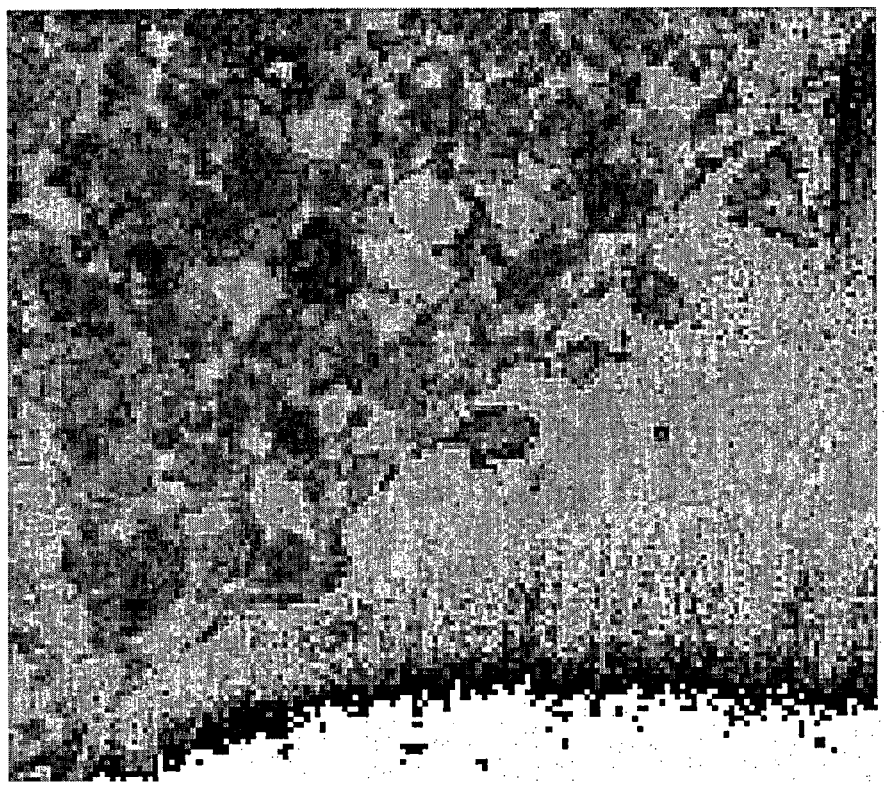
FIG. 17 shows an electron microscopic image showed that a3-integrin immunoreactivity was localized on the membrane of the cells.
Figure 18:
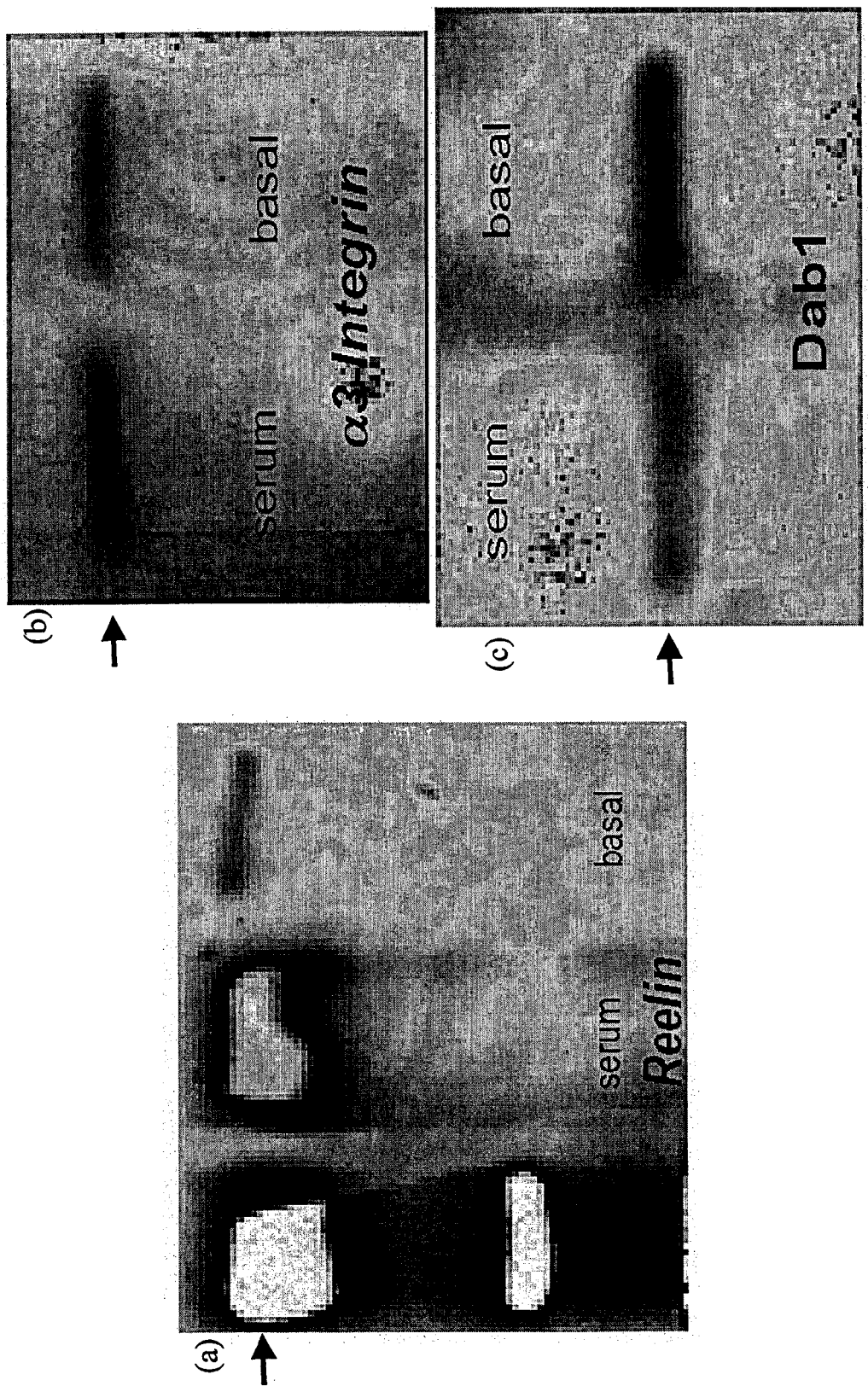
FIG. 18 shows Western blot analysis of (a) reelin, (b) a3-integrin and (c) DAB-1
Figure 19:
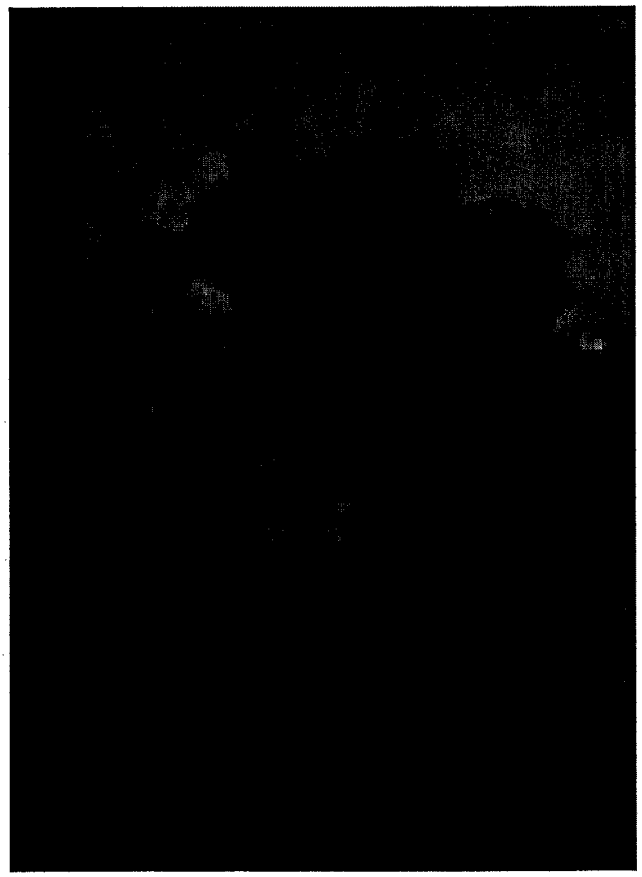
FIG. 19 shows reelin expression in embryonic stem cells. Reelin immunoreactivity is showed in green and the nuclei were stained with DAPI (blue).

To assess the presence of reelin and responsive mechanisms in HNSCs, immunocytochemistry and Western blot analysis were performed using antibodies recognizing reelin alpha 3-integrins (a3-integrins) and DAB-1. Five days after differentiation, reelin immunoreactivity (green) was present mainly on small bipolar cells suggestive of neurons, and very little reelin immunoreactivity was detected in GFAP positive cells (red), which are suggestive of astrocytes (FIG. 16a). a3-integrin immunoreactivity was also detected in small bipolar cells but not in GFAP-positive cells, indicating expression of a3 integrin predominant in neurons (FIG. 16b), while in DAB-1, a cytoplasmic adapter protein, immunoreactivity was detected in not only neurons but also in astrocytes (FIG. 16c). Intracellular distribution of DAB-1 was higher in the nucleus and was evenly distributed in the cytoplasm. Using the electron microscope, a3-integrin immunoreactivity was observed to be localized on the cell membranes (FIG. 17). In FIG. 16, reelin appears to have been released from reelin-positive cells and to have reached neighboring cells. Western blot analysis of samples prepared by immunoprecipitation from differentiated HNSCs with monoclonal antibody (Reelin 142) showed reelin, a3 integrin, and DAB-1 immunopositive bands (FIG. 18), indicating that these molecules interact with each other in the reelin signaling cascade, and that reelin released from a population of cells may coordinate movement of these cells as a regulator of stem cell biology.

Since reelin immunoreactivity was also present in the cell cluster before differentiation (FIG. 17d), it is possible that HNSC movement is organized by the active production of reelin within the center of the cluster, which may also serve to prevent a rapid state of differentiation. The cells located on the outer edge of the cluster, on the other hand, may be exposed to lower concentrations of reelin. Consequently, these cells are less restricted and begin to differentiate and migrate out from the center of the cluster. Since undifferentiated stem cells express reelin, reelin expression was also investigated in mouse embryonic stem cells. A subpopulation of embryonic stem cells in three days old embryos expressed reelin, indicating that reelin is a factor that regulates stem cell biology because it is expressed in embryonic stem cells before Cajal-Retzius cells begin to produce reelin during corticogenesis.

Example 8

Transplantation of Stem Cells to Reeler Mice

Figure 20:
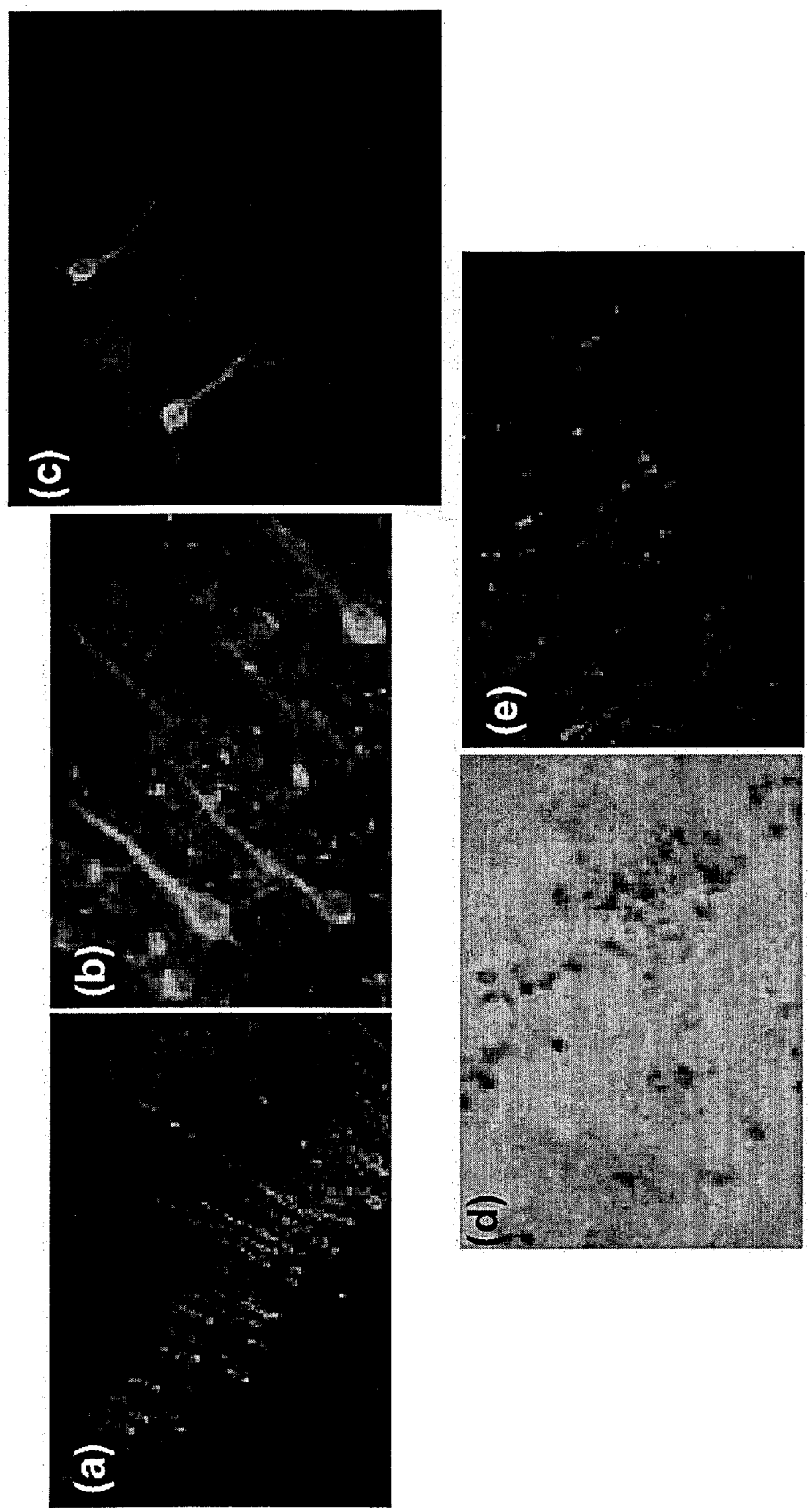
FIG. 20 shows immunohistochemistry of control mouse brain after human MNSC transplantation. (a) Human MNSCs migrated into the cortex and differentiated into neurons as indicated by bIII-tubulin positive cells (green). (b) Under higher magnification, neuronally differentiated cells (green) with BrdU positive nuclei (red) have morphologies typical of pyramidal cells. (c) Human MNSCs migrated into the hippocampus and differentiated into bIII-tubulin positive cells (green) with BrdU positive nuclei (red), having morphologies typical of pyramidal cells in CA1 pyramidal cell layer. (d) A layer of GFAP positive human MNSCs (brown) were found in the cortex. (e) Double-immunostaining revealed association of the GFAP positive cells (red) with the bIII-tubulin positive cells in the cortex.

The effects of reelin on the migratory and differentiation pattern of human MNSCs in vivo were investigated. Human MNSCs were expanded without differentiation as described above and treated by the incorporation of BrdU into nuclear DNA. Then, human MNSCs were injected in to the lateral ventricle of wild (c57/black) and reeler mice at one month old. Brain from these animals were investigated by immunohistochemistry for bIII-tubulin, GFAP, and BrdU four weeks after injection. Wild-type animals showed differentiation and distribution patterns of transplanted HNSCs similar to those found in previous rats transplantation studies (FIG. 20).

Figure 21:
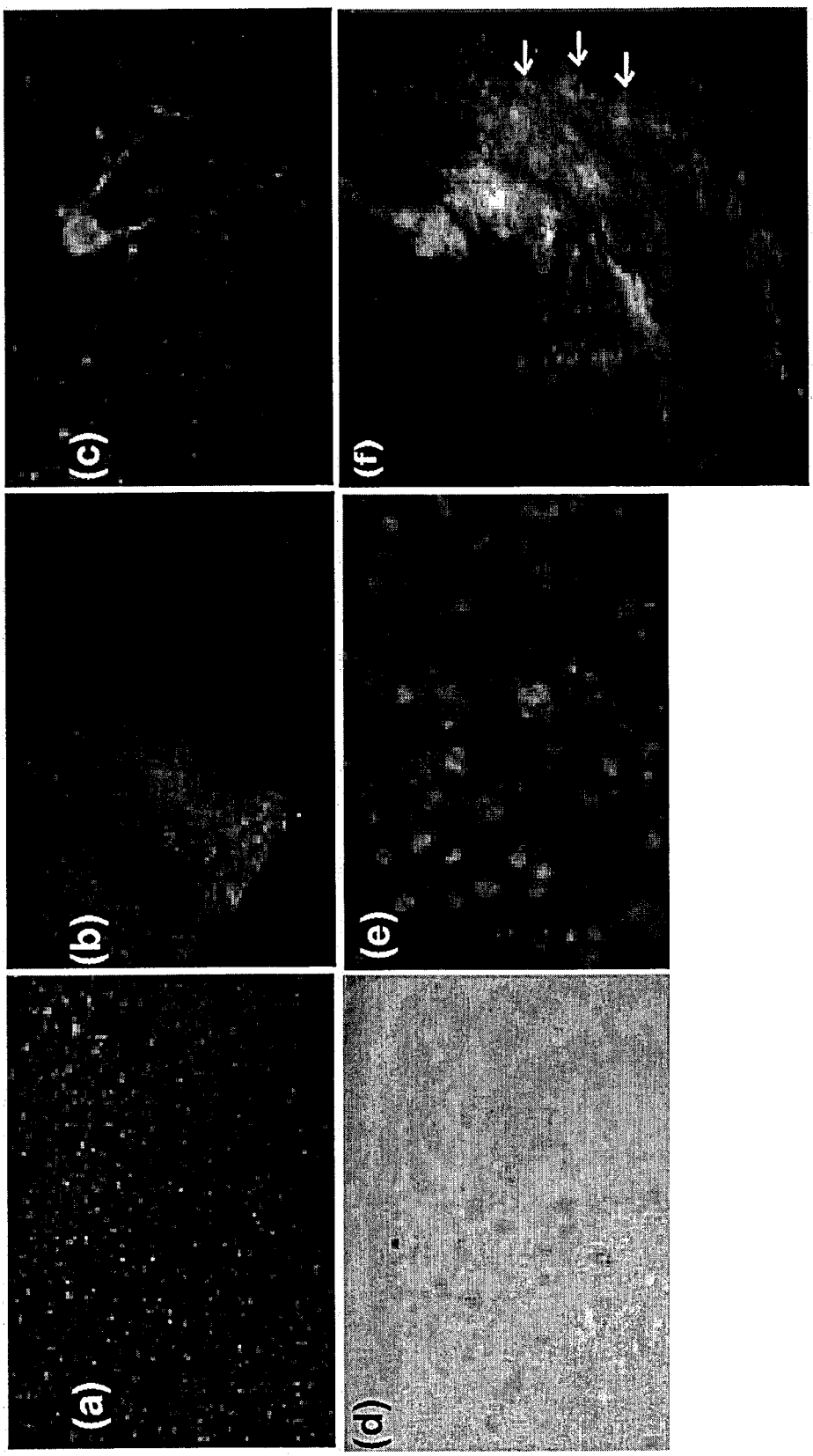
FIG. 21 shows immunohistochemistry of reeler mouse brain after human MNSC transplantation. (a) Few bIII-tubulin positive cells (green) were detected. (b) Under higher magnification, we found one group of BrdU positive cells on the side of the injection. (c) Differentiation of human MNSCs into bIII-tubulin positive cells in the hippocampus (green), having different morphologies than the cells found in the control animal in the CA1 pyramidal cell layer. Though the pyramidal cell layer is not particularly clear in this figure. (d) A few GFAP positive human MNSCs (brown) were found in the cortex. (e) A different morphology of bIII-tubulin (green) positive cells with BrdU positive nuclei (red) in the cortex. (f) Chain migration of reelin (green) positive cells in the cortex.

Human MNSCs transplanted in reeler mice did not successfully migrate into the host brain. In the cortex, a few GFAP-positive cells were detected (FIG. 21d), but bIII-tubulin positive HNSCs were not present (FIG. 21a). bIII-tubulin positive human MNSCs found near the injection site displayed an unusual morphology (FIG. 21b). Reelin positive human MNSCs showed a trained migration pattern in the white matter of the cortex (FIG. 21f), indicating that environmental reelin is necessary for the migration of NSCs and that the cells expressing reelin have potential to migrate in reeler mice.

Example 9

Analysis of Stem Cell Populations in Reeler Mice

Figure 22:
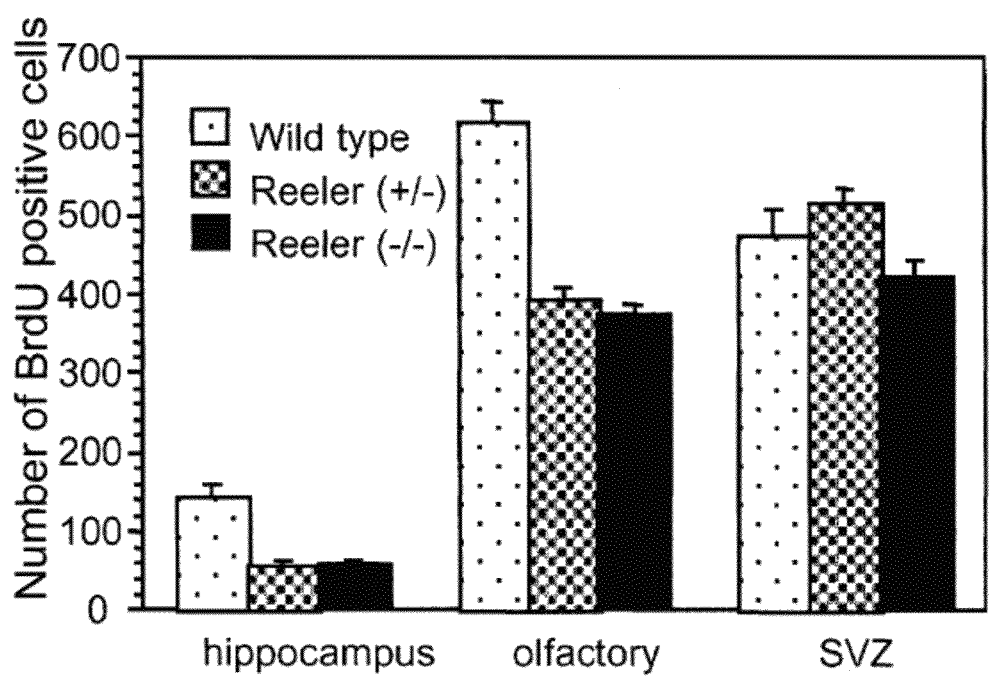
FIG. 22 shows neuronal counts of BrdU-positive cells in heterozygous (reeler (+/−), homozygous (reeler (−/−) and wild-type mice in the hippocampus, olfactory bulb, and SVZ. Significant reduction of the stem cell population was observed in the hippocampus (p<0.001) and olfactory bulb (p<0.01), but not in the SVZ of reeler (+/−) and reeler (−/−) mice compared with wild-type mice by Fisher's Protected LSD post hoc analysis after ANOVA.

Since the examples described herein indicate poor stem cells migration patterns in reeler mice, we suspected a similar migration pattern for endogenous stem cells. To investigate the endogenous stem cell population in reeler mice compared with the wild-type mice, BrdU (100 mg/kg/day) was injected into reeler homozygous, reeler heterozygous, and wild-type mice for four days. The hippocampus and SVZ of these mice were immunofluorescent stained for BrdU. Mouse NSCs, which proliferated during the injection period, incorporated BrdU into their nuclei, which can be detected as BrdU positive cells. Significantly reduced BrdU positive cells were found in the hippocampus of both reeler homozygous and heterozygous mice compared with wild-type mice (FIG. 22), while stem cell populations in SVZ of reeler homozygous and heterozygous mice were preserved (FIG. 22), indicating that the proliferation of stem cells was not affected, but the migration of the stem cells from SVZ to hippocampus was dramatically diminished by the lack of reelin.

Example 10

Isolation of Stem Cells from the Reeler Mice

Figure 23:
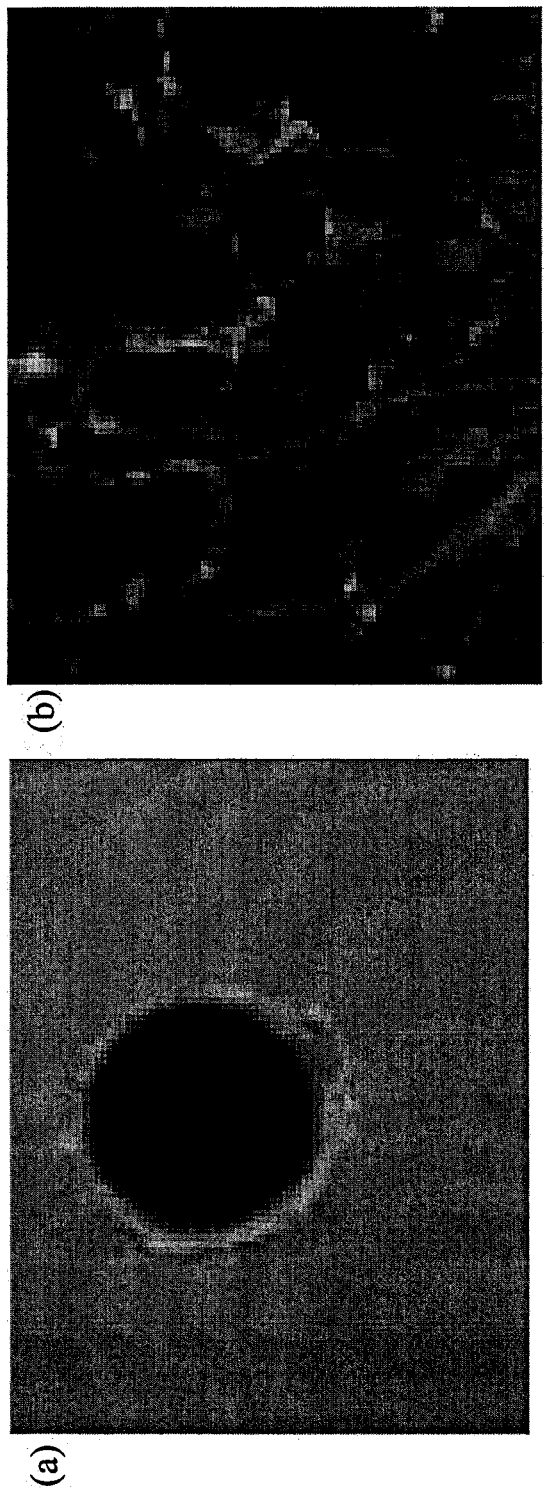
FIG. 23 shows stem cells isolated from adult mice. (a) During in vitro expansion, the stem cells formed a cluster of multiple cells similar to those seen with NSCs. (b) The stem cells differentiated into bIII-tubulin (green) and GFAP positive cells (red), indicating multipotency of these cells.

NSCs were isolated from adult mice (4 months old, C57/ black) as responders for bFGF. They were expanded in vitro using the same media as used for human MNSC cultures. The cells formed clusters (FIG. 23a), which are similar to the ones formed by the NSCs. These NSCs were capable of producing neurons and astrocytes by differentiation after three months of in-vitro expansion (FIG. 23b).

Example 11

Characteristics of Differentiated Human MNSCs Under Non-Serum Condition

Figure 24:
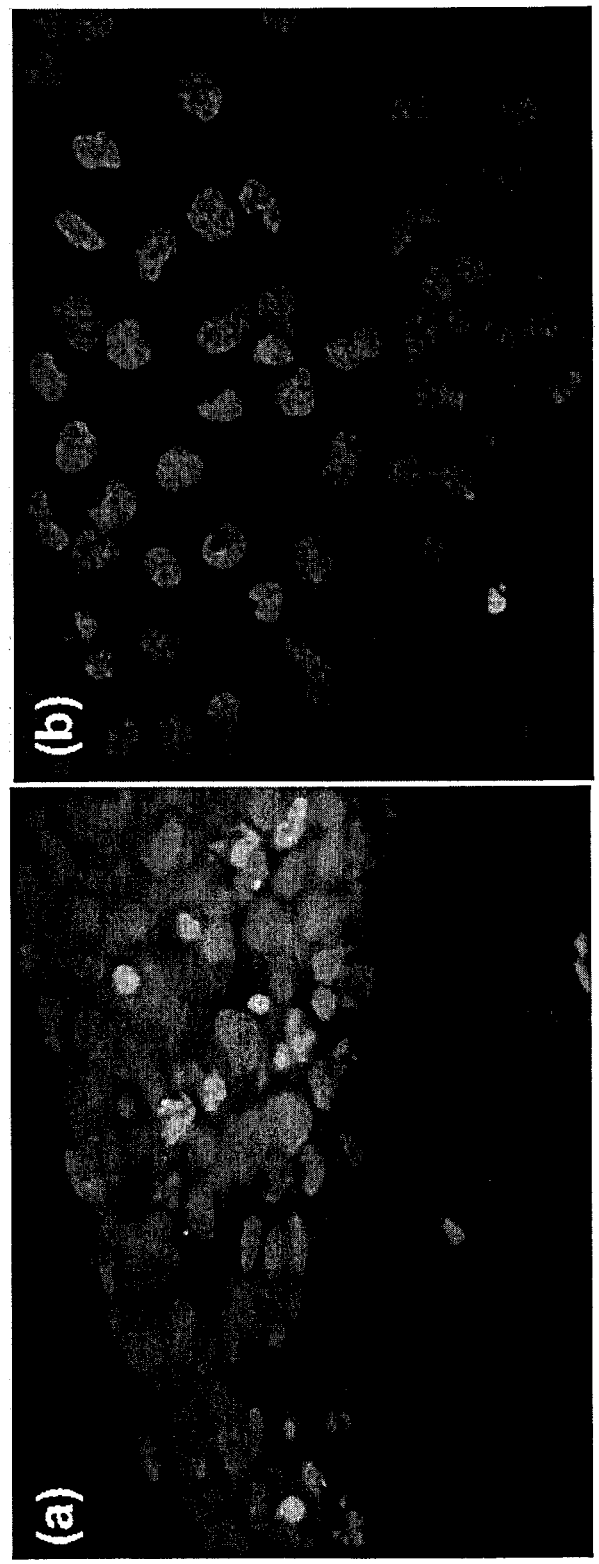
FIG. 24 shows that the human MNSCs were undergoing a much greater degree of apoptotic cell death (yellow) during differentiation in a serum-free unsupplemented medium (a) when compared to serum differentiation (b). The Fluorescein Apoptosis Detection System (Promega, Madison, Wis.) was used to assay the DNA fragmentation of HNSCs at 3 DIV. All the nuclei of HNSCs were counterstained by propidium iodide (red) and the DNA fragmentation-positive cells were stained in green.
Figure 25:
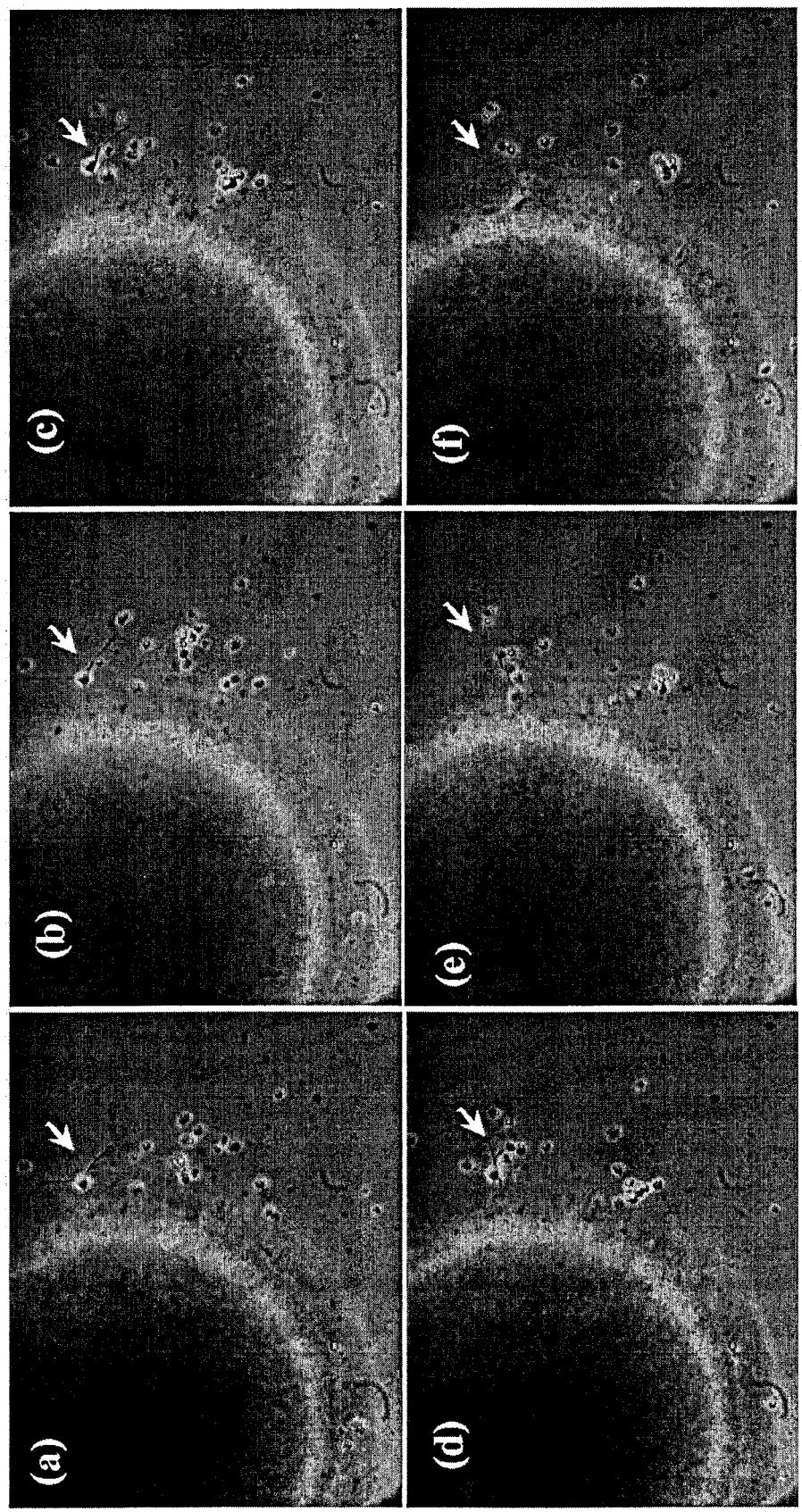
FIG. 25 shows time-lapse video microscopy monitoring the characteristics of MNSC differentiation in cultures plated in a serum-free unsupplemented medium at 2 DIV. The differentiating MNSCs (arrow) migrate away from the cluster of cells (a). Interestingly, these cells are extending processes onto nearby the morphologically shrunken, apparently apoptotic, cells (b), followed by retraction of the processes (c). The processes appeared to be attached to the apoptotic cells (d), which were drawn back into the cluster of cells (e,f). The response of differentiating NSCs to the apoptotic cells further suggested that some component(s) of the apoptotic cells serve as factors capable of influencing the physiological activity of differentiating NSCs.

During the early stages (1-3 days in vitro, DIV) of serum-free differentiation, many human MNSCs exhibited the same type of shrunken morphology that cells undergoing apoptotic cell death display. To further assess the type of cell death, a TUNEL assay was used to detect in situ DNA fragmentation, an early marker of apoptosis, in HNSCs differentiated in serum or in serum-free media. Many cells were positive for the TUNEL signal under serum-free differentiation conditions and displayed somal shrinkage followed by cell detachment from the culture plates. In contrast, only a few TUNEL-positive cells were detected under serum differentiation conditions (FIG. 24). Since neurons are known to undergo apoptosis after serum deprivation, and B27 is reported to prevent neuronal death in cultured cortical tissue, apoptosis of human MNSCs in serum-free differentiation conditions may be due to supplement deprivation. Our time lapse video microscopic study of human MNSCs plated in serum-free unsupplemented media for 1 DIV revealed that differentiating human MNSCs appear to reach out to the nearby morphologically apoptotic cells described above (FIG. 25). These results suggest that human MNSCs initially become apoptotic under serum-free differentiation conditions and subsequently express migration and/or differentiation factors to influence the fate of neighboring cells.

Figure 26:
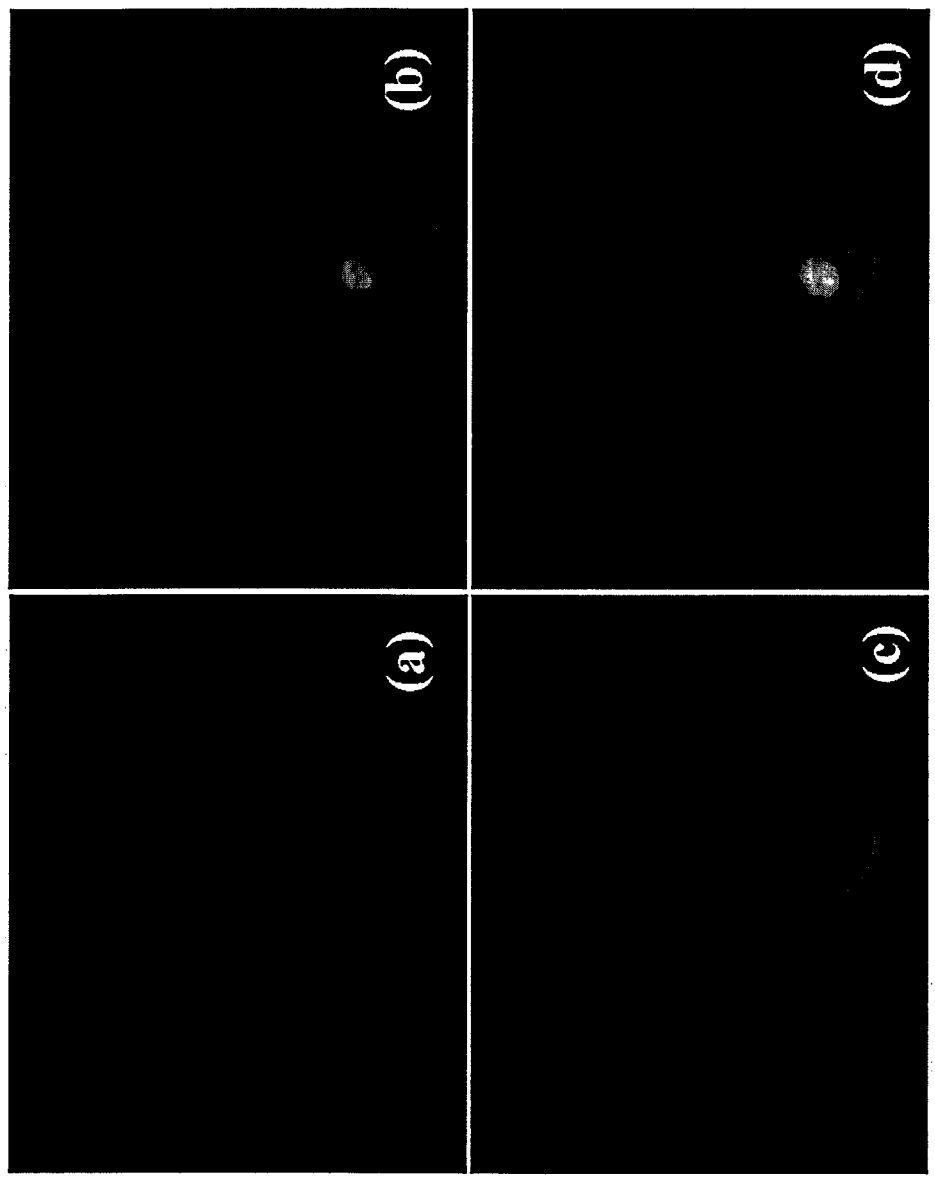
FIG. 26 shows that apoptotic cells in the serum-free differentiation conditions were APP immunopositive. All the nuclei of HNSCs were counter-stained by DAPI (a, blue). The TUNEL signal (b, green) and immunoreactivity for APP recognized by the 22C11 monoclonal antibody (which recognized the N-terminal end of APP) (c, red) are co-localized in the cells of shrunken morphology in the serum-free differentiation condition (d).

A combination of immunocytochemistry with 22C11, which is a monoclonal antibody recognizing the N-terminal end of APP and the TUNEL assay revealed a marked increase of APP immunoreactivity in the TUNEL-signal-positive cells under serum-free differentiation conditions compared to the background levels of APP found in neighboring human MNSCs (FIG. 26). This result not only confirms previous findings, that APP expression is elevated in the apoptotic cells, but more importantly suggests that one factor produced in apoptotic cells to influence the differentiation of neighboring cells could be the N-terminal fragment of APP.

Example 12

Figure 27:
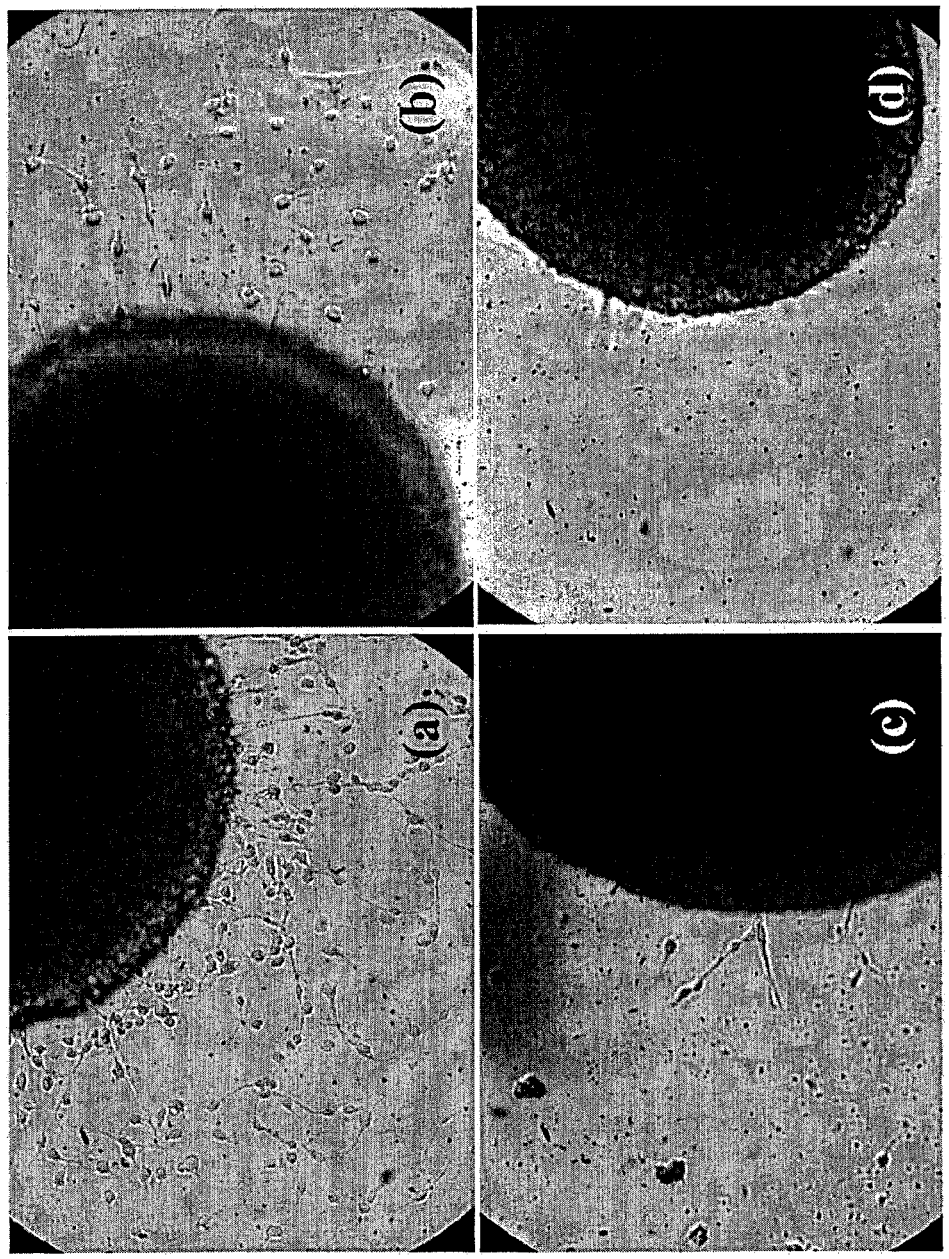
FIG. 27 shows that treatment of human MNSCs in the non-serum unsupplemented media with the 22C11 monoclonal antibody recognizing the N-terminal end of APP dose-dependently inhibited their differentiation. The panels show typical morphology of human MNSCs when treated with 22C11 (a; control, b; 125 µg/ml, c; 250 µg/ml, d; 500 µg/ml 22C11) at 3 DIV.

Inhibition of Human MNSC Differentiation Under Non-Serum Conditions by an Antibody Against APP To investigate the involvement of the secreted APP fragment during differentiation, HNSCs were co-incubated in serum or serum-free differentiation conditions for three days with various 22C11 concentrations. The addition of 22C11 to the culture dose-dependently (125, 250, 500 µg/ml) inhibited differentiation of human MNSCs under serum-free unsupplemented conditions (FIG. 27). In contrast, 22C11 treatment did not inhibit the differentiation of human MNSCs under serum differentiation conditions (data not shown). These results suggest that APP is involved in the differentiation of human MNSCs under serum-free differentiation conditions while differentiation factors independent of the APP pathway exist under serum differentiation conditions.

Example 13

Treatment of HNSCs with Secreted-Type APP

Figure 28:
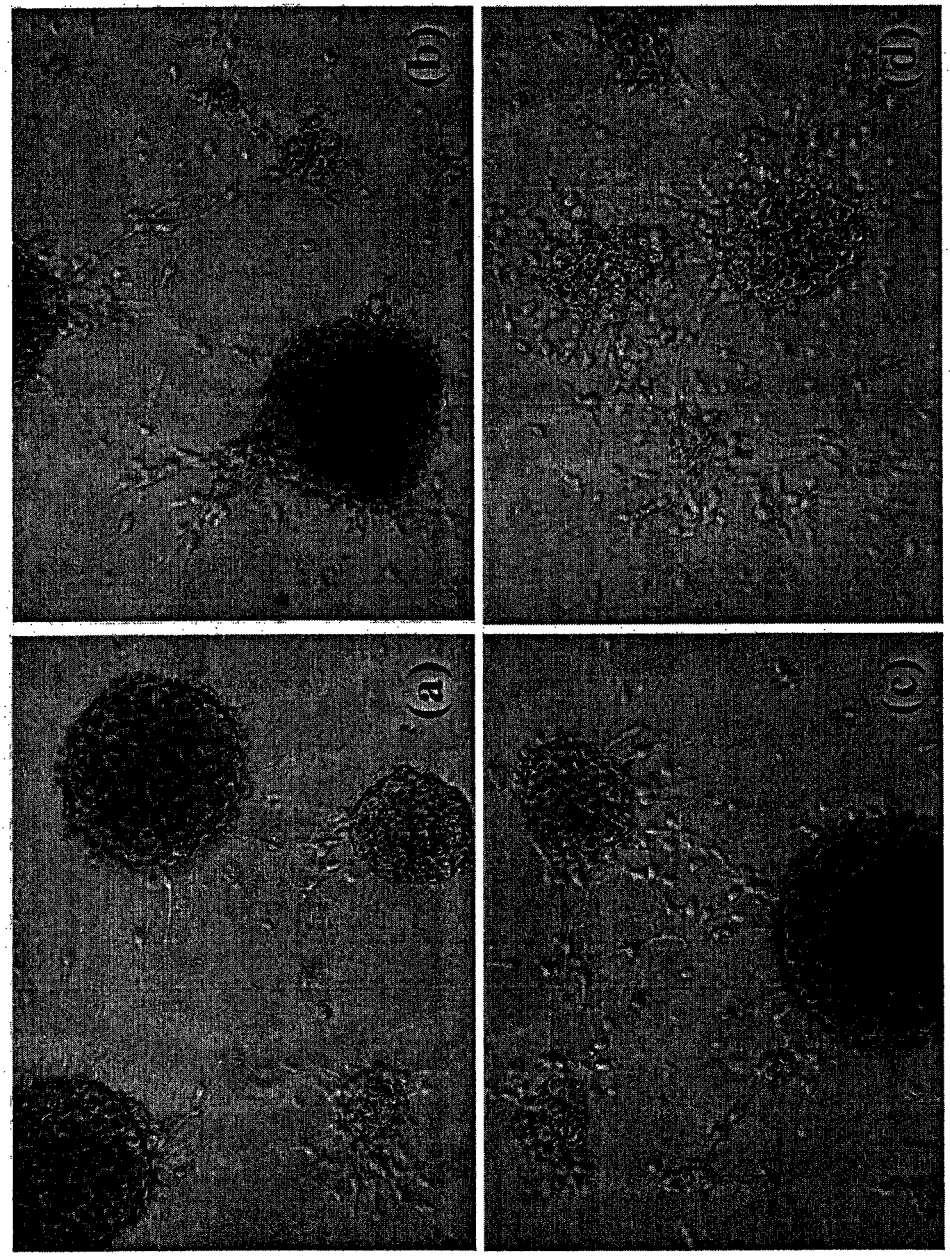
FIG. 28 shows that the treatment of the human MNSCs in culture with the recombinant secreted type of amyloid precursor protein (sAPP) for 5 days dose-dependently increased the differentiation of human MNSCs under serum-free unsupplemented condition (a; control, b; 25 ng/ml, c; 50 ng/ml and d; 100 ng/ml).

To investigate whether 22C11-induced inhibition of human MNSC differentiation occurs through the sequestering of sAPP or by blocking the N-terminal domain of APP on the membrane of differentiating cells, human MNSCs were treated with exogenous sAPP. Recombinant human sAPP was produced in yeast, which contains 95% sAPP695T (ending at amino acid 505 of 695) and 5% sAPP695. The addition of recombinant sAPP to the cell culture media dose-dependently (25, 50 and 100 ng/ml) differentiated human MNSCs (FIG. 28) under serum-free differentiation conditions. This result suggests that the sequestering of sAPP by 22C11 may play a role in inhibiting HNSC differentiation. sAPP treatment did not increase the TUNEL signal in human MNSCs (data not shown).

Figure 29:
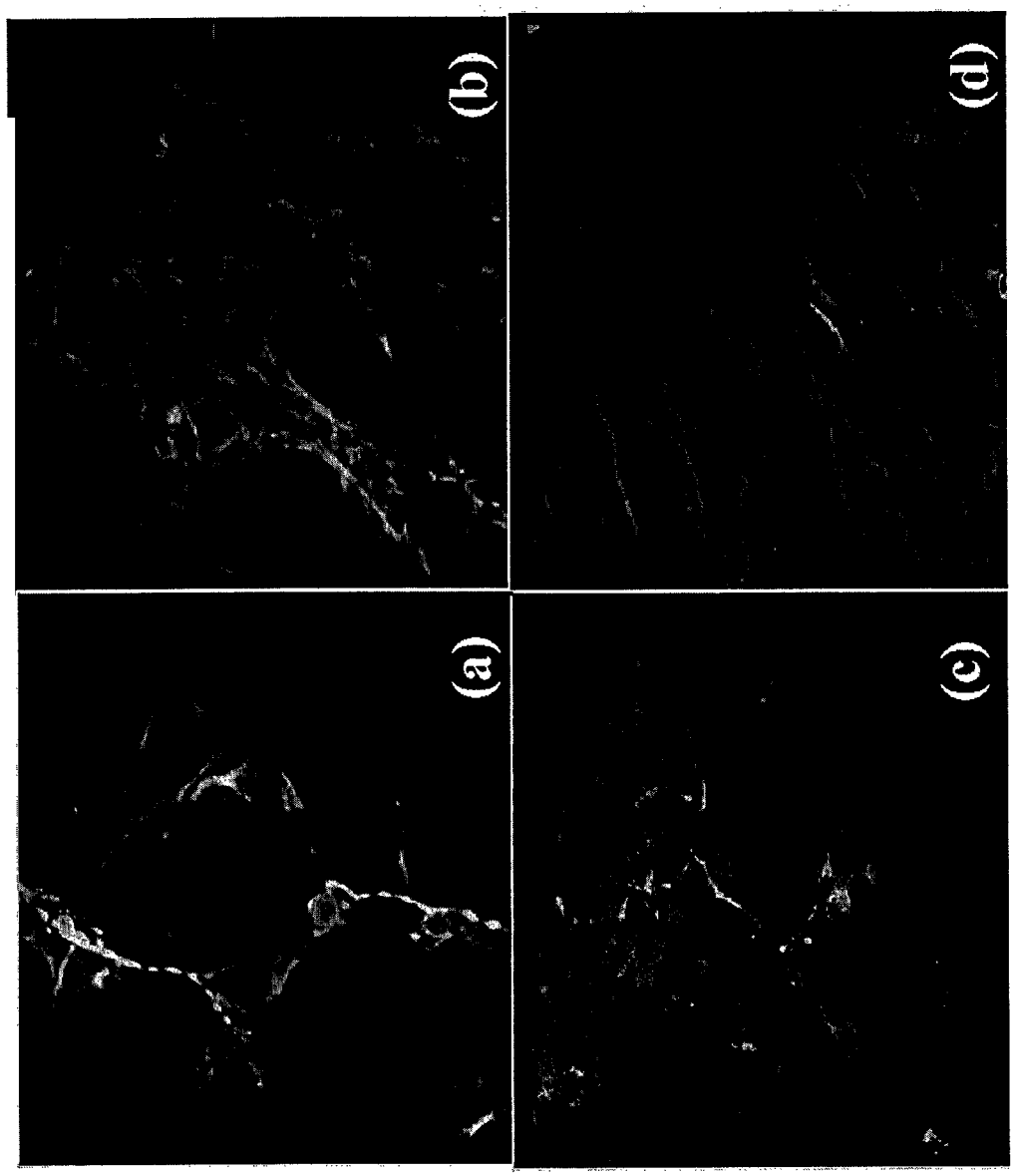
FIG. 29 shows that the cell population of sAPP-treated human MNSCs at 5 DIV in serum-free differentiation condition was characterized by double immunofluorescence staining with GFAP (red) and bIII-tubulin (green), which are markers for astrocytes and neurons respectively. All nuclei were counter stained by DAPI (blue). The panels show typical morphology and differentiation pattern of human MNSCs treated with (a); control, (b); 25 ng/ml, (c); 50 ng/ml and (d); 100 ng/ml of sAPP. At low doses of sAPP (e.g., 25 ng/ml), increased glial (red) and neuronal (green) differentiation was observed as compared to the control. With higher doses of sAPP, many glialy differentiated human MNSCs (red) were observed.
Figure 30:
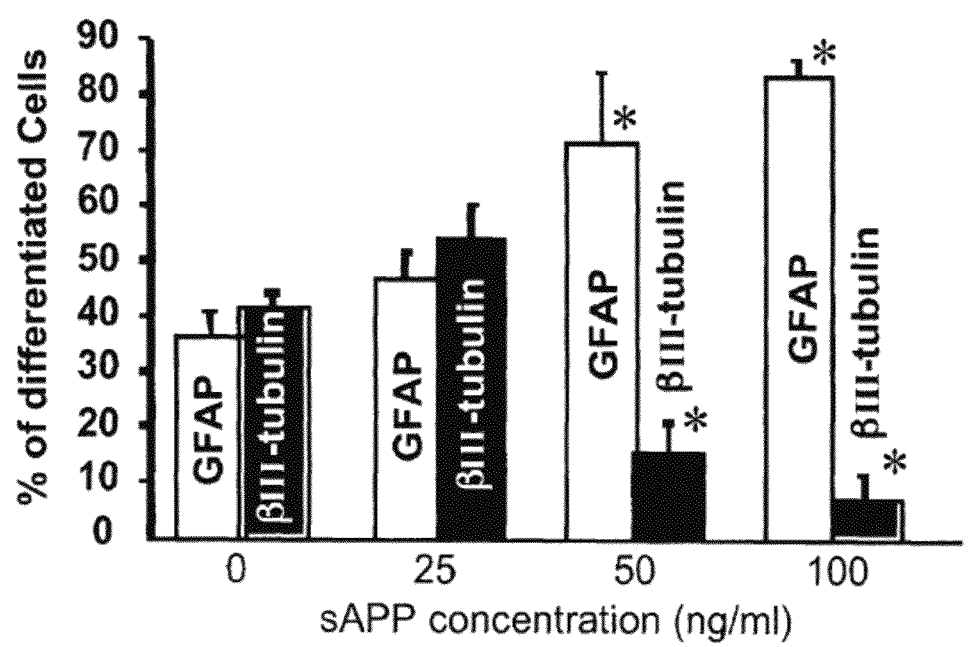
FIG. 30 shows the quantitative population analysis of the each differentiation type. Cells immunostained for GFAP and bIII-tubulin were tallied versus total cell numbers of DAPI-labeled nuclei. All data values reported are expressed as mean percentages (±S.E.M.). One Factor ANOVA followed by post hoc analysis (Student-Newman-Keuls) was used to demonstrate statistically significant differences between experimental groups and control (*: $p<0.01$).

The cell population of sAPP-treated human MNSCs at 5 DIV under the serum-free differentiation condition was also characterized by double immunofluorescence labeling of GFAP and bIII tubulin (FIG. 29). Treatment with sAPP dose dependently (25, 50, 100 ng/ml) increased the population of GFAP positive cells from an average of 45% in controls (no sAPP) to an average of 83% using the highest concentration of sAPP (100 ng/ml at 5 DIV). Higher doses of sAPP (50 and 100 ng/ml) dose-dependently decreased bIII-tubulin-positive neurons in the total population of differentiated human MNSCs, from an average of 51% in controls to an average of 13% in the highest concentration of sAPP (FIG. 30). These results indicate that sAPP released from dying cells promotes differentiation of human MNSCs while causing gliogenesis at higher doses. sAPP can influence the cell fate decision of human MNSCs by increasing glial differentiation; sAPP may cause an accelerated migration of astrocytes resulting in increased levels of glial cell differentiation; and high concentrations of sAPP may reduce or eliminate the human MNSC population differentiating into neurons, since high APP expression in neuronal cell lines have been reported to cause apoptotic cell death by caspase 3 activation.

Example 14

Effect of APP Transgene to Human MNSCs

Figure 31:
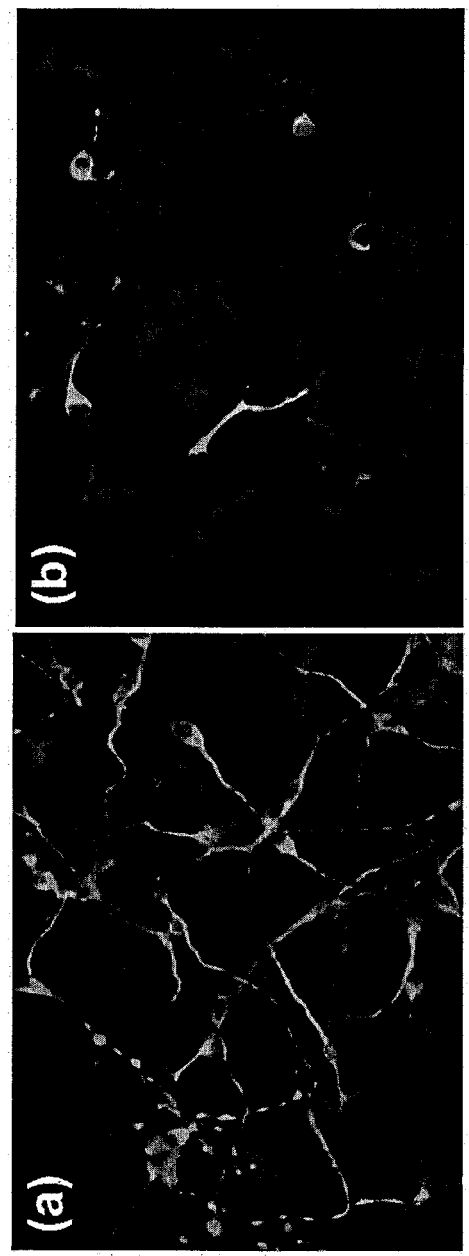
FIG. 31 shows that human MNSCs transfected with mammalian expression vectors containing genes for either wild type APP (wtAPP) that were differentiated under serum-free unsupplemented conditions displayed a significantly higher level of glial differentiation as compared to human MNSCs transfected with the vector alone at 5 DIV. Pictures show double immunofluorescence staining with GFAP (red) and bIII-tubulin (green), which are markers for astrocytes and neurons respectively. All nuclei were counter stained by DAPI (blue).

To confirm the glial differentiation promoting effect of sAPP, human MNSCs were transfected with mammalian expression vectors containing genes for either wild-type APP or sAPP and differentiated under serum-free unsupplemented conditions. Human MNSCs transfected with wild-type APP revealed a significantly higher level of glial differentiation compared with human MNSCs transfected with the vector alone at 5 DIV (FIG. 31). These results indicate that in addition to the excess of sAPP, wild-type APP over-expression can also induce glial differentiation of HNSCs. This finding may have relevance in Down Syndrome (DS), a chromosomal abnormality resulting in trisomy 21. In addition to its characteristic physical manifestations, DS patients often exhibit early-onset AD. Since the APP gene is also located on chromosome 21, the increase of APP gene expression by trisomy 21 may explain the excess amount of APP in the brain. It has been suggested that APP plays a role in neuronal development and that the earlier appearance of AD in adult DS patients is associated with an abnormal regeneration process related to aging.

Example 15

Transplantation of HNSCs to APP Knockout Mice

The regulatory effect of APP on human MNSCs biology in vivo was further invastigatred by transplanting HNSCs into the brains of APP knockout mice.

Figure 32:
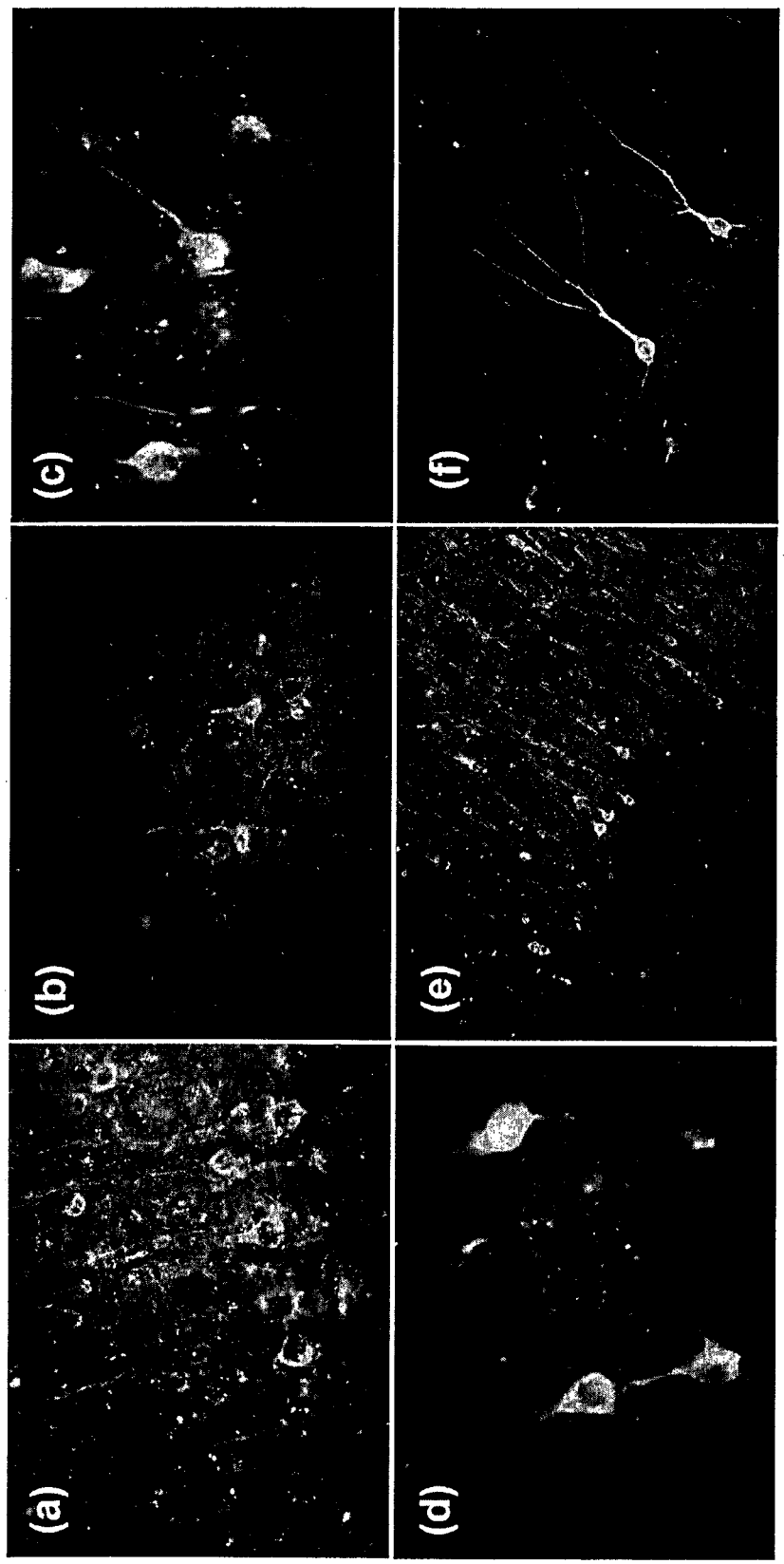
FIG. 32 shows that the human MNSCs transplanted to APP knockout mouse brain show less migration and differentiation as compared to cells transplanted into wild type control mice. Human MNSCs were treated with BrdU before the unilateral ventricle injection to aid in the discrimination from host cells. Brain tissues were immunoblotted for bIII-tubulin, GFAP, and BrdU 4 weeks post-injection. In the wild type mice, the immunopositive cells for BrdU (red) and bIII-tubulin (green) distributed bilaterally in the singular and parietal cortexes (a) and pyramidal layer of the hippocampus (c), indicating neuronal differentiation of transplanted human MNSCs. The human MNSCs also differentiated into GFAP-immunopositive cells (red) that localized with the bIII tubulin (green) stained neuronal fibers of layer III in the cortex (e). The differentiation and distribution patterns of the transplanted human MNSCs were similar to what we found in our previous transplantation study with rats. In the APP knockout mice, those bIII-tubulin positive cells (green) with BrdU positive nuclei (red), derived from the transplanted human MNSCs, that were seen in the cortex were scarcely distributed and lacked apical dendrites (b). In the hippocampus, bIII-tubulin (green) and BrdU (red) immunopositive cells had quite similar distribution and structure to the cells found in the wild type mice (d,f).

To differentiate between host and transplanted cells, human MNSCs were labeled in vitro by the incorporation of bromodeoxyuridine (BrdU) into the DNA before transplantation. These labeled cells (about $10^5$) were subsequently injected unilaterally into the cerebral lateral ventricle of c57/black wild-type and APP knockout mice at 2 months of age. Immunohistochemical examination of wild-type brain sections four weeks after transplantation revealed migration and differentiation patterns similar to the previous study with human MNSC transplantation to aged, memory-impaired rats described above. Cells distributed bilaterally in the singular and parietal cortexes (layer II, IV and V) (FIG. 32a) and hippocampus (pyramidal cell layer) (FIG. 35c) were intensely and extensively immunopositive for BrdU and human bIII-tubulin. The transplanted human MNSCs also differentiated into GFAP-immunopositive cells that co-localized with the neuronal fibers of layer III in the cortex (FIG. 32e). These morphologies and distributions of bIII-tubulin- or GFAP-positive cells were not detected in wild-type control mice that did not receive human MNSC transplantation.

Although human MNSCs transplanted into the APP knockout mice also differentiated into bIII-tubulin and GFAP-positive cells, distribution and migration patterns were not symmetric and the number of the differentiated cells was lower than in compared to control wild-type mice. Despite the rather uniform bIII-tubulin positive cell distribution and structure in the hippocampus of APP knockout mice (FIG. 32d,f), bIII tubulin positive HNSCs were scarcely distributed in the cortex and lacked apical dendrites (FIG. 32b). Although it is conceivable that the APP expression of transplanted human MNSCs may partially compensate for the APP deficit in the host brain, it is quite apparent that such levels of expression are negligible and that the absence of environmental APP clearly alters the migration pattern of transplanted HNSCs. These results indicate that there were insufficient environmental factors to properly guide the migration and differentiation of HNSCs in APP knockout mice, and that environmental or secreted APP may be important factors in regulating cell fate and migration of human MNSCs in vivo.

Example 16

Analysis of Stem Cell Populations in APP Knockout Mice

Figure 33:
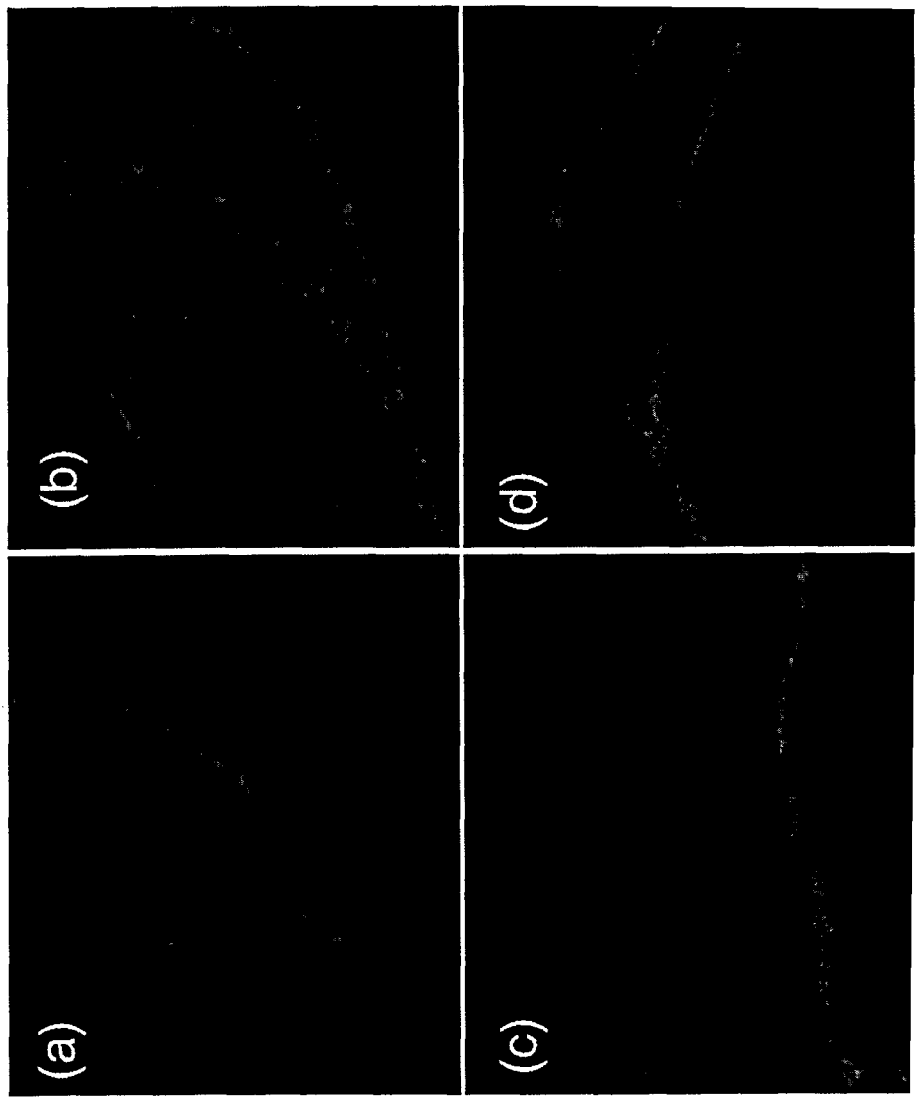
FIG. 33 shows a comparison of endogenous NSC populations in APP knockout and wild-type mice (×100). BrdU incorporated into the nuclei of proliferating cells was detected by fluorescent immunohistochemistry (red), and all the nuclei were counterstained with DAPI (blue). The upper panels show a dramatically decreased population of stem cells in the hippocampus of APP knockout mouse (a) compared with wild-type mouse (b). The lower panels show a similar population of stem cells in the subventricular zone (SVZ) of APP-knockout mice (c) compared with wild-type mice (d).

Since the results set forth above indicated inadequate stem cells migration patterns in APP knockout mice, a similar migration pattern was expected for endogenous stem cells. To investigate this, the endogenous stem cell population in APP mice were compared with wild-type mice. BrdU (100 mg/kg/day) was injected into APP knockout and wild-type mice for four days. The hippocampus and SVZ of the test mice were immunofluorescently stained for BrdU. Mouse NSCs, which proliferated during the injection period, incorporated BrdU into their nuclei, which can be immunofluorescently detected. BrdU-positive cells in the hippocampus of APP knockout mice were reduced compared with wild-type mice (FIG. 33); whereas, stem cell populations in SVZ of APP knockout mice were preserved (FIG. 33), indicating that the proliferation of stem cells was not affected, but the migration of stem cells from SVZ to the hippocampus was decreased by the lack of APP.

It should be understood that the foregoing disclosure emphasizes certain specific embodiments of the invention and that all modifications or alternatives equivalent thereto are within the spirit and scope of the invention as set forth in the appended claims.

We claim:

1. A method for treating a human patient having a neurological deficit, the neurological deficit being a spinal cord injury, the method comprising the step of: (a) administering a pharmaceutically effective amount of more developmentally potent human cells to the human patient; wherein the more developmentally potent human cells are obtained by contacting human mesenchymal stem cells with an effective amount of BrdU for an effective period, wherein the BrdU-contacted, human mesenchymal stem cells become more developmentally potent human cells capable of migrating to an area of tissue damage, and functioning in a manner that reduces the neurological deficit, wherein the more developmentally potent cells are implanted into a body cavity that is fluidly-connected to the area of neurological deficit.

2. The method of claim 1 wherein the cells are administered by injecting the more developmentally potent human cells with a syringe, inserting the more developmentally potent human cells with a catheter or surgically implanting the more developmentally potent human cells.

3. The method of claim 1 wherein the more developmentally potent human cells comprise a cluster of two or more cells.

4. The method of claim 1 wherein the more developmentally potent human cells are injected with a syringe into a body cavity that is fluidly-connected to the area of neurological deficit.

5. The method of claim 1 wherein the more developmentally potent human cells are inserted with a catheter into a body cavity that is fluidly-connected to the area of neurological deficit.

6. The method of claim 1 wherein the more developmentally potent human cells are surgically implanted to the area of neurological deficit.

* * * * *